US009801912B2

(12) United States Patent
Frank et al.

(10) Patent No.: US 9,801,912 B2
(45) Date of Patent: Oct. 31, 2017

(54) ABCB5(+) STEM CELLS FOR TREATING OCULAR DISEASE

(71) Applicants: VA Boston Healthcare System, Boston, MA (US); Schepens Eye Research Institute, Boston, MA (US); Children's Medical Center Corporation, Boston, MA (US)

(72) Inventors: Markus H. Frank, Cambridge, MA (US); Natasha Y. Frank, Cambridge, MA (US); Bruce Ksander, Boston, MA (US); Paraskevi Evi Kolovou, Boston, MA (US)

(73) Assignees: VA Boston Healthcare System, Boston, MA (US); Schepens Eye Research Institute, Boston, MA (US); Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/768,885

(22) PCT Filed: Feb. 19, 2014

(86) PCT No.: PCT/US2014/017076
§ 371 (c)(1),
(2) Date: Aug. 19, 2015

(87) PCT Pub. No.: WO2014/130518
PCT Pub. Date: Aug. 28, 2014

(65) Prior Publication Data
US 2015/0374756 A1  Dec. 31, 2015

Related U.S. Application Data

(60) Provisional application No. 61/766,424, filed on Feb. 19, 2013.

(51) Int. Cl.
| A61K 35/30 | (2015.01) |
| C12N 5/079 | (2010.01) |
| C12N 5/0775 | (2010.01) |
| A61K 9/00 | (2006.01) |
| A61L 27/38 | (2006.01) |
| C12N 5/0797 | (2010.01) |

(52) U.S. Cl.
CPC ............ *A61K 35/30* (2013.01); *A61K 9/0051* (2013.01); *A61L 27/3834* (2013.01); *A61L 27/3839* (2013.01); *C12N 5/0621* (2013.01); *C12N 5/0623* (2013.01); *C12N 5/0668* (2013.01); *A61L 2430/16* (2013.01)

(58) Field of Classification Search
None
See application file for complete search history.

(56) References Cited

U.S. PATENT DOCUMENTS

| 5,434,075 A | 7/1995 | Mechetner et al. |
| 5,906,934 A | 5/1999 | Grande et al. |
| 6,152,142 A | 11/2000 | Tseng |
| 6,355,239 B1 | 3/2002 | Bruder et al. |
| 6,387,367 B1 | 5/2002 | Davis-Sproul et al. |
| 6,464,983 B1 | 10/2002 | Grotendorst |
| 6,541,024 B1 | 4/2003 | Kadiyala et al. |
| 6,755,807 B2 | 6/2004 | Risk, Jr. et al. |
| 6,797,269 B2 | 9/2004 | Mosca et al. |
| 6,846,883 B2 | 1/2005 | Frank et al. |
| 6,875,430 B2 | 4/2005 | McIntosh et al. |
| 6,905,678 B2 | 6/2005 | Havenga et al. |
| 7,029,666 B2 | 4/2006 | Bruder et al. |
| 7,465,554 B2 | 12/2008 | Frank et al. |
| 7,928,202 B2 | 4/2011 | Frank et al. |
| 8,076,091 B2 | 12/2011 | Frank et al. |
| 8,425,876 B2 | 4/2013 | Frank et al. |
| 8,455,245 B2 | 6/2013 | Frank |
| 8,507,273 B2 | 8/2013 | Frank et al. |
| 8,697,072 B2 | 4/2014 | Frank et al. |
| 9,266,946 B2 | 2/2016 | Frank et al. |
| 9,561,264 B2 | 2/2017 | Frank et al. |
| 2001/0007658 A1 | 7/2001 | Usala et al. |
| 2002/0037522 A1 | 3/2002 | Frank et al. |
| 2002/0068913 A1 | 6/2002 | Fleischmann |
| 2002/0127736 A1 | 9/2002 | Chou et al. |
| 2002/0150720 A1 | 10/2002 | Howard et al. |
| 2005/0049185 A1 | 3/2005 | Frank et al. |
| 2005/0249728 A1 | 11/2005 | Singh et al. |
| 2007/0116691 A1 | 5/2007 | Cambier et al. |
| 2008/0003206 A1 | 1/2008 | Frank |
| 2009/0117117 A1 | 5/2009 | Frank et al. |
| 2009/0162873 A1 | 6/2009 | Frank et al. |
| 2010/0145030 A1 | 6/2010 | Frank et al. |
| 2011/0165149 A1 | 7/2011 | Frank et al. |
| 2011/0287034 A1 | 11/2011 | Frank et al. |
| 2012/0034196 A1 | 2/2012 | Frank et al. |
| 2013/0287785 A1 | 10/2013 | Frank et al. |
| 2013/0315880 A1 | 11/2013 | Frank |
| 2014/0302031 A1 | 10/2014 | Frank et al. |
| 2016/0009804 A1 | 1/2016 | Frank et al. |
| 2016/0106782 A1 | 4/2016 | Frank et al. |
| 2016/0136297 A1 | 5/2016 | Frank et al. |

FOREIGN PATENT DOCUMENTS

| WO | WO 2005/079145 A2 | 9/2005 |
| WO | WO 2006/103685 A2 | 10/2006 |

(Continued)

OTHER PUBLICATIONS

Cotsarelis et al. Cell, 1989, vol. 57, Issue 2, pp. 201-209.*

(Continued)

*Primary Examiner* — Allison Fox
(74) *Attorney, Agent, or Firm* — Wolf, Greenfield & Sacks, P.C.

(57) ABSTRACT

Various aspects and embodiments of the present invention are directed to methods of treating a subject having an ocular condition, methods of isolating ocular stem cells, methods of selecting and/or producing ocular grafts for transplantation, and methods of promoting ocular cell regeneration as well as to grafts and preparations containing isolated ocular stem cells characterized by the expression of ABCB5 on their cell surface.

10 Claims, 40 Drawing Sheets

(56) References Cited

FOREIGN PATENT DOCUMENTS

| WO | WO 2007/143139 A1 | 12/2007 |
|---|---|---|
| WO | WO 2013/002953 A1 | 1/2013 |
| WO | WO 2014/130518 A1 | 8/2014 |

OTHER PUBLICATIONS

Ksander et al, Nature, Jul. 17, 2014, vol. 511, pp. 353-357.*
Eveleth, "Cell based therapies for Ocular Diseases" Journal of Ocular Pharmacology and Therapeutics, 2013, vol. 29, No. 10, pp. 844-854.*
International Search Report and Written Opinion for PCT/US2014/017076 mailed May 5, 2014.
International Preliminary Report on Patentability for PCT/US2014/017076 mailed Sep. 3, 2015.
Extended European Search Report for European Application No. 14754427.4 mailed Aug. 8, 2016.
Frank et al. 2005, ABCB5-mediated doxorubicin transport and chemoresistance in human malignant melanoma. Cancer Research. 65:10;4320-4333.
Frank et al., ABCB5 P-glycoprotein is a molecular marker of the Hoechst 33342 side population phenotype among human fetal skeletal muscle cells. FASEB Journal. 2004;18(4-5):A183. Abstract 144.9.
Frank et al., Immunomodulatory functions of mesenchymal stem cells. Lancet. May 1, 2004;363(9419):1411-2.
Frank et al., Regulation of progenitor cell fusion by ABCB5 P-glycoprotein, a novel human ATP-binding cassette transporter. J Biol Chem. Nov. 21, 2003;278(47):47156-65. Epub Sep. 7, 2003.
Frank et al., Specific MDR1 P-glycoprotein blockade inhibits human alloimmune T cell activation in vitro. J Immunol. Feb. 15, 2001;166(4):2451-9.
Frank et al., VEGFR-1 expressed by malignant melanoma-initiating cells is required for tumor growth. Cancer Res. Feb. 15, 2011;71(4):1474-85. Epub Jan. 6, 2011.
Frassoni et al., Cord blood transplantation provides better reconstitution of hematopoietic reservoir compared with bone marrow transplantation. Blood. Aug. 1, 2003;102(3):1138-41. Epub Apr. 10, 2003.
Goodell et al., Isolation and functional properties of murine hematopoietic stem cells that are replicating in vivo. J Exp Med. Apr. 1, 1996;183(4):1797-806.
Guerci et al., Predictive value for treatment outcome in acute myeloid leukemia of cellular daunorubicin accumulation and P-glycoprotein expression simultaneously determined by flow cytometry. Blood. Apr. 15, 1995;85(8):2147-53.
Hierner et al., Skin grafting and wound healing-the "dermato-plastic team approach". Clin Dermatol. Jul.-Aug. 2005;23(4):343-52.
Jorgensen et al., Engineering mesenchymal stem cells for immunotherapy. Gene Ther. May 2003;10(10):928-31.
Kim et al., Identification of human ABCB5(+) dermal progenitor cells with multipotent differentiation plasticity. Apr. 1, 2010;130(Suppl 1):S107. Abstract.
Kleffel et al., ABCB5 inhibition sensitizes Merkel cell carcinoma cells to chemotherapy-induced apoptosis. J Invest Dermatol. 2014;134:S18. Meeting abstract.
Kobayahsi et al., in vitro response of the bone marrow-derived mesenchymal stem cells seeded in a type-I collagen-glycosaminoglycan scaffold for skin wound repair under the mechanical loading condition. Mol Cell Biomech. Dec. 2009;6(4):217-27.
Ma et al., Reconstruction of chemically burned rat corneal surface by bone marrow-derived human mesenchymal stem cells. Stem Cells. Feb. 2006;24(2):315-21. Epub Aug. 18, 2005.
Meier et al., Progressive decrease in No. And change in niche preference of the ABCB5(+) mesenchymal stem cell subset in the skin during aging. Sep. 1, 2010;130(Suppl. 2):S88. Abstract.
Menke et al., Expression analysis of multidrug efflux pump genes in mouse hematopoietic stem and progenitor cells. Blood. 1999;94(10)(Supp 1, Part 1):Abstract #132.
Pendse et al., P-Glycoprotein Functions as a Differentiation Switch in Antigen Presenting Cell Maturation. Am J Transplant Dec. 2008; 6(12):2884-93.
Rama et al., Limbal stem-cell therapy and long-term corneal regeneration. N Engl J Med. Jul. 8, 2010;363(2):147-55. doi: 10.1056/NEJMoa0905955. Epub Jun. 23, 2010.
Schatton et al., The Chemoresistance Mediator ABCB5 Identifies Melanoma Stem Cells. 14th SPORE Investigator's Workshop. 2006:92. Abstract 150.
Schatton et al., ABCB5 Identifies Immunoregulatory Dermal Cells. Cell Rep. Sep. 8, 2015;12(10):1564-74. doi: 10.1016/j.celrep.2015.08.010.
Schlötzer-Schrehardt et al., Identification and characterization of limbal stem cells. Exp Eye Res. Sep. 2005;81(3):247-64.
Setia et al., Profiling of ABC transporters ABCB5, ABCF2 and nestin-positive stem cells in nevi, in situ and invasive melanoma. Mod Pathol. Aug. 2012;25(8):1169-75. doi: 10.1038/modpathol.2012.71. Epub May 4, 2012.
Sharom, The P-glycoprotein efflux pump: how does it transport drugs? J Membr Biol. Dec. 1, 1997;160(3):161-75.
Shi et al., Transplantation of dermal multipotent cells promotes the hematopoietic recovery in sublethally irradiated rats. J Radiat Res (Tokyo). Mar. 2004;45(1):19-24.
Taipalensuu et al., Correlation of gene expression of ten drug efflux proteins of the ATP-binding cassette transporter family in normal human jejunum and in human intestinal epithelial Caco-2 cell monolayers. J Pharmacol Exp Ther. Oct. 2001;299(1):164-70.
Thill et al., Expression of CD133 and other putative stem cell markers in uveal melanoma. Melanoma Res. Oct. 2011;21(5):405-16.
Vrana et al., Development of a reconstructed cornea from collagen-chondroitin sulfate foams and human cell cultures. Invest Ophthalmol Vis Sci. Dec. 2008;49(12):5325-31. doi: 10.1167/iovs.07-1599. Epub Aug. 15, 2008.
Wilson et al., ABCB5 identifies a therapy-refractory tumor cell population in colorectal cancer patients. Cancer Res. Aug. 1, 2011;71(15):5307-16. Epub Jun. 7, 2011.
Young et al., Adult-derived stem cells and their potential for use in tissue repair and molecular medicine. J Cell Mol Med. Jul.-Sep. 2005;9(3):753-69.
Young et al., Human pluripotent and progenitor cells display cell surface cluster differentiation markers CD10, CD13, CD56, and MHC class-I. Proc Soc Exp Biol Med. May 1999;221(1):63-71.
Zhong et al., Tissue scaffolds for skin wound healing and dermal reconstruction. Wiley Interdiscip Rev Nanomed Nanobiotechnol. Sep.-Oct. 2010;2(5):510-25. doi: 10.1002/wnan.100.

* cited by examiner

```
                            SEQUENCE LISTING

<160> NUMBER OF SEQ ID NOS: 20

<210> SEQ ID NO 1
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 1
gttgagggga gcagccagag caaggtgaga aaggtg                              36

<210> SEQ ID NO 2
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 2
ttaagggtta ttgaatatga tcggaattgg gctgcaggaa tt                       42

<210> SEQ ID NO 3
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 3
tggggcagga cagcaagggg gaggat                                         26

<210> SEQ ID NO 4
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 4
ctggtccctc tcctgtgatc tacacaggcc                                     30

<210> SEQ ID NO 5
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 5
ggaagacaat agcaggcatg ctggg                                          25

<210> SEQ ID NO 6
<211> LENGTH: 25
<212> TYPE: DNA
<213> ORGANISM: Artificial Sequence
```

```
<220> FEATURE:
<223> OTHER INFORMATION: Synthetic oligonucleotide

<400> SEQUENCE: 6
ggctggggca actgaaaagt agcat                                          25

<210> SEQ ID NO 7
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 7
tttcagcttc agtttatcac aatgtgggtt                                     30

<210> SEQ ID NO 8
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 8
acttggtgcg gtgactctga attttgc                                        27

<210> SEQ ID NO 9
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 9
tagcaacatt tctggcattt taggctg                                        27

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 10
ggctggggca actgaaaagt agcat                                          25

<210> SEQ ID NO 11
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 11
gcaaatgtgt actctgcgct tatttaatg                                      29

<210> SEQ ID NO 12
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 12
tggtgcagac tacagacgtc agtgg                                          25
```

```
<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
gtgtctgggt ttcatccatc                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
aatgcggcat cttcaacctc                                              20

<210> SEQ ID NO 15
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 15
cagcgctctg ccgcctat                                                18

<210> SEQ ID NO 16
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 16
catgaccaac acagatcaaa catcc                                        25

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
gaagccgagg gcgattactg                                              20

<210> SEQ ID NO 18
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 18
gtgcttgtga tttggagtct gtcac                                        25

<210> SEQ ID NO 19
<211> LENGTH: 19
<212> TYPE: DNA
<213> ORGANISM: Artificial Sequence
<220> FEATURE:
<223> OTHER INFORMATION: Synthetic oligonucleotide
```

```
<400> SEQUENCE: 19
tcctagcacc atgaagatc                                                  19

<210> SEQ ID NO 20
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 20
aaacgcagct cagtaacag                                                  19
```

US 9,801,912 B2

ABCB5(+) STEM CELLS FOR TREATING OCULAR DISEASE

RELATED APPLICATIONS

The application is a national stage filing under U.S.C. §371 of PCT International Application PCT/US2014/017076, entitled "ABCB5(+) STEM CELLS FOR TREATING OCULAR DISEASE" filed on Feb. 19, 2014, which claims priority under 35 U.S.C. §119(e) of U.S. provisional application No. 61/766,424, filed Feb. 19, 2013, which are herein incorporated by reference in their entirety.

FEDERALLY SPONSORED RESEARCH

This invention was made with government support under 5R01CA113796 awarded by the National Institutes of Health and the National Cancer Institute. The government has certain rights in the invention.

BACKGROUND OF INVENTION

Limbal stem cells have been identified as slow-cycling, label-retaining cells in mice. Limbal stem cells express the nuclear transcription factor ΔNp63α in humans and lack expression of corneal epithelial differentiation markers such as KRT12 [2,8] (FIG. 1A). Limbal stem cells generate transient amplifying cells, which express the eye development master regulator PAX6 [9] and, during corneal development and regeneration, migrate out of the limbus to give rise to the KRT12(+) central corneal epithelium [10].

SUMMARY OF INVENTION

The present invention, in some aspects, is directed generally to the use of ABCB5(+) stem cells (e.g., human stem cells) for the treatment of ocular conditions such as, for example, corneal diseases and/or retinal diseases. The invention is based, in part, on the discovery that ABCB5 is expressed in stem cells of the eye, such ABCB5(+) stem cells are required for normal eye development, and when administered to subjects having ocular wounds (e.g., ocular surface wounds), these cells are capable of cell regeneration. For example, ABCB5(+) limbal stem cells, required for normal corneal development, are capable of corneal regeneration. Similarly, ABCB5(+) retinal pigment epithelium (RPE) cells, required for normal retinal development, are capable of retinal regeneration.

Thus, in some aspects of the invention, provided herein are methods of treating a subject having an ocular condition, comprising administering to the subject isolated ABCB5(+) stem cells in an amount effective to regenerate ocular cells in the subject.

In some embodiments, the ocular condition is a corneal disease. In some embodiments, the corneal disease is blindness due to limbal stem cell deficiency (LSCD). "Limbal stem cell deficiency" herein refers to severe or total, unilateral or partial LSCD [5]. In some embodiments, isolated ABCB5(+) limbal stem cells are administered to a subject to treat a corneal disease.

In some embodiments, the ocular condition is a retinal disease. In some embodiments, the retinal disease is macular degeneration. In some embodiments, the retinal disease is retinitis. In some embodiments, isolated ABCB5(+) retinal stem cells (e.g., ABCB5(+) RPE stem cells) are administered to a subject to treat a corneal disease.

In some embodiments, the ocular condition is an ocular wound.

In some embodiments, the isolated ABCB5(+) stem cells are administered as an ocular graft. In some embodiments, the ocular grafts contain one to about $10^7$ isolated ABCB5(+) stem cells. In some embodiments, more than $10^7$ isolated ABCB5(+) stem cells may be administered as an ocular graft.

In other aspects of the invention, provided herein are methods of isolating limbal stem cells from a mixed population of ocular cells, the methods comprising providing a mixed population of ocular cells and isolating ABCB5(+) limbal stem cells from the mixed population.

In yet other aspects of the invention, provided herein are methods of identifying the number of ABCB5(+) limbal stem cells in the ocular graft, comparing the number of ABCB5(+) limbal stem cells to the total cell population of the graft, and based on the comparison, selecting the ocular graft for transplantation.

In some embodiments, the methods comprise contacting cells of the mixed population with an antibody that selectively binds to human ABCB5.

In still other aspects of the invention, provided herein are methods of producing ocular grafts for transplantation to a subject, the methods comprising seeding a substrate with isolated ABCB5(+) stem cells to produce the ocular graft.

In some embodiments, the substrate comprises fibrin gel, amniotic membrane, aminoglycans, or a combination thereof. In some embodiments, the substrate is an artificial cornea. In such embodiments, the substrate, for example, an artificial cornea, comprises acellular collagen.

In some aspects of the invention, provided herein are ocular grafts enriched with isolated ABCB5(+) stem cells for transplantation in a subject.

In still other aspects of the invention, provided herein are methods of promoting ocular cell regeneration, comprising identifying limbal stem cells as ABCB5(+) limbal stem cells and administering to a subject in need thereof the ABCB5(+) limbal stem cells in an amount effective to promote ocular cell regeneration.

In further aspects of the invention, provided herein are isolated preparations of limbal stem cells characterized by the expression of ABCB5 on the cell surface.

In some embodiments, the isolated ABCB5(+) limbal stem cells are administered as an ocular graft.

In some embodiments, the subject is administered one to about $10^7$ isolated ABCB5(+) limbal stem cells by grafting.

In some embodiments, the isolated ABCB5(+) stem cells are isolated ABCB5(+) human stem cells.

In some embodiments, the isolated ABCB5(+) stem cells are allogeneic stem cells. In some embodiments, the isolated ABCB5(+) stem cells are syngeneic stem cells.

In some embodiments, the isolated ABCB5(+) stem cells are ABCB5(+) ocular stem cells. In some embodiments, the isolated ABCB5(+) ocular stem cells are isolated ABCB5(+) limbal stem cells. In some embodiments, the isolated ABCB5(+) limbal stem cells are isolated ABCB5(+) human limbal stem cells.

In some embodiments, the isolated ABCB5(+) stem cells are not skin stem cells (e.g., mesenchymal stem cells).

In some embodiments, the isolated ABCB5(+) stem cells are expanded ex-vivo prior to the administering step.

In some embodiments, the subject is a mammal. In some embodiments, the mammal is a human.

In some aspects of the invention, provided herein are kits that include a container housing any of the foregoing grafts or stem cell preparations and instructions for administering the graft or preparation to a subject in need thereof.

Use of a graft or stem cell preparation of the invention for treating an ocular condition is also provided as an aspect of the invention.

A method for manufacturing a medicament of a stem cell preparation of the invention for treating an ocular condition is also provided.

This invention is not limited in its application to the details of construction and the arrangement of components set forth in the following description or illustrated in the drawings. The invention is capable of other embodiments and of being practiced or of being carried out in various ways. Each of the above embodiments and aspects may be linked to any other embodiment or aspect. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

The accompanying drawings are not intended to be drawn to scale. For purposes of clarity, not every component may be labeled in every drawing. In the drawings:

FIG. 2C, right panel, shows Western blots of murine protein lysates with ABCB5 monoclonal antibody (mAb) 3C2-1D12, which revealed loss of a 80 kD protein band of predicted size in Abcb5 KO mice.

In FIGS. 4A and 4B, recipient mice received fibrin gel grafts containing no donor cells (rows 2, respectively), ABCB5(−) cells (rows 3, respectively), unsegregated limbal epithelial cells (rows 4, respectively), or ABCB5(+) cells (rows 5, respectively). As a reference, normal untreated (without induced LSCD) C57BL/6 and NSG murine corneas are shown in rows 1 of FIG. 4A and FIG. 4B, respectively. Corneal transparency was evaluated by slit lamp examination (FIG. 4A, 4B, columns 1). Epithelial integrity and regeneration were evaluated by H&E staining (columns 2—20× magnification; columns 3—40× magnification) for epithelial thickness and stratification, by periodic acid-Schiff staining (PAS) for detection Goblet cells associated with neovascularization (FIG. 4A, column 4), and Krt12 staining (green) for detection of differentiated corneal epithelial cells (FIG. 4A, 4B, columns 5). Nuclei are stained with DAPI (red). Bar graphs on the right show the percentages of murine KRT12(+) cells (FIG. 4A) or human KRT12(+) cells (FIG. 4B) in recipient corneas 5 weeks after transplantation. The right lower panel in (FIG. 4B) shows RT-PCR analyses of murine eyes transplanted with human cells for evaluation of human donor cell contribution to corneal repair.

DETAILED DESCRIPTION

Figure 1A:
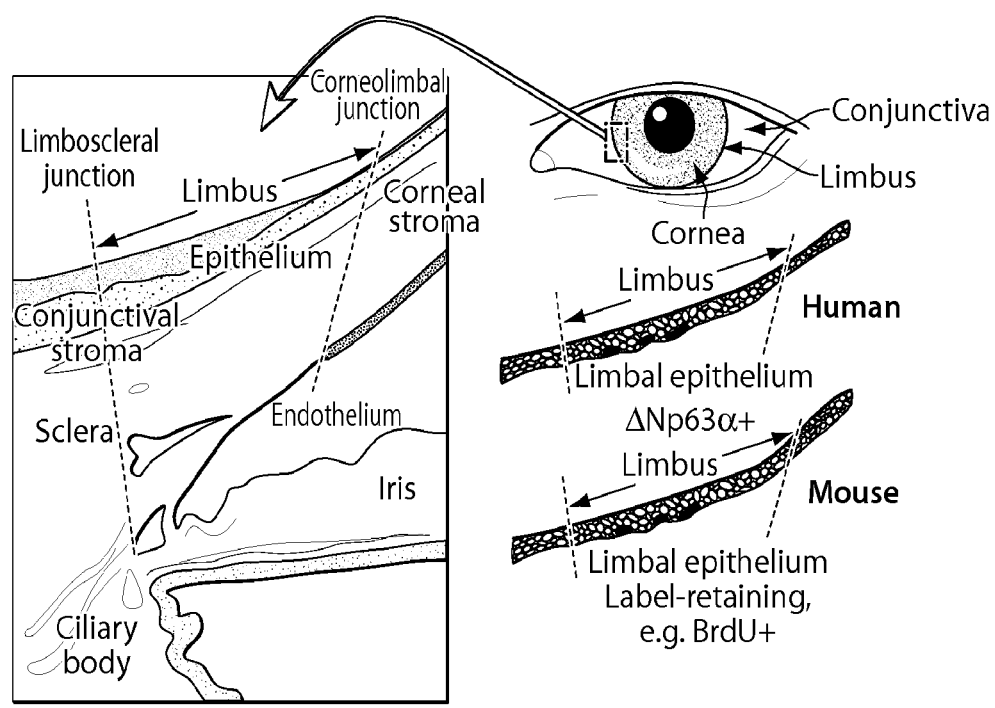
FIG. 1A shows a schematic illustration of corneal structures and the limbal stem cell niche.

Corneal epithelial homeostasis and regeneration are sustained by a population of limbal stem cells (LSCs) residing in the basal limbal epithelium of the eye [1-3]. These cells generate new corneal cells to replace damaged ones, and loss of LSCs due to injury or disease is a major cause of blindness worldwide [4]. Transplantation of LSCs from a healthy eye is often the only therapeutic option available to patients with LSCD. Transplant success depends foremost on the frequency of LSCs within grafts [5]. However, prior to the present invention, a limbal stem cell gene that permits prospective enrichment of this cell subset had not been reported [5].

The present invention is based, in part, on the findings that ATP-binding cassette, sub-family B (MDR/TAP), member 5 (ABCB5) [6,7] marks LSCs and is required for limbal stem cell maintenance, corneal development and repair, and that ABCB5-positive (ABCB5 (+)) LSCs prospectively isolated from donors possess the exclusive capacity to restore the cornea upon grafting. Thus, various aspects and embodiments of the invention are directed to methods of treating a subject having an ocular condition, methods of isolating ABCB5(+) stem cells of the eye, methods of selecting and/or producing ocular grafts for transplantation, and methods of promoting ocular cell regeneration as well as to grafts and preparations containing isolated ocular stem cells characterized by the expression of ABCB5 on their cell surface.

The inventors of the present invention demonstrate herein that ABCB5 is uniformly expressed on in vivo label-retaining LSCs in wild type mice and on ΔNp63α-positive LSCs in healthy humans. Consistent with these findings, the inventors also demonstrate that ABCB5-positive limbal stem cell frequency is significantly reduced in LSCD patients. ABCB5 loss of function studies using newly generated Abcb5 knockout (KO) mice caused depletion of quiescent LSCs due to enhanced proliferation and apoptosis and resulted in defective corneal differentiation and wound healing, which explains the demonstrated capacity of ABCB5(+) LSCs to restore the cornea. Results from murine gene KO, in vivo limbal stem cell tracing and limbal stem cell transplantation models, and concurrent findings in phenotypic and functional transplant analyses of human biopsy specimens, provide converging lines of evidence that ABCB5 identifies mammalian LSCs. Identification and prospective isolation of molecularly defined LSCs with essential functions in corneal development and repair has important implications for the treatment of corneal disease, particularly corneal blindness due to LSCD.

"ABCB5(+) stem cells," as used herein, refers to cells having the capacity to self-renew and to differentiate into mature cells of multiple adult cell lineages. These cells are characterized by the expression of ABCB5 on the cell surface. In some embodiments of the invention, ABCB5(+) stem cells are limbal stem cells. In some embodiments of the invention, ABCB5(+) stem cells are retinal stem cells. ABCB5(+) stem cells may be obtained from (e.g., isolated from or derived from) the basal limbal epithelium of the eye or from the retinal pigment epithelium (RPE). In some embodiments, ABCB5(+) stem cells are obtained from human eye. Other ABCB5(+) stem cell types such as, for example, those obtained from the central cornea may be used in various aspects and embodiments of the invention.

Figure 14A:
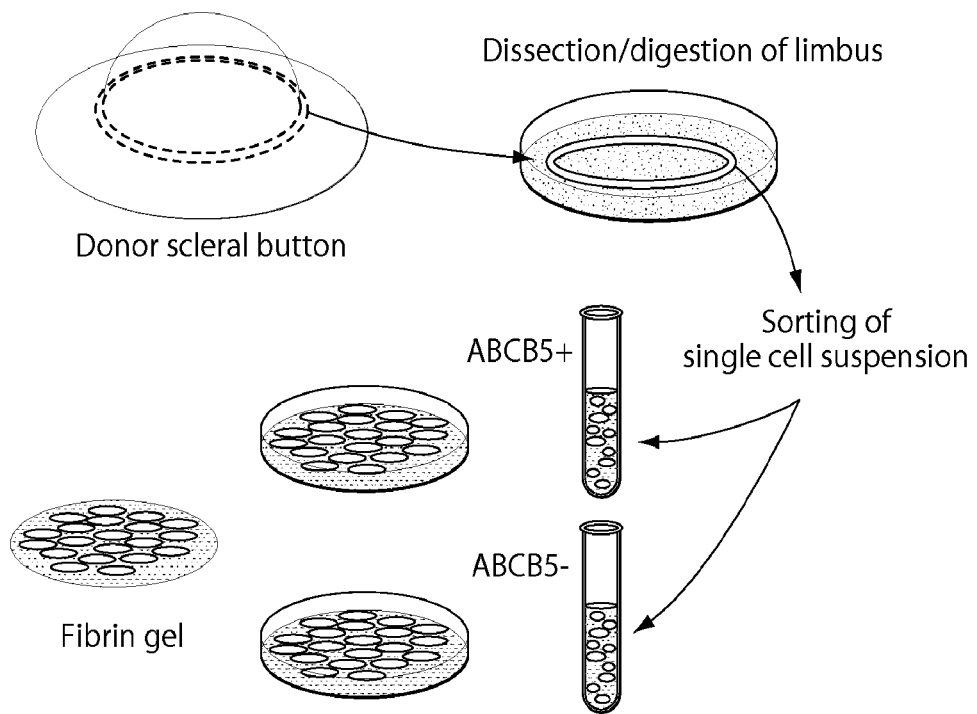
FIG. 14A shows a schematic illustration of the recovery and separation of ABCB5(+) and ABCB5(−) limbal epithelial cells from donor corneas followed by preparation of fibrin gels containing donor cells.
Figure 14B:
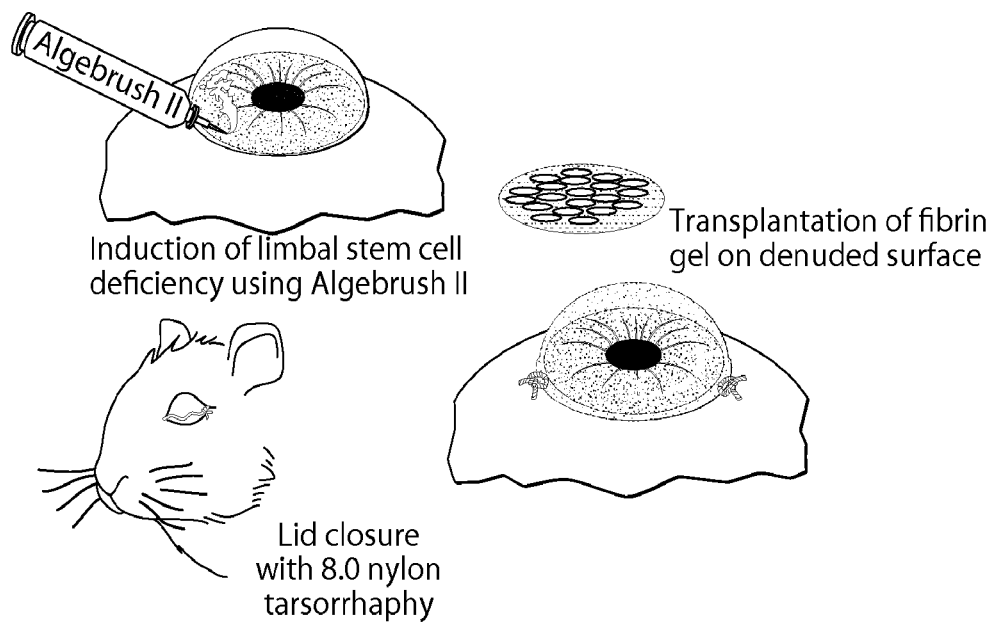
FIG. 14B shows a schematic illustration of induction of limbal stem cell deficiency in recipient mice and transplantation of donor grafts.

ABCB5(+) ocular stem cells may be obtained from a subject by isolating a sample of eye tissue, including ocular cells of the basal limbal epithelium or RPE, and then purifying the ABCB5(+) stem cells. It will be apparent to those of ordinary skill in the art that a sample can be enriched for ocular stems cells having ABCB5 in a number of ways. For example, ocular stems cells can be selected for through binding of ABCB5 on cell surface molecules with antibodies or other binding molecules. Ocular cells may be obtained directly from a donor or retrieved from cryopreservative storage. The ocular stems cells may, for instance, be isolated using antibodies against ABCB5 and maintained in culture using standard methodology or frozen, e.g., in liquid nitrogen, for later use. A non-limiting example of a method that may be used in accordance with the invention to obtain cells from the eye is described in the Examples section and is depicted in FIG. 14A.

The present invention contemplates any suitable method of employing ABCB5-binding molecules such as, for example, monoclonal antibodies, polyclonal antibodies, human antibodies, chimeric antibodies, humanized antibodies, single-chain antibodies, F(ab')2, Fab, Fd, Fv or single-chain Fv fragments to separate ABCB5(+) stem cells from a mixed population of ocular cells. Accordingly, included in the present invention is a method of producing a population of ABCB5(+) stem cells comprising the steps of providing a cell suspension of ocular cells; contacting the cell suspension with a monoclonal antibody, or a combination of monoclonal antibodies, which recognize(s) an epitope, including ABCB5, on the ABCB5(+) LSCs; and separating and recovering from the cell suspension the cells bound by the monoclonal antibodies. The monoclonal antibodies may be linked to a solid-phase and utilized to capture limbal stem cells from eye tissue samples. The bound cells may then be separated from the solid phase by known methods depending on the nature of the antibody and solid phase.

"Monoclonal antibody," as used herein, refers to an antibody obtained from a single clonal population of immunoglobulins that bind to the same epitope of an antigen. Monoclonal based systems appropriate for preparing cell populations of the invention include magnetic bead/paramagnetic particle column utilizing antibodies for either positive or negative selection; separation based on biotin or streptavidin affinity; and high speed flow cytometric sorting of immunofluorescent-stained LSCs mixed in a suspension of other cells. Thus, the methods of the present invention include the isolation of a population of LSCs and enhancement using monoclonal antibodies raised against surface antigen ABCB5 (e.g., monoclonal antibodies that selectively bind ABCB5). In some instances, commercially available antibodies or antibody fragments that selectively bind ABCB5 may be used in the methods disclosed herein. Such antibodies are considered to selectively bind to ABCB5 if they bind or are capable of binding to ABCB5 with a greater affinity that the affinity with which the monoclonal antibodies may bind to other antigens (i.e., antigens other than ABCB5). Such binding may be measured or determined by standard protein-protein interaction assays (e.g., antibody-antigen or ligand-receptor assays) such as, for example, competitive assays, saturation assays or standard immunoassays including, without limitation, enzyme-linked immunosorbent assays, radioimmunoassays and radio-immunofilter binding assays.

The ABCB5(+) stem cells (e.g., ABCB5(+) LSCs) may be isolated. An "isolated ABCB5(+) stem cell," as used herein, refers to a cell that has been removed from an organism in which it was originally found, or a descendant of such a cell. An isolated cell also refers to a cell that is placed into conditions other than the natural environment. Such a cell may later be introduced into a second organism or re-introduced into the organism from which it (or the cell or population of cells from which it descended) was isolated. Such a cell, once manipulated according to the methods of the invention is still considered to be an isolated cell. The term "isolated" does not preclude the later use of the cell thereafter in combinations or mixtures with other cells or in an in vivo environment.

"Compositions," herein, may refer to an isolated cell preparations or grafts, including tissue grafts and artificial grafts (e.g., acellular collagen grafts). The compositions of the invention, in some instances, are enriched with isolated ABCB5(+) stem cells. A composition is considered to be enriched with isolated ABCB5(+) stem cells if the ABCB5(+) stem cells are the predominant cell subtype present in the preparation. For example, an ABCB5(+) stem cell-enriched composition is a composition in which at least 50%, at least 55%, at least 60%, at least 65%, at least 70%, at least 75%, at least 80%, at least 85%, at least 90%, at least 95%, at least 98%, at least 99% or 100% of the cells of the composition are ABCB5(+) stem cells (e.g., ABCB5(+) LSCs). In some embodiments, a composition enriched with isolated ABCB5(+) stem cells is one in which less than 50%, less than 45%, less than 40%, less than 35%, less than 30%, less than 25%, less than 20%, less than 15%, less than 10%, less than 9%, less than 8%, less than 7%, less than 6%, less than 5%, less than 4%, less than 3%, less than 2% or less than 1% of the cells of the composition are ABCB5(−) cells. In some embodiments, the cells of a composition are only ocular cells. That is, in some embodiments, a composition may not contain non-ocular cells. In some embodiments, a composition may not contain ABCB5(−) cells.

The ABCB5(+) stem cells (e.g., ABCB5(+) LSCs) may be prepared as substantially pure preparations. The term "substantially pure," as used herein, refers to a preparation that is substantially free of cells other than ABCB5(+) stem cells (e.g., ABCB5(+) LSCs). For example, a substantially pure preparation of ABCB5(+) stem cells may constitute a preparation in which at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% percent of the total cells present in a preparation are ABCB5(+) stem cells (e.g., ABCB5(+) LSCs).

In some embodiments, isolated and/or substantially pure ABCB5(+) cell preparations may be packaged in a finished pharmaceutical container such as an injection vial, ampoule, or infusion bag along with any other components that may be desired, e.g., agents for preserving cells or reducing bacterial growth. The cell preparation may be in unit dosage form.

The ABCB5(+) stem cells (e.g., ABCB5(+) LSCs) are useful for treating ocular conditions. In some embodiments, the ocular condition is an ocular wound, which may lead to ocular scarring, which in turn may cause decreased vision or blindness. In some embodiments, the ABCB5(+) stem cells (e.g., ABCB5(+) LSCs) may be used to treat corneal diseases such as, for example, blindness due to limbal stem cell deficiency (LSCD). In some embodiments, the ABCB5(+) stem cells (e.g., ABCB5(+) LSCs and/or ABCB5(+) RPE stem cells) may be used to treat retinal diseases such as, for example, macular degeneration or retinitis/retinitis pigmentosa. Macular degeneration refers to a group of conditions that includes a deterioration of the macula causing a loss of central vision needed for sharp, clear eyesight. It is a leading cause of vision loss and blindness in those 65 years of age and older. Macular degeneration may also be referred to as AMD or ARMD (age-related macular degeneration). Retinitis refers to inflammation of the retina, which may lead to blindness. Retinitis pigmentosa, which may be the result of a genetic condition or an inflammatory response, refers to a group of inherited disorders characterized by progressive peripheral vision loss and night vision difficulties (nyctalopia) that can lead to central vision loss.

The isolated ABCB5(+) stem cells (e.g., ABCB5(+) LSCS and/or ABCB5(+) RPE stem cells) may be administered to a subject in need thereof in an amount effective to regenerate ocular cells in the subject (referred to herein as an "effective amount" of ABCB5(+) stem cells). In some embodiments, one to about $10^7$ ABCB5(+) stem cells are administered to a subject. In some embodiments, a single isolated ABCB5(+) stem cell is administered to a subject. In some embodiments, about $10^1$ to about $10^7$, about $10^1$ to about $10^6$, about $10^1$ to about $10^5$, about $10^1$ to about $10^4$, about $10^1$ to about $10^3$, about $10^1$ to about $10^2$ isolated ABCB5(+) stem cells are administered to a subject. In some embodiments, about $10^1$, $10^2$, $10^3$, $10^4$, $10^5$, $10^6$, $10^7$ or more isolated ABCB5(+) stem cells are administered to a subject. In some embodiments, less than about $10^1$ isolated ABCB5(+) stem cells are administered to a subject.

In some embodiments, the isolated ABCB5(+) stem cells (e.g., as a composition in the form of an ABCB5(+) stem cell preparation or graft) may be administered to a subject more than once. Thus, in some embodiments, a subject may be administered multiple doses or grafts (e.g., 2, 3, 4 or more) of isolated ABCB5(+) stem cells over the course of several weeks, months or years. In some embodiments, the stem cells are administered again 3 months, 6 months, 9 months, 12 months, 18 months, 21 months or 24 months after the first application. The number of applications and frequency of application may depend, for example, on the degree of cellular regeneration achieved after the first stem cell administration/transplantation. The number and frequency of stem cell applications may be determined by a medical professional (e.g., surgeon, physician).

In some embodiments, a subject having an ocular condition has an ocular wound (e.g., dead, damaged or infected ocular cells) in, for example, the corneal epithelium. Thus, the corneal epithelium may be wounded in a subject having an ocular condition in accordance with the invention. It has been discovered that ABCB5(+) limbal stem cell grafts can be used to restore the cornea. Thus, in some embodiments, the integrity of the corneal epithelial surface of the subject is restored following administration of an effective amount of ABCB5(+) LSCs. Corneal regeneration may be assessed based on, for example, corneal transparency (e.g., development of clear, rather than opaque, cornea) and/or visual acuity. Methods of assessing the success of ocular cell/stem cell transplantation (e.g., extent of cellular regeneration, visual acuity) are known in the art, any of which may be used in accordance with the invention. Examples of methods for assessing success of a ocular cell/stem cell transplantation include, without limitation, slit lamp imaging, Heidelberg retina tomography (HRT), optical coherence tomography (OCT) and 2-photon imaging. Other examples include, without limitation, the use of Rose Bengal (4,5,6,7-tetrachloro-2',4',5',7'-tetraiodofluorescein) dye and other epithelial staining solutions.

The ABCB5(+) stem cells (e.g., ABCB5(+) LSCS) may be autologous to the subject (obtained from the same subject) or non-autologous such as cells that are allogeneic or syngeneic to the subject. Alternatively, the ABCB5(+) stem cells (e.g., ABCB5(+) LSCS) may be obtained from a source that is xenogeneic to the subject.

Allogeneic refers to cells that are genetically different although belonging to or obtained from the same species as the subject. Thus, an allogeneic human ABCB5(+) limbal stem cell is a limbal stem cell obtained from a human other than the intended recipient of the limbal stem cells. Syngeneic refers to cells that are genetically identical or closely related and immunologically compatible to the subject (i.e., from individuals or tissues that have identical genotypes). Xenogeneic refers to cells derived from or obtained from an organism of a different species than the subject.

The ABCB5(+) stem cells (e.g., ABCB5(+) LSCS) in accordance with the invention may be expanded ex-vivo prior to the administering step. Thus, in some instances, ABCB5 expression provides a basis for identifying, isolating, cloning, propagating, and expanding ABCB5(+) stem cells (e.g., ABCB5(+) LSCS) in vitro. The present invention contemplates any suitable method of employing agents, e.g., isolated peptides, e.g., antibodies, that bind to ABCB5 to separate ABCB5(+) stem cells from other cells. The isolated ABCB5(+) stem cells may be maintained in an appropriate culture environment using, for example, a combination of media, supplements and reagents. Optionally, feeder cell populations or conditioned media obtained from feeder cell populations may be used to expand the ABCB5(+) stem cell populations.

Adhesion, attachment and matrix factors that may be used for stem cell expansion in accordance with the invention include, without limitation, E-cadherin, collagen, fibronectin, superfibronectin, heparin sulfate proteoglycan, ICAM-I, laminin, osteopontin, proteoglycan, E-selectin, L-selectin, VCAM and vitronectin.

Bioactives and supplements that may be used for stem cell expansion in accordance with the invention include, without limitation, enzymes (e.g., cathepsin G, Flt-3/Fc), proteins and peptides (e.g., activin A, albumin, angiogenin, angiopoietin, BAX inhibiting peptide, heregulin beta-1, SMAC/Diablo), vitamins, hormones and various other substances (e.g., L-ascorbic acid, dexamethasone, EGF, EGF-receptor, embryonic fluid (bovine), flt3-ligand, progesterone, retinoic acid, retinyl acetate, thrombopoietin and TPO), antibodies, chemokines, cytokines, growth factors and receptors.

Culture reagents that may be used for stem cell expansion in accordance with the invention include, without limitation, antibiotics (e.g., cycloheximide, etoposide, gentamicin, mitomycin, penicillin-streptomycin), classical media (e.g., Claycomb Medium, Dulbecco's Modified Eagle Medium, Iscove's Modified Dulbecco's Medium, Minimum Essential Medium), cell freezing medium-DMSO, Claycomb Medium without L-glutamine, Stemline® Medium (Sigma-Aldrich, USA).

As used herein, a subject may be a mammal such as, for example, a human, non-human primate, cow, horse, pig, sheep, goat, dog, cat or rodent. Human ABCB5(+) stem cells (e.g., ABCB5(+) LSCs) and human subjects are particularly important embodiments.

Compositions of the present invention may comprise stem cells (e.g., limbal stem cells), or an isolated preparation of stem cells, the stem cells characterized by the expression of ABCB5 on their cell surface. A composition may comprise a preparation enriched with isolated ABCB5(+) stem cells (e.g., ABCB5(+) LSCs), or it may comprise a substantially pure population of ABCB5(+) stem cells (e.g., ABCB5(+) LSCs). Compositions are meant to encompass ocular grafts, discussed herein.

The compositions, in some embodiments, may comprises additional bioactives and supplements to promote cell regeneration and differentiation. Such bioactives and supplements that may be used in accordance with the invention are describe above and include, without limitation, various enzymes, proteins and peptides, vitamins, antibodies, chemokines, cytokines, growth factors and receptors. In some embodiments, the compositions may comprise an immunosuppressant and/or an anti-vasculogenesis agent. For example, in some embodiments, a composition may comprise cyclosporin (e.g., CyA), which may be used to prevent and/or treat graft rejections. In some embodiments, the compositions may comprise bevacizumab (e.g., AVASTIN®). The use of anti-vasculogenesis agent may be used, in some instances, to prevent blood vessel formation, which often occurs after transplantation and may lead to graft rejection. In some embodiments, an immunosuppressant and/or an anti-vasculogenesis agent is not administered as a component of a composition, but rather is administered independently prior to or subsequent to administration of ABCB5(+) stem cells.

In some embodiments, the compositions are formulated for topical administration. An example of a composition formulated for topical administration is an ocular graft. An ocular graft for transplantation in accordance with the invention refers to a substrate containing ACBC5(+) stem cells (e.g., ACBC5(+) LSCs) and optionally other ocular cells and bioactive factors (e.g., cytokines, growth factors) that promote ocular cell regeneration, which substrate may be transplanted to or implanted into an eye of a subject to replace damaged or infected tissue (e.g., to treat an ocular wound). An ocular graft may contain a mixed population of cells including ocular cells such as, for example, corneal and/or retinal cells. In some embodiments, an ocular graft for transplantation is enriched with ABCB5(+) LSCs.

The cornea is the transparent front part of the eye that covers the iris, pupil and anterior chamber. The cornea, with the anterior chamber and lens, refracts light, with the cornea accounting for approximately two-thirds of the eye's total optical power. The cornea of primates has five layers: corneal epithelium (multicellular epithelial tissue layer), Bowman's layer (condensed layer of collagen fibers), corneal stroma (middle layer of collagen fibers, e.g., collagen type I fibrils, and keratocytes), descemet's membrane (thin layer from which corneal epithelium cells are derived, composed of collagen type IV fibrils) and corneal endothelium (simple squamous or low cuboidal layer of mitochondria-rich cells). Compositions, including isolated preparations and ocular grafts, in accordance with the invention may comprise, in addition to ABCB5(+) stem cells, any one or more of the cell subtypes of the five corneal layers. In some embodiments, the compositions do not contain any one or more of the cell subtypes of the five corneal layers.

The retina is the light-sensitive layer of tissue lining the inner surface of the eye. The retina itself has several layers of neurons interconnected by synapses, including photoreceptor cells such as rods, cones and ganglion cells. Compositions, including isolated preparations and ocular grafts, in accordance with the invention may comprise, in addition to ABCB5(+) stem cells, any one or more of the neuronal cell subtypes of the retina, including retinal epithelial cells of the RPE. In some embodiments, the compositions do not contain any one or more of the neuronal cell subtypes of the retina.

The cells of a composition intended for use in transplantation (e.g., ocular graft) may be allogeneic or syngeneic. In some embodiments, the cells are not skin stem cells (e.g., mesenchymal stem cells). Thus, in some embodiments, the cells of a composition of the invention do not contain (i.e., exclude) ABCB5(+) mesenchymal stem cells.

In some embodiments, the compositions, including ocular grafts, are enriched with ABCB5(+) stem cells. In some embodiments, the ocular grafts are enriched with ABCB5(+) LSCs. In some embodiments, the ocular grafts are enriched with ABCB5(+) RPE stem cells. For example, an ocular graft is considered to be enriched ABCB5(+) LSCs if the ABCB5(+) limbal stem cell is the predominant cell subtype present in the graft. For example, an ocular graft is enriched with ABCB5(+) LSCs if the LSCs outnumber the other cell subtypes in the graft. In some embodiments, at least 50% of the cells of the graft are ABCB5(+) stem cells or ABCB5(+) limbal stem cells. For example, in some embodiments, at least 55%, at least 60%, at least 65%, at least 70%, at least 75%, at least 80%, at least 85%, at least 90%, at least 95%, at least 98%, at least 99% or 100% of the cells of the ocular graft are ABCB5(+) stem cells or ABCB5(+) limbal stem cells. In some embodiments, less than 15%, less than 10%, less than 5% or less than 1% of the cells of an ocular graft are ABCB5(−) cells.

The compositions of the invention may comprise a substrate such as, for example, a biocompatible material that promotes wound healing, including biodegradable scaffolds such as, for example, fibrin gel. Fibrin gels are typically prepared from fibrogen and thrombin, key proteins involved in blood clotting. Other examples of substrates that may be used in accordance with the invention include, without limitation, amniotic membrane, aminoglycan scaffolds, and adhesives. ABCB5(+) stem cells may be added to the substrate to form, for example, ocular grafts for transplantation.

Compositions of the invention may be transplanted to, for example, the surface of the cornea or the retina. Thus, in some embodiments, the compositions are administered topically. In instances where a stem cell graft is transplanted to the eye, the graft may be sutured in place. In other embodiments, the stem cell compositions are injected. In some embodiments, the compositions are injected intravenously, intraarterially or intravascularly. Other routes of administration are contemplated. It should be understood that the compositions and/or ABCB5(+) stem cells of the invention may be administered with or without a carrier. Thus, in some embodiments, a substantially pure population of isolated ABCB5(+) stem cells may be administered to a subject to, for example, treat an ocular condition.

ABCB5 expression may be used to select ocular cell preparations (e.g., grafts) for transplantation, thereby permitting the selection of ocular cell preparations enriched with ABCB5(+) stem cells. Such methods in accordance with the invention include identifying the number of ABCB5 (+) stem cells (e.g., ABCB5(+) limbal stem cells) in the ocular cell preparations, comparing the number of ABCB5 (+) stem cells to the total cell population of the cell preparations, and based on the comparison, selecting the ocular cell preparations for transplantation. The number of ABCB5 (+) stem cells in the ocular cell preparations may be identified using any one or more known molecules that selectively bind to ABCB5. For example, in some embodiments, ABCB5(+) stem cells may be identified by contacting the cells with an antibody or other binding molecule that selectively binds to ABCB5. Viable dyes (e.g., rhodamine or other stem cell marker dyes) may also be used to identify ABCB5(+) stem cells. ABCB5(+) stem cells also can be isolated based on the presence or absence of other specific markers of interest. For example, agents can be used to recognize stem cell-specific markers, for instance labeled antibodies that recognize and bind to cell-surface markers or antigens on stem cells can be used to separate and isolate ABCB5(+) stem cells using fluorescent activated cell sorting (FACS), panning methods, magnetic particle selection, particle sorter selection and other methods known to persons skilled in the art, including density separation. Typically, ocular cell preparations are selected for transplantation if they are enriched with ABCB5(+) stem cells (e.g., ABCB5 (+) limbal stem cells). Such ABCB5(+) enriched cell preparations increase the success of transplantation. In some embodiments, ocular cell preparations (e.g., grafts) may be selected for transplantation if at least 0.03% of the total cell population is ABCB5(+). In some embodiments, ocular cell preparations are selected for transplantation if at least 0.04%, at least 0.05%, at least 0.06%, at least 0.07%, at least 0.08%, at least 0.09%, at least 0.10%, at least 0.15%, at least 0.20%, at least 0.30%, at least 0.40%, at least 0.50%, at least 0.60%, at least 0.70%, at least 0.80%, at least 0.90%, at least 1.0%, at least 2.0%, at least 3.0%, at least 4.0%, at least 5.0%, at least 10.0%, at least 20.0%, at least 30.0%, at least 40.0%, at least 50.0%, at least 60.0%, at least 70.0%, at least 80%, at least 90%, at least 95%, at least 98%, at least 99%, at least 99.9% or 100% of the total cell population is ABCB5(+).

The ABCB5(+) stem cells of the invention may also be used to prepare/produce artificial grafts such as, for example, artificial corneal grafts. Such grafts may be made from acellular collagen or other acellular biocompatible material. In some embodiments, isolate ABCB5(+) stem cells are seeded onto an acellular matrix to produce an artificial graft such as, for example, an artificial cornea.

Compositions for topical administration such as, for example, an ocular graft may be administered by any means known in the art such as, for example, those described by Rama, J. et al [5].

An example of a method of the invention follows. ABCB5 (+) stem cells are obtained and cultured on fibrin gel (e.g., using lethally irradiated feeder cells, e.g., 3T3-J2 cells). A 360° limbal peritomy is performed and the fibrovascular corneal pannus carefully removed. The fibrin-cultured ABCB5(+) epithelial sheet is placed on the prepared corneal wound bed spanning the limbus (e.g., about 2-3 mm to reduce competition with conjunctival ingrowth). The conjunctiva is then sutured over the peripheral fibrin sheet with sutures (e.g., 8.0 vicryl sutures) to protect the border of the sheet and help it to adhere on the surface. The eyelids are kept closed (e.g., with STERI-STRIP™ (3M™ NEX-CARE™)) and patched for one week.

The invention also contemplates using the isolated ABCB5(+) stem cells (e.g., ABCB5(+) limbal stem cells or ABCB5(+) corneal stem cells) to produce totipotent, multipotent or pluripotent stem cells (e.g., induced pluripotent stem cells (iPSCs)), from which other cells, tissues and/or whole animals can develop. Thus, methods for directly reprogramming, or inducing, isolated ABCB5(+) stem cells to become totipotent, multipotent or pluripotent stem cells are provided in some aspects of the invention. The term "reprogramming," as used herein, refers to a process that reverses the developmental potential of a cell or population of cells (e.g., an isolated ABCB5(+) stem cell). Thus, reprogramming refers to a process of driving a cell to a state with higher developmental potential, i.e., backwards to a less differentiated state. The cell to be reprogrammed can be either partially or terminally differentiated prior to reprogramming. In some embodiments, reprogramming encompasses a complete or partial reversion of the differentiation state, i.e., an increase in the developmental potential of a cell, to that of a cell having a totipotent, multipotent or pluripotent state. In some embodiments, reprogramming encompasses driving an isolated ABCB5(+) stem cell to a totipotent, multipotent or pluripotent state, such that the cell has the developmental potential of an embryonic stem cell, i.e., an embryonic stem cell phenotype. Reprogramming also encompasses partial reversion of the differentiation state of a cell to a state that renders the cell more susceptible to complete reprogramming to a totipotent, multipotent or pluripotent state when subjected to additional manipulations.

Totipotent, multipotent or pluripotent stem cells may be generated from ABCB5(+) stem cells (referred to herein as "reprogrammed ABCB5(+) cells") using several reprogramming factors. The resultant cells, which have a greater developmental potential than the isolated ABCB5(+) stem cells, may then become the source of stem cells for further manipulations. A "reprogramming factor" as used herein, refers to a developmental potential altering factor, the expression of which contributes to the reprogramming of a cell, e.g., an isolated ABCB5(+) stem cell, to a less differentiated or undifferentiated state, e.g., to a cell of a pluripotent state or partially pluripotent state. Reprogramming factors include OCT4, SOX2, KLF 4 and c-MYC (otherwise known as the "Yamanaka factors" [32], incorporated herein by reference in its entirety). Other reprogramming factors include, without limitation, SOX 1, SOX 3, SOX15, SOX 18, NANOG, KLF1, KLF 2, KLF 5, NR5A2, LIN28, 1-MYC, n-MYC, REM2, TBX3, TERT and LIN28. Any combination of two or more of the foregoing transcription factors may be used to reprogram isolated ABCB5(+) stem cells. Methods of reprogramming cells to a totipotent, multipotent or pluripotent state are described by Stadtfeld and Hochedlinger [33], incorporated herein by reference in its entirety.

Reprogrammed ABCB5(+) cells may be used, in some embodiments of the invention, for basic and/or clinical applications, including disease modeling, drug toxicity screening/drug discovery, gene therapy and cell replacement therapy.

For example, reprogrammed ABCB5(+) cells may be used to treat a variety of conditions (e.g., genetic conditions) including, without limitation, sickle cell anemia, Parkinson's disease, hemophilia A, heart disease such as ischemic heart disease, Alzheimer's disease, spinal cord injury, stroke, burns, diabetes, osteoarthritis and rheumatoid arthritis.

In some embodiments, the reprogrammed ABCB5(+) cells may be used in organ transplantations to provide cell types that are genetically matched with a patient.

Other basic and clinical uses of the reprogrammed ABCB5(+) stem cells are contemplated.

Methods for producing differentiated cells from reprogrammed ABCB5(+) cells are also provided herein. The methods may comprise expressing in the reprogrammed ABCB5(+) cells any one or more differentiation factors necessary to promote differentiation into a more mature, differentiated cell type such as, for example, a blood cell, platelet, stromal cell, bone cell, muscle cell, skin cell, fat cell or neural cell. As used herein, the term "differentiation factor" refers to a developmental potential altering factor such as a protein, or small molecule that induces a cell to differentiate to a desired cell-type, e.g., a differentiation factor reduces the developmental potential of a cell. Differentiation to a specific cell type may involve simultaneous and/or successive expression of more than one differentiation factor. The methods may further comprise growing the reprogrammed ABCB5(+) cells under conditions for promoting differentiation to form a differentiated cell.

Thus, reprogrammed ABCB5(+) cells can be generated from isolated ABCB5(+) stem cells of the invention (e.g., isolated ABCB5(+) limbal stem cells or isolated ABCB5(+) RPE stem cells), and the reprogrammed ABCB5(+) cells can be differentiated into one or more desired cell types. A "stem cell" as used herein is an undifferentiated or partially differentiated cell that has the ability to self-renew and has the developmental potential to differentiate into multiple cell types. A "pluripotent cell" is a cell with the developmental potential, under different conditions, to differentiate to cell types characteristic of all three germ cell layers, i.e., endoderm (e.g., gut tissue), mesoderm (including blood, muscle, and vessels), and ectoderm (such as skin and nerve). A "multipotent" cell is a cell that has the developmental potential to differentiate into cells of one or more germ layers, but not all three. These cells include, for instance, adult stem cells, such as for example, hematopoietic stem cells and neural stem cells. A "totipotent" cell is a cell that has the developmental potential to differentiate into all the differentiated cells in an organism, including extraembryonic tissues. Stem cells may have a propensity for a differentiated phenotype; however, these cells can be induced to reverse and re-express the stem cell phenotype. This process is referred to as "dedifferentiation" or "reprogramming."

The isolated ABCB5(+) stem cells, reprogrammed ABCB5(+) cells and differentiated cells of the invention can be manipulated under standard conditions for these cell types. The treatment of the cells may be performed in vitro, ex vivo or in vivo. For instance, the cells may be present in the body or in a culture medium. The manipulations may be performed under high or low-oxygen conditions.

A "culture medium" contains nutrients that maintain cell viability and support proliferation. A typical culture medium includes: salts, buffers, amino acids, glucose or other sugar(s), antibiotics, serum or serum replacement, and/or other components such as peptide growth factors. Cell culture media for use in deriving and maintaining totipotent, multipotent and pluripotent cells are known in the art. Culture medium may also include cell specific growth factors, such as angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor-alpha, cytokine-induced neutrophil chemotactic factor 1, cytokine-induced neutrophil, chemotactic factor 2-alpha, cytokine-induced neutrophil chemotactic factor 2-beta, beta-endothelial cell growth factor, endothelia 1, epidermal growth factor, epithelial-derived neutrophil attractant, fibroblast growth factor 4, fibroblast growth factor 5, fibroblast growth factor 6 fibroblast growth factor 7, fibroblast growth factor 8, fibroblast growth factor b, fibroblast growth factor c, fibroblast growth factor 9, fibroblast growth factor 10, fibroblast growth factor acidic, fibroblast growth factor basic, glial cell line-derived neutrophil factor receptor-alpha-1, glial cell line-derived neutrophil factor receptor-alpha-2, growth related protein, growth related protein-alpha, growth related protein-beta, growth related protein-gamma, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor-alpha, nerve growth factor, nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor-alpha, platelet derived growth factor receptor-beta, pre-B cell growth stimulating factor, stem cell factor, stem cell factor receptor, transforming growth factor-alpha, transforming growth factor-beta, transforming growth factor-beta-1, transforming growth factor-beta-1-2, transforming growth factor-beta-2, transforming growth factor-beta-3, transforming growth factor-beta-5, latent transforming growth factor-beta-1, transforming growth factor-beta-binding protein I, transforming growth factor-beta-binding protein II, transforming growth factor-beta-binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

The differentiation state of the cell can be assessed using any methods known in the art for making such assessments. For instance, the differentiation state of a cell treated according to the methods described herein may be compared with an untreated cell or cells treated with DNA using viral vectors to deliver DNA resulting in the expression of the same reprogramming or differentiation factors.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

C57BL/6J, NOD.Cg-Prkdcscid Il2rgtmIWjl/SzJ (NSG), B6;SJL-Tg(ACTFLPe)9205Dym/J, and B6.FVB-Tg(EIIa-cre)C5379Lmgd/J mice were purchased from Jackson Laboratory (Bar Harbor, Me.). Abcb5 knockout (KO) mice were generated as described below. All animals were maintained in accordance with the Institutional Guidelines of Boston Children's Hospital and the Schepens Eye Research Institute, Harvard Medical School. Four to twelve weeks-old mice were used for the following experiments.

Example 1. ABCB5 is a Molecular Marker of Limbal Stem Cells (LSCs)

Figure 1B:
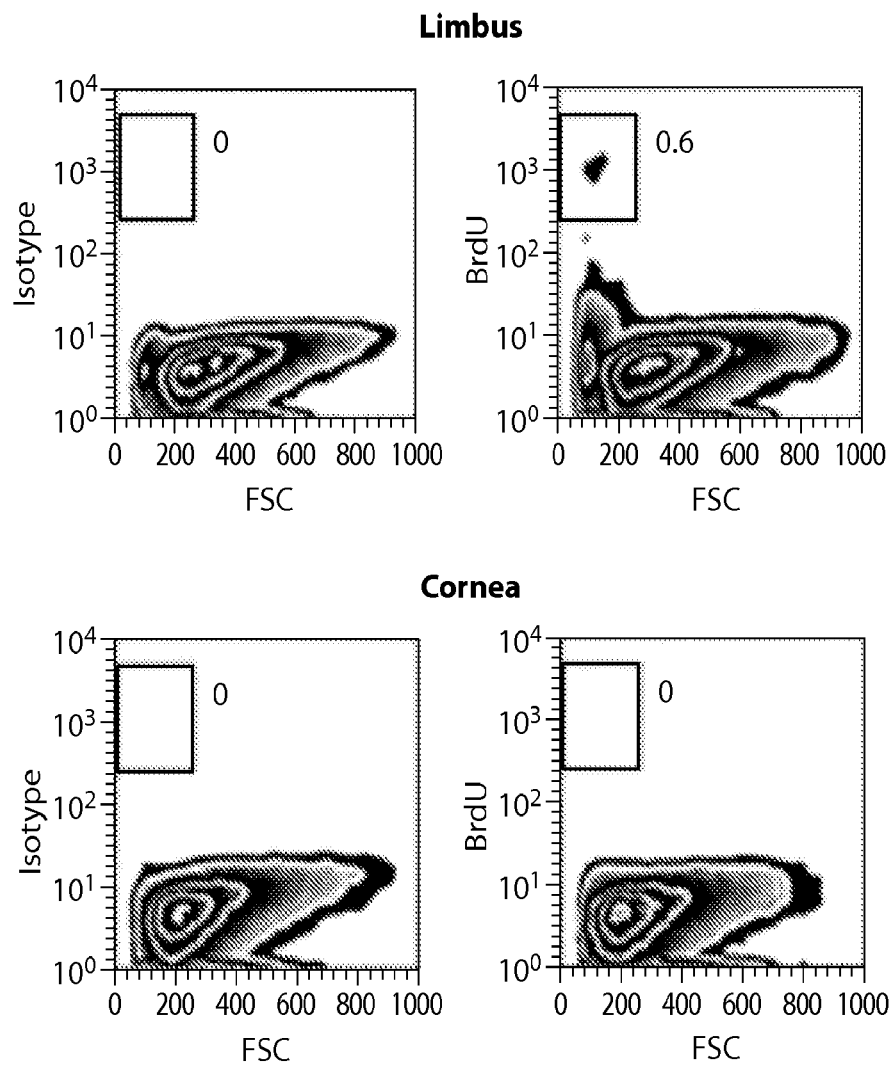
FIG. 1B shows representative flow cytometric analyses of BrdU-labeled dissociated murine corneal cells identifying the presence of a label-retaining cell population in the limbus.
Figure 1C:
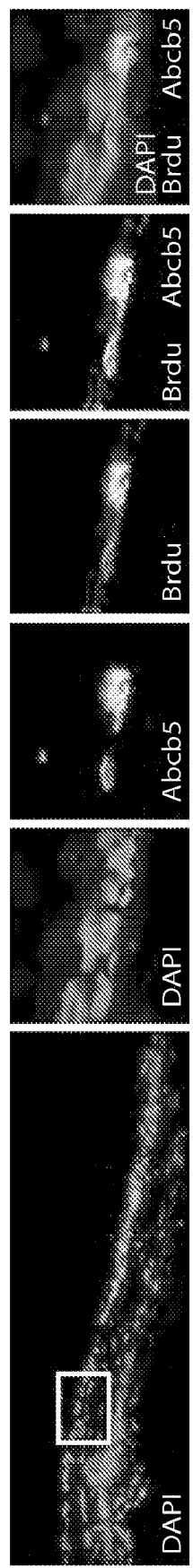
FIG. 1C shows immunofluorescence images depicting co-expression of ABCB5 and BrdU in murine limbus.
Figure 1D:
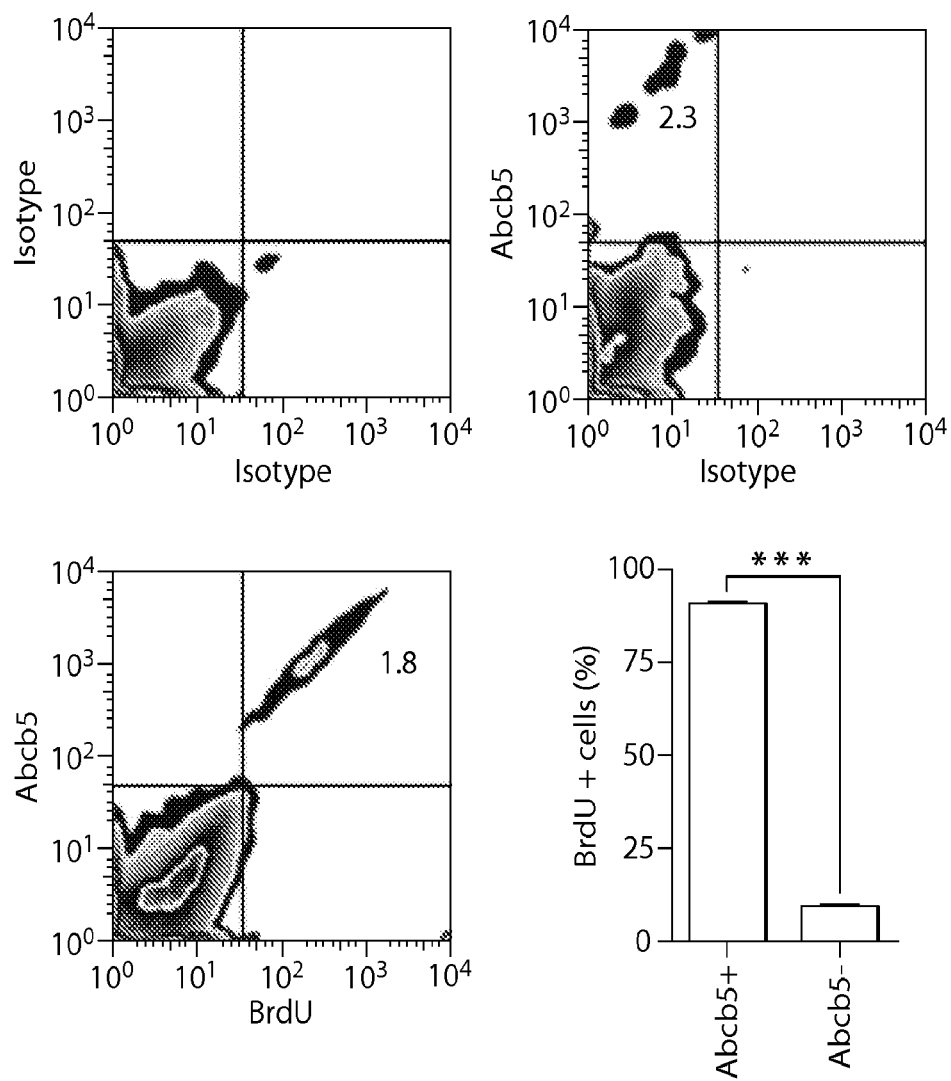
FIG. 1D shows representative flow cytometric analyses depicting co-expression of ABCB5 and BrdU in murine limbus. Bar graph (right) illustrates quantitative analysis of independent experiments (n=4).
Figure 5A:
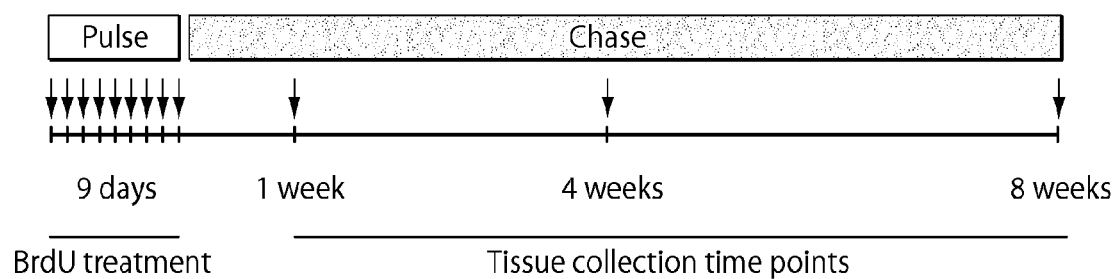
FIG. 5A shows a schematic summary of the experimental design for BrdU pulse-chase experiments.
Figure 5B:
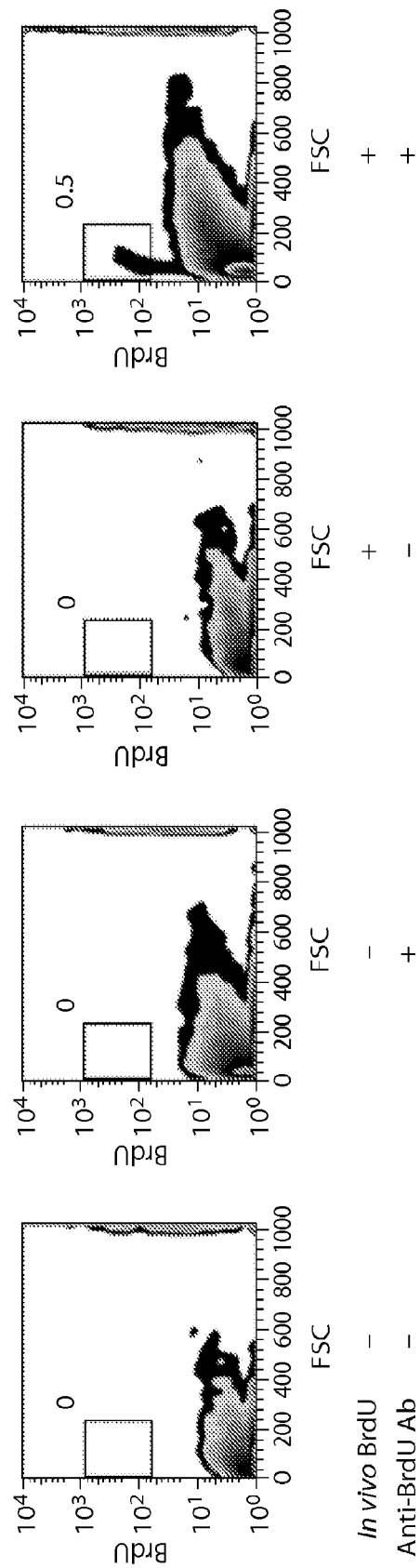
FIG. 5B shows representative flow cytometric analyses depicting specific staining of BrdU label-retaining cells in limbal epithelial cells of WT mice that did not receive BrdU (left two panels) or WT mice that received BrdU followed by an 8 week chase (right two panels). Limbal epithelial cells were recovered and stained with either anti-BrdU antibody (Ab), or with an isotype control Ab. The percentages of BrdU-positive cells within the gate are indicated on each plot.

To investigate whether ABCB5 is a marker of slow cycling, label-retaining limbal stem cells in the mammalian eye, in vivo BrdU-based 'pulse and chase' experiments [2] were performed, in which Abcb5 wild type (WT) mice were subjected over a 9-day period to daily systemic BrdU administration in order to label slow-cycling cells (pulse), followed by an 8-week BrdU-free period (chase) prior to evaluation for limbal stem cell label retention (FIG. 5A). Flow cytometric analysis of dissociated murine corneal and limbal epithelial cells revealed BrdU label-retaining cells to be detectable in the limbus, but not in the central cornea (FIG. 1B and FIG. 5B). BrdU immunohistochemical staining of full thickness murine corneas confirmed label-retaining limbal stem cells (LSCs), consistent with previous findings [2], to be located in the basal layer of murine limbal epithelium (FIG. 1C). Moreover, label-retaining LSCs expressed ABCB5 (FIG. 1C). Flow cytometric quantification confirmed ABCB5(+) cells to be predominantly BrdU-positive (90.5±0.5%, mean±s.e.m.), with ABCB5/BrdU-double positive cells comprising 1.8% of all limbal epithelial cells 4 (FIG. 1D).

Figure 1E:
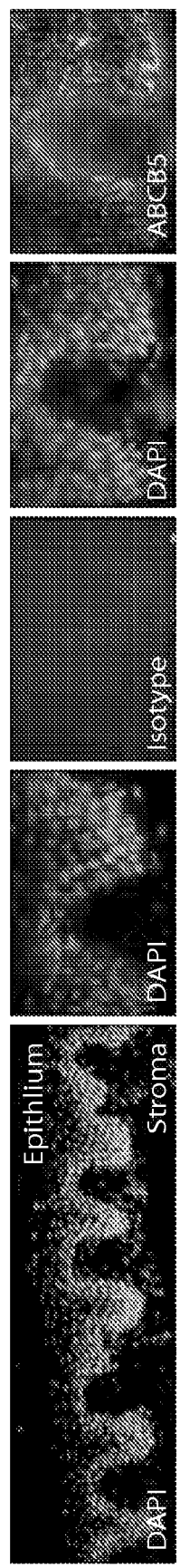
FIG. 1E shows representative immunohistochemical analyses of tangential limbal cross-sections from human corneas depicting ABCB5 expression (green) in the basal epithelial layer.
Figure 1F:
FIG. 1F shows representative immunohistochemical analyses of tangential limbal cross-sections from human corneas depicting co-expression of ABCB5 (red) with ΔNp63α (green).
Figure 1G:
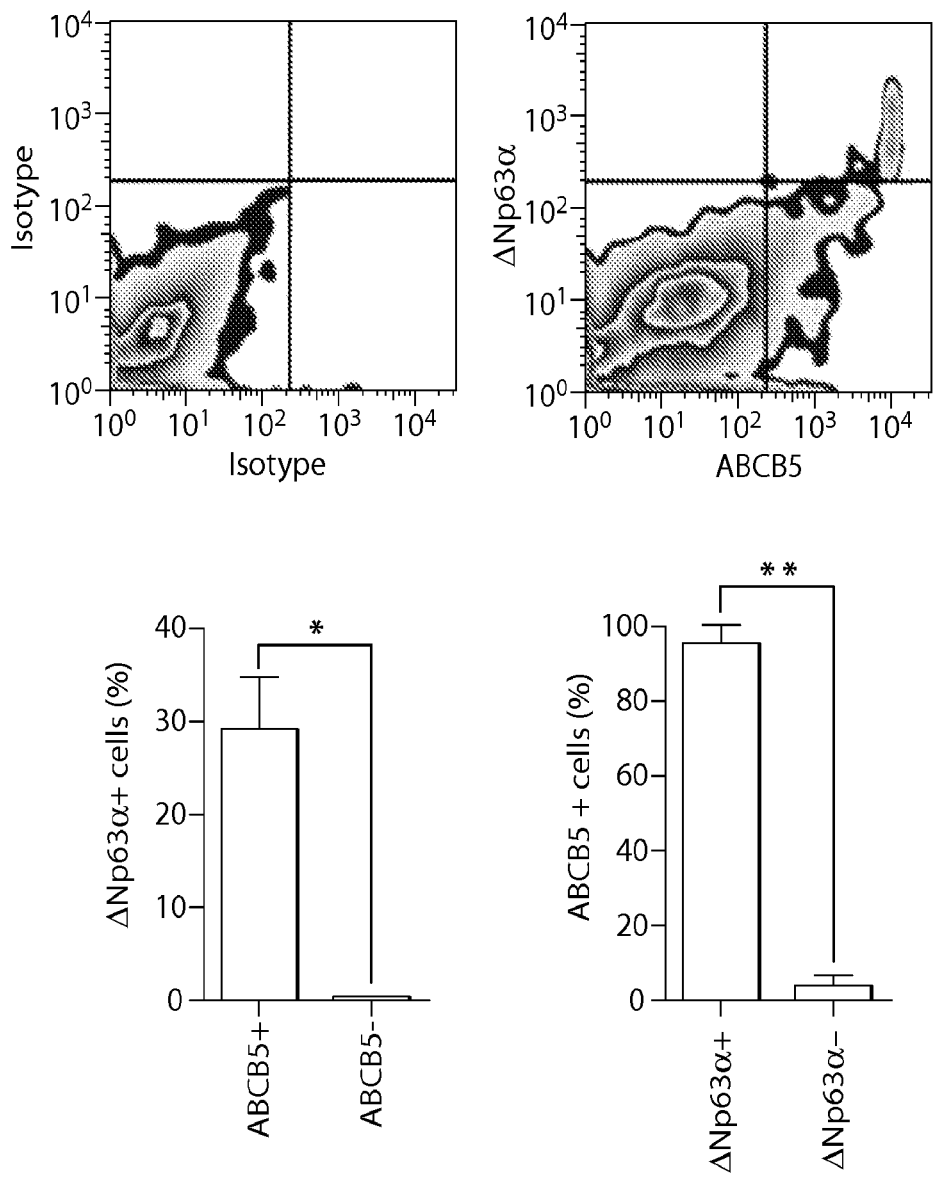
FIG. 1G shows representative cytometric analyses of human limbal epithelial cells depicting co-expression of ABCB5 with ΔNp63α. Bar graphs show ΔNp63α expression on ABCB5(+) and ABCB5(−) cells (left panel), and ABCB5 expression on ΔNp63α(+) and ΔNp63α(−) cells (right panel). Data are depicted as mean±s.e.m., n=3 experiments.
Figure 1H:
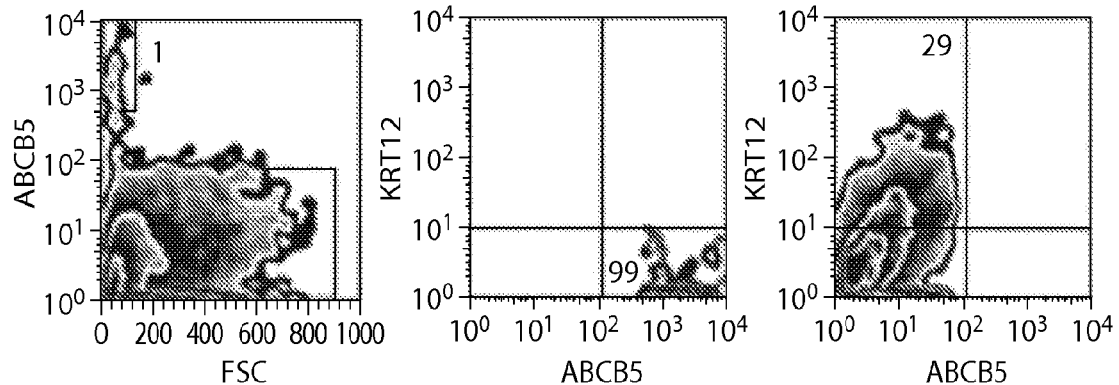
FIG. 1H shows dual color flow cytometry analyses of ABCB5 and KRT12 co-expression.
Figure 1I:
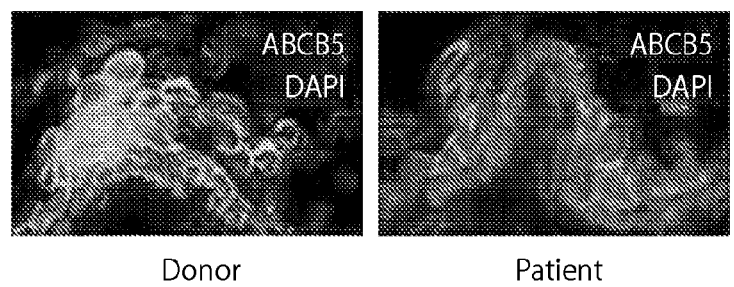
FIG. 1I shows representative immunohistochemical analyses of ABCB5 expression in limbal biopsies from patients with limbal stem cell deficiency (LSCD) performed at the time of surgery and from their respective donors. Bar graphs show the number of ABCB5(+) cells (green) in healthy donors and patients with LSCD (n=8 sections per patient/donor).
Figure 1I:
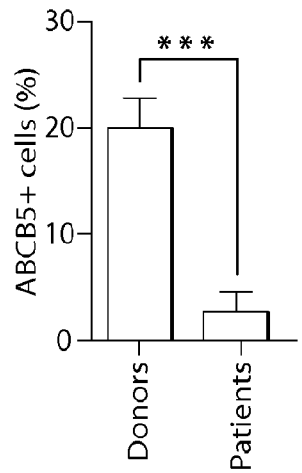
Figure 6:
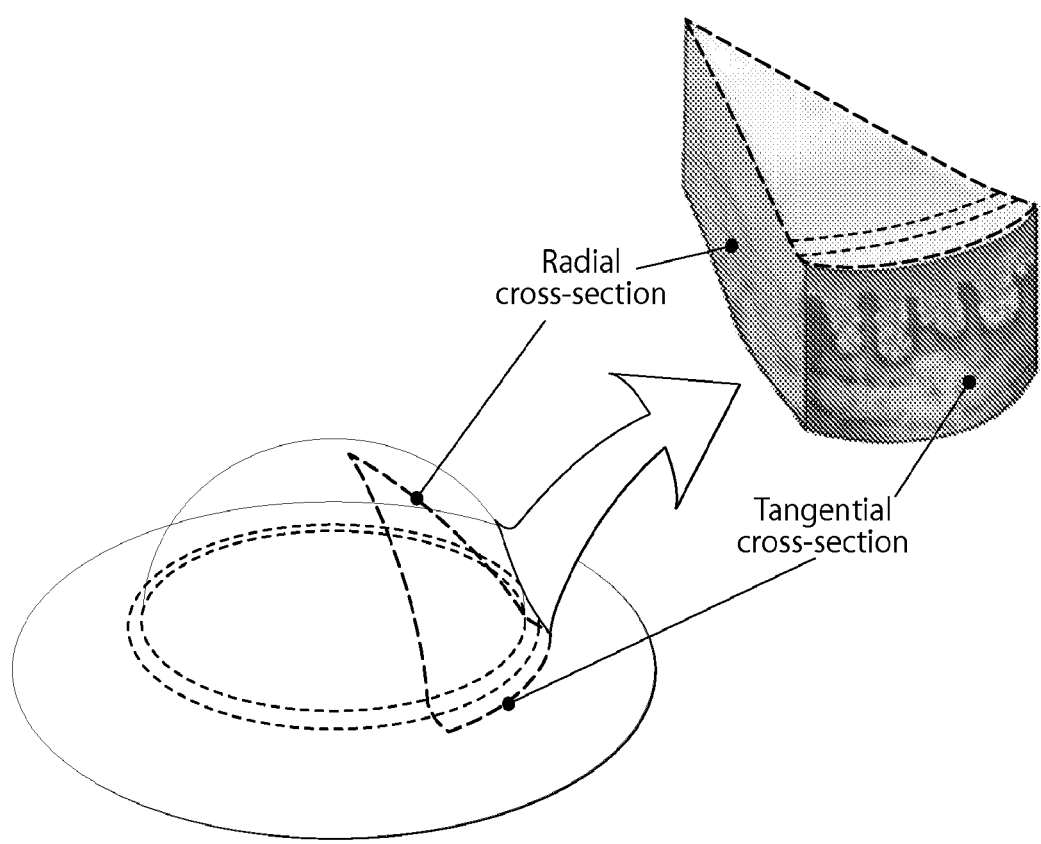
FIG. 6 shows a schematic illustration of tangential limbal cross sections from human donor corneas, indicating the location of the limbal epithelium. ABCB5(+) cells (schematically depicted as green colored cells) were found located in the basal epithelial layer.
Figure 7:
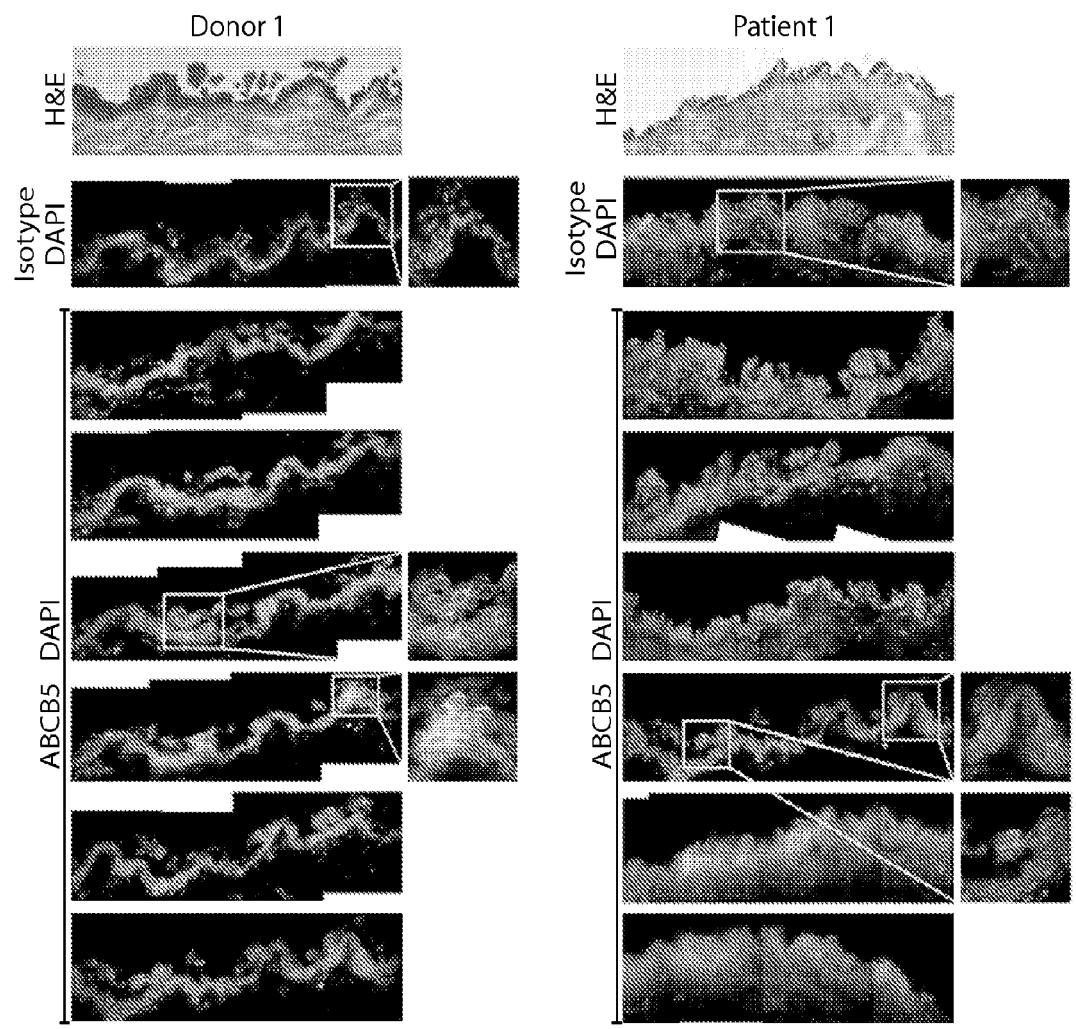
FIG. 7 shows limbal biopsies from a patient with LSCD (patient 1). Limbal biopsies were obtained from patient 1 with a chemical burn prior to receiving a penetrating keratoplasty plus kerato-limbal allograft from a cadaveric donor eye (donor 1). Serial cross sections of the biopsies were stained with either H&E, isotype control Ab or ABCB5 mAb. ABCB5 staining in the limbal epithelium of donor 1 revealed nests of ABCB5-positive cells, whereas ABCB5 positivity was reduced in the limbal epithelium of patient 1. Photographs of immunofluorescent staining are montages of sequential photos at 20× magnification.
Figure 8:
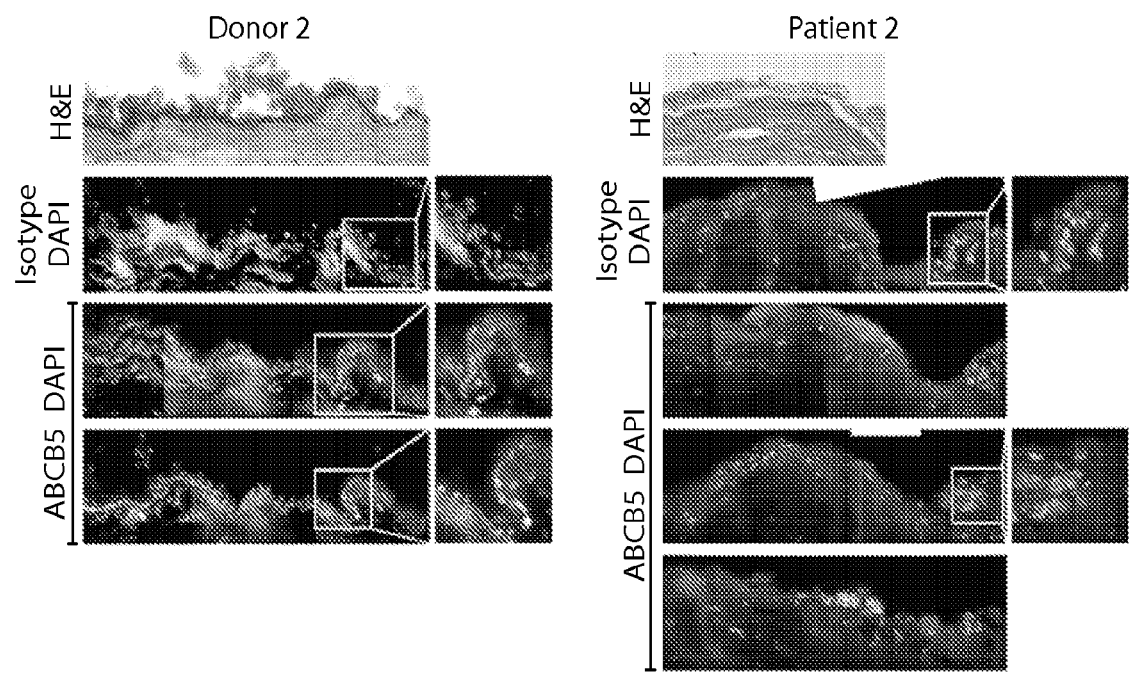
FIG. 8 shows limbal biopsies from a patient with LSCD (patient 2). Limbal biopsies were obtained from patient 2 with an autoimmune corneal melt, peripheral ulcerative keratitis and partial limbal stem cell deficiency prior to receiving a kerato-limbal autograft from the patient's normal contralateral eye (donor 2). Serial sections of the biopsies were stained with either H&E, isotype control Ab or ABCB5 mAb. ABCB5 positivity was present in the basal layer of the limbal epithelium of donor 2, while a dramatically reduced epithelial layer and no ABCB5 staining were observed in the limbus of patient 2. Photographs of immunofluorescent staining are montages of sequential photos at 20× magnification.

Similar to findings in mice, human ABCB5(+) cells were also located in the basal layer of the limbal epithelium (FIG. 1E and FIG. 6), and immunohistochemical analysis revealed that ABCB5(+) cells co-expressed the limbal stem cell marker ΔNp63α (FIGS. 1F and 1G), absent expression of the corneal differentiation marker KRT12 (FIG. 1H). Flow cytometry also revealed that ABCB5(+) cells, but not ABCB5(−) cells, expressed significant levels of ΔNp63α (28.9±5.7% and 0.1±0.1%, respectively, P=0.0364) (FIG. 1G) and showed that essentially all ΔNp63α(+) LSCs expressed ABCB5 (ΔNp63α(+) LSCs: 95.3±4.8%, ΔNp63α(−) cells: 3.6±2.1%, P=0.0032). Further, human limbal stem cell deficiency (LSCD) patients exhibited significantly reduced ABCB5(+) frequencies compared to healthy donors (2.8±1.6% and 20.0±2.6%, respectively, P<0.0001) (FIG. 1I, FIGS. 7 and 8, Table 1).

mice carrying a deletion of exon 10 of the murine Abcb5 gene (GenBank JQ655148) were generated. Exon 10 the murine Abcb5 gene encodes a functionally critical extracellular domain of the molecule homologous to extracellular loop-associated amino acid residues 493-508 of human ABCB5 (GenBank NM_178559).

Figure 2A:
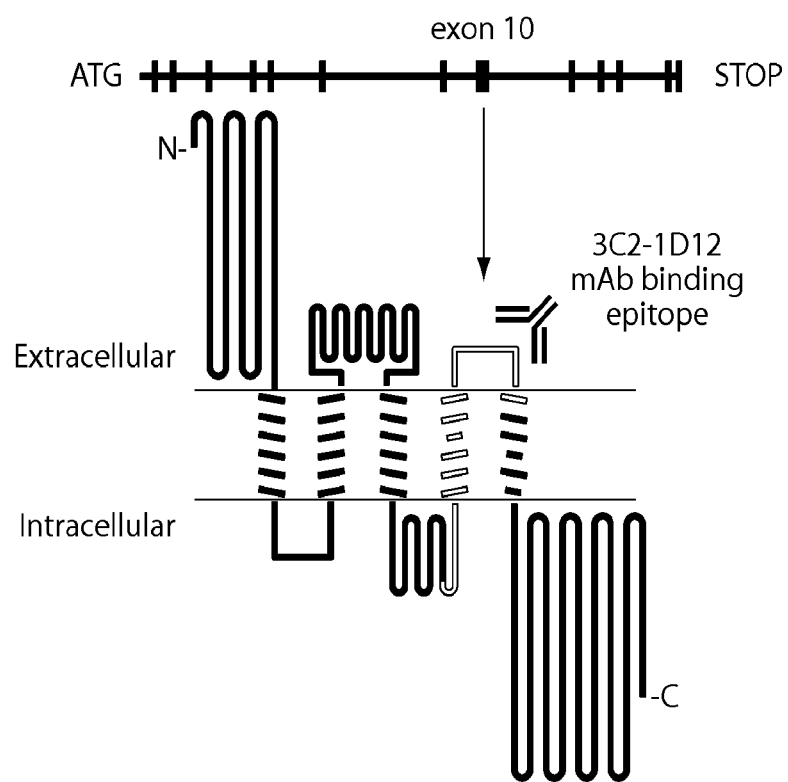
FIG. 2A shows a schematic of the murine Abcb5 gene locus and protein topology. The topological structure was determined by the TMHMM membrane topology prediction algorithm and displayed using TOPO2 software. Amino acid residues deleted in Abcb5 knockout (KO) (mutant) mice are highlighted in red.
Figure 2B:
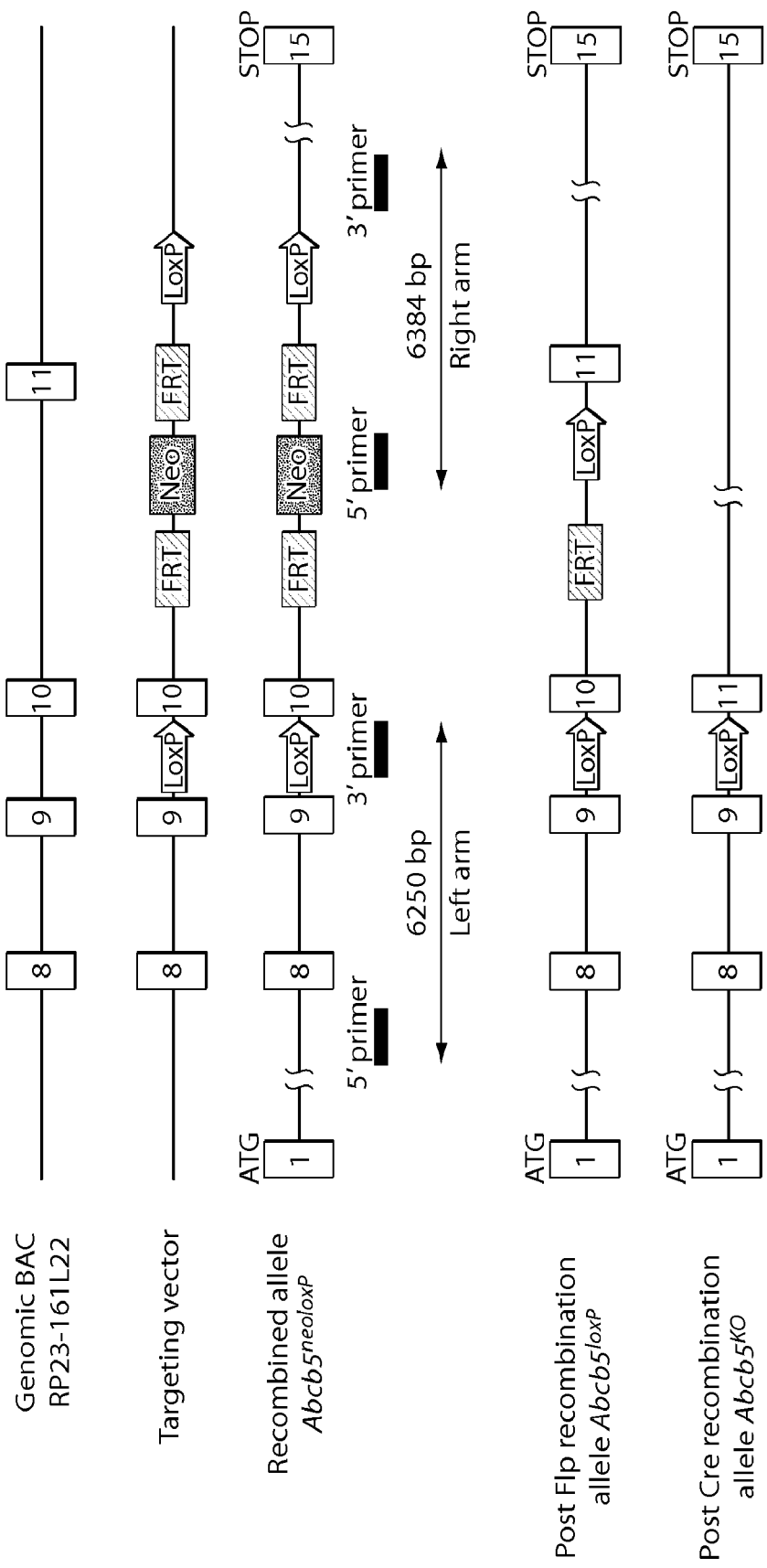
FIG. 2B shows a schematic summary of the strategy employed for generation of the Abcb5 KO mouse.

A conditional knockout targeting construct was first generated by recombineering (i.e., recombination-mediated genetic engineering) [25]. Briefly, a neomycin resistance cassette flanked by two loxP sites (based on plasmid pL-452) was inserted into the BAC clone RP23-161L22 458 base pairs upstream of exon 10 of the murine Abcb5 gene (GenBank accession number JQ655148) (FIGS. 2A and 2B). The targeted region of the BAC clone was retrieved by gap repair into the pL-253 plasmid. The retrieved plasmid contained 6006 base pairs upstream of exon 10 (not including the inserted neo cassette) and 6384 base pairs downstream of exon 10. The neomycin resistance cassette was excised by arabinose induction of Cre recombinase to leave a single loxP site upstream of exon 10. A neomycin resistance cassette flanked by two FRT sites and one loxP site (based on plasmid pL-451) was inserted 460 base pairs downstream of exon 10 to complete the targeting construct. The targeting plasmid was verified by DNA sequencing and restriction mapping. The linearized plasmid was transfected into TC1 (129S6/SvEvTac derived) embryonic stem (ES) cells and selected in G418 (Sigma-Aldrich, MO) and Fialuridine (Moravek Biochemicals, CA). Resistant colonies were expanded and screened by long-range PCR to identify targeted clones [22]. The left arm was amplified with 5'-GTTGAGGGGAGCAGCCAGAGCAAGGT-GAGAAAGGTG-3'(SEQ ID NO:1) and 5'-TTAAGGGTT-ATTGAATATGATCGGAATTGGGCTGCAGGAATT-3' (SEQ ID NO:2) primers yielding a 6250 base pair PCR product (FIG. 2B). The right arm was amplified with

TABLE 1

LSCD patient information

| Patient | Gender | Age | Cause of LSCD | Other Pathology | Previous surgery | Procedure |
|---|---|---|---|---|---|---|
| 1* | Male | 46 | Chemical burn - OD | Glaucoma suspect OD | None | KLAL + PKP |
| 2** | Female | 31 | Autoimmune corneal melt; PUK with partial LSCD | Multiple graft failure OD Retinal vasculitis OD | 2 × PKPs Cataract surgery | KLAU |

*Donor 1: cadaveric donor
**Donor 2: autologous transplant from contralateral eye
Abbreviations:
PKP Penetrating keratoplasty
KLAL Kerato-limbal allograft (limbal tissue was harvested from donor eye)
KLAU Kerato-limbal autograft (part of limbal tissue was resected from uninjured contralateral eye)
PUK Peripheral ulcerative keratitis
OD Right eye The expression of ABCB5 on label-retaining limbal stem cells in Abcb5 WT mice and ΔNp63α(+) LSCs in healthy humans, and the concurrent finding of reduced ABCB5(+) cell frequency in clinical LSCD patients, showed that ABCB5 marks LSCs.

Example 2. ABCB5 Regulates Corneal Development and Regeneration

Figure 2C:
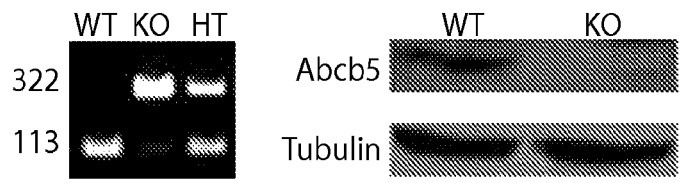
FIG. 2C, left panel, shows electrophoresis images of a polymerase chain reaction (PCR) analysis of the genomic DNA used for mouse genotyping, demonstrating a 113-base pair wild type (WT) allele and a 322-base pair deleted allele.

To investigate a potential functional role of ABCB5(+) LSCs in corneal development and regeneration, Abcb5 KO 5'-TGGGGCAGGACAGCAAGGGGGAGGAT-3' (SEQ ID NO:3) and 5'-CTGGTCCCTCTCCTGTGATCTACACAG-GCC-3' (SEQ ID NO:4) primers yielding a 6384 base pair PCR product (FIG. 2B). Two Abcb5-targeted ES clones were identified. These clones were expanded and injected into C57BL/6 blastocysts that were then transferred to the uterus of pseudo-pregnant females. High-percentage chimeric male mice (Abcb5$^{neo-loxP/wt}$) were bred into a C57BL/6 background to obtain germ-line transmission. Germ-line transmission of the Abcb5$^{neo-loxP}$ allele was confirmed by PCR analysis of genomic DNA using 5'-GGAAGA- CAATAGCAGGCATGCTGGG-3' (SEQ ID NO:5), 5'-GGCTGGGGCAACTGAAAAGTAGCAT-3' (SEQ ID NO:6), and 5'-TTTCAGCTTCAGTTTATCACAAT-GTGGGTT-3' (SEQ ID NO:7) primers designed to amplify the 385 base pair targeted allele and the 284 base pair WT allele. Heterozygous Abcb5$^{neo-loxP}$ mice were then intercrossed with hACTB-FLPe transgenic mice [26] to remove the neomycin resistance cassette. PCR analysis of genomic DNA was performed to confirm removal of the neomycin resistance cassette in the genome of Abcb5$^{loxP/wt}$ mice using 5'-ACTT GGTGCGGTGACTCTGAATTTTGC-3' (SEQ ID NO:8) and 5'-TAGCAACATTTCTGGCATTTTAGGCTG-3' (SEQ ID NO:9) primers designed to amplify a 494 base pair neomycin resistance cassette-deleted allele and a 390 base pair WT allele. Abrogation of ABCB5 protein expression in Abcb5 KO animals was determined by Western blots of murine tissues (FIG. 2C). Abcb5 WT and Abcb5 KO cell lysates were immunoblotted using monoclonal ABCB5 antibody 3C2-1D12 [6,27] (5.5 m/ml) or α-Tubulin rabbit polyclonal antibody (1:5000 dilution) (Abcam, MA). After treatment with HRP-conjugated specific secondary antibodies (1:5000 dilution) (Jackson ImmunoResearch, PA), signals were visualized on film by enhanced chemiluminescence.

To determine the outcome of a complete loss of ABCB5 function, exon 10 of the murine Abcb5 gene was deleted by breeding Abcb5$^{loxP}$ mice with Ella-Cre mice, which express Cre recombinase at the zygote stage [14,15] (FIG. 2B). Deletion of the genomic region between the two loxP sites was confirmed by PCR analysis of genomic DNA using 5'-GGCTGGGGCAACTGAAAAGTAGCAT-3' (SEQ ID NO:10), 5'-GCAAATGTGTACTCTGCGCTTATTTAATG-3' (SEQ ID NO:11) and 5'-TGGTGCAGACTACA-GACGTCAGTGG-3' (SEQ ID NO:12) primers designed to amplify a 322 base pair cre-deleted allele (null) and al 13 base pair WT allele (FIG. 2C). Heterozygous Abcb5$^{null/WT}$ mice with the germline deletion of exon 10 were intercrossed to produce homozygous Abcb5$^{null/null}$ mutants (Abcb5 KO mice). Mice were maintained on a 129S6/SvEvTac/C57BL/6 mixed genetic background, and littermates were used as controls for experimental analyses.

Figure 2D:
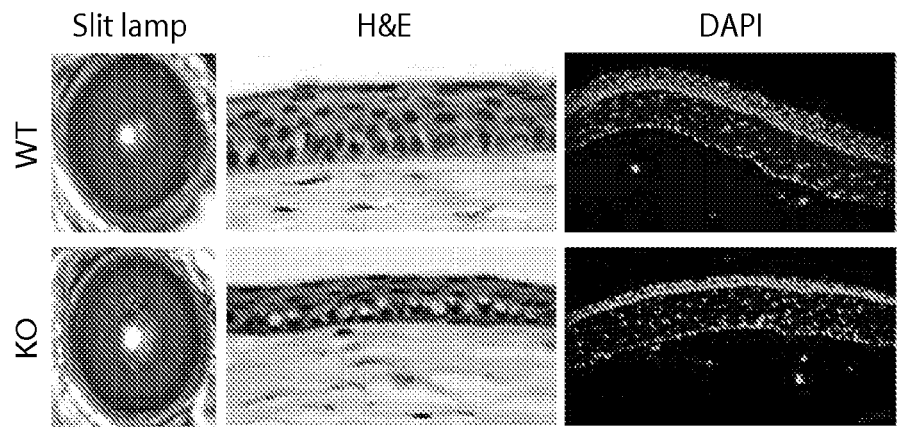
FIG. 2D shows images of a phenotypic characterization of murine Abcb5 WT and Abcb5 KO corneas using slit lamp examination (left panels), hematoxylin and eosin (H&E) staining (middle panels) and 4',6-diamidino-2-phenylindole (DAPI) staining (right panels). Bar graphs below depict the number of DAPI(+) epithelial cells in Abcb5 KO and Abcb5 WT murine central cornea and limbus. Data shown represent means±s.e.m., n=4 experiments.
Figure 2D:
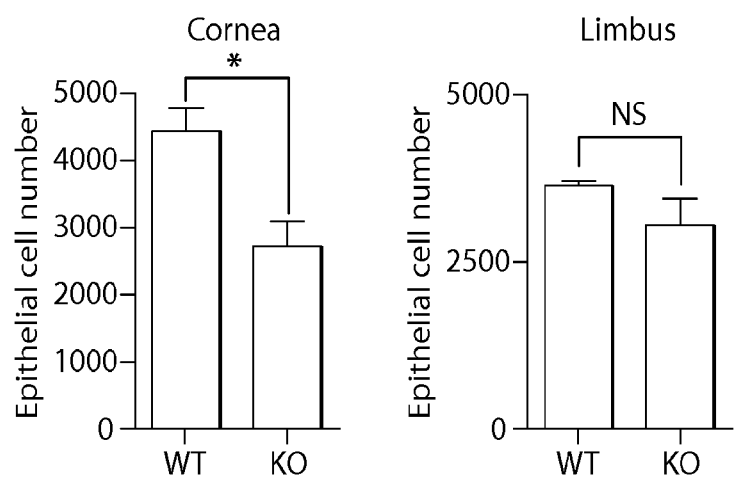
Figure 2E:
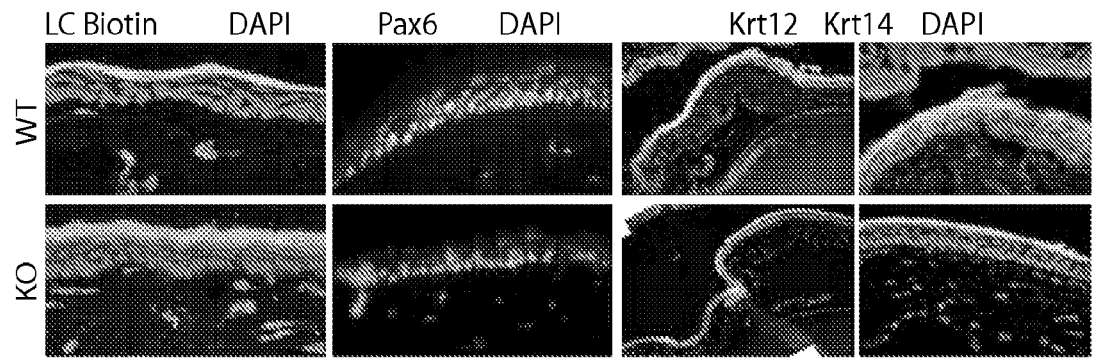
FIG. 2E shows LC-biotin diffusion analyses and immunofluorescence protein expression analyses of PAX6, KRT12 and KRT14 in Abcb5 WT and Abcb5 KO mice. Bar graphs depict percent PAX6(+) and KRT12(+) epithelial cells in Abcb5 KO and Abcb5 WT mice. Data shown represent means±s.e.m., n=6 experiments.
Figure 2E:
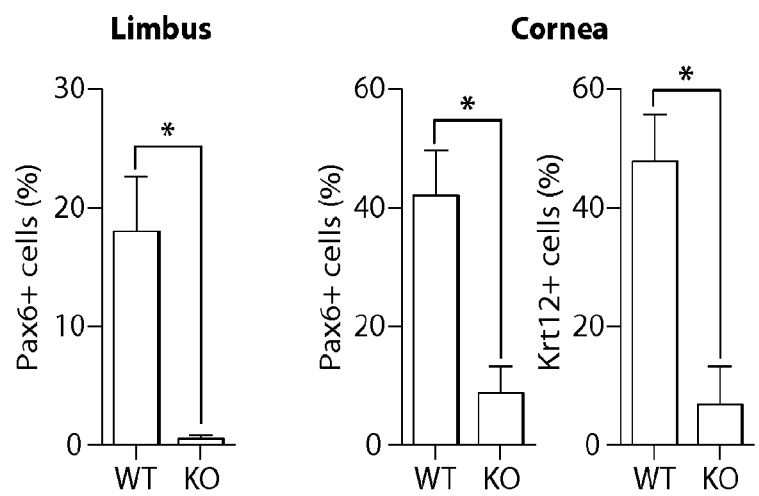
Figure 9:
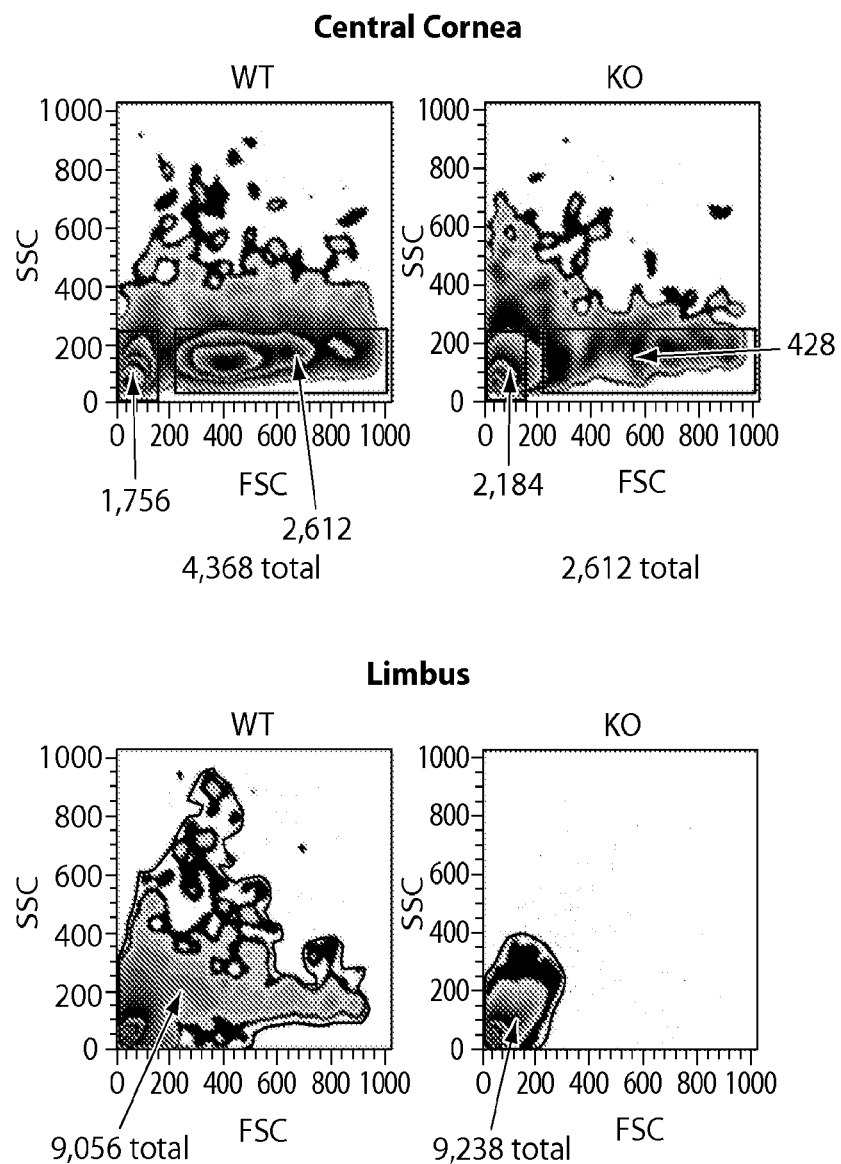
FIG. 9 shows representative flow cytometry analyses of either the limbal or the central corneal epithelium of Abcb5 WT and Abcb5 KO mice. Forward scatter (FSC) and Side scatter (SSC) indicates cellular size and granularity, respectively. Central corneal epithelium of Abcb5 KO mice showed a reduced number of epithelial cells compared to Abcb5 WT epithelium (left panels), caused by a reduction in larger cells (right gates), but not smaller cells (left gates). There was no reduction in the number of limbal epithelial cells (right panels). Representative results of samples pooled from four eyes are shown (n=3 experiments).
Figure 10:
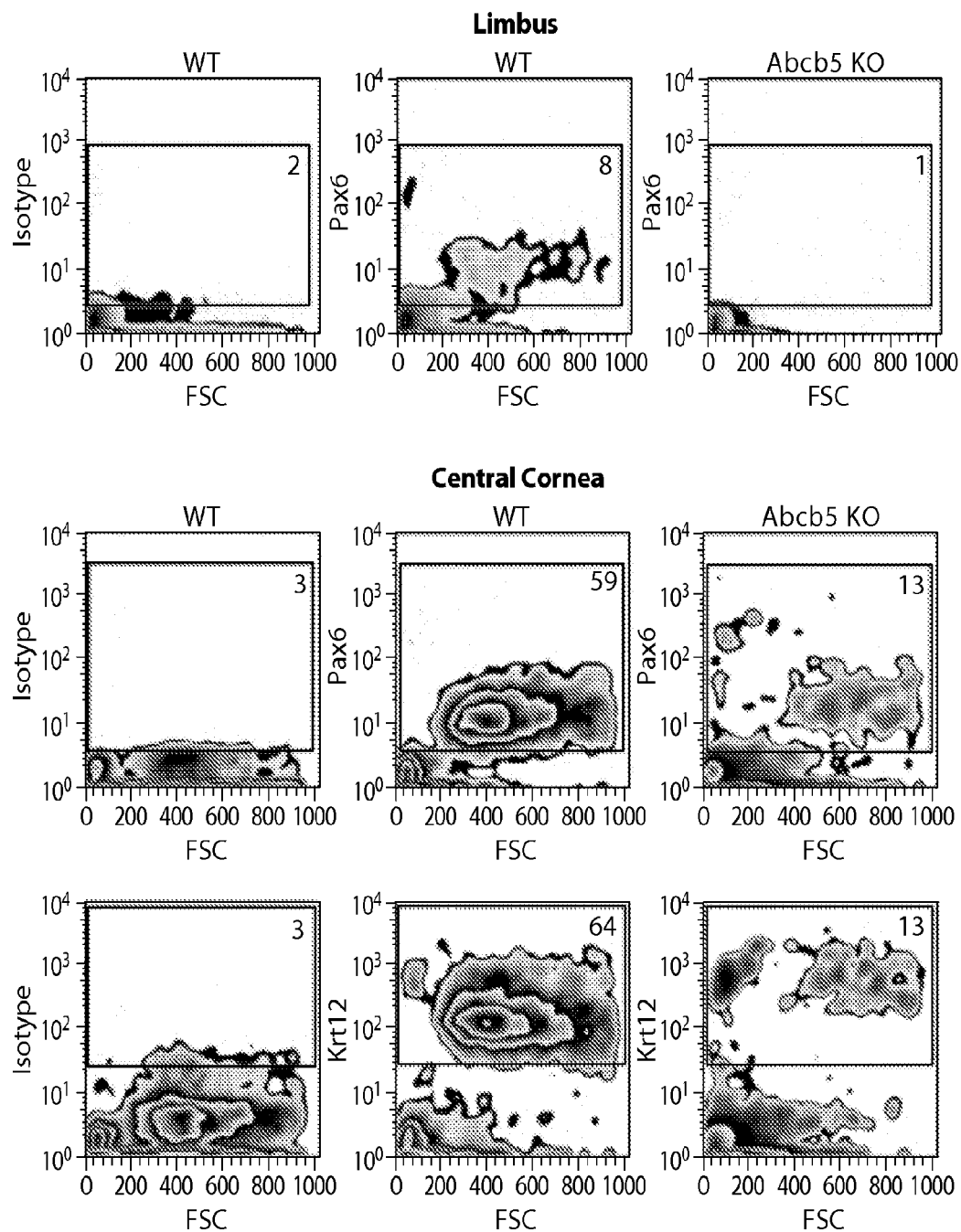
FIG. 10 shows representative flow cytometry analyses of epithelial cells harvested from either the limbus (top) or the central cornea (bottom) of Abcb5 WT and Abcb5 KO mice. Recovered cells were stained with isotype control antibody, anti-Pax6 antibody or anti-Krt12 antibody. There was a reduced frequency of PAX6(+) and KRT12(+) epithelial cells in the central cornea of Abcb5 KO mice and a corresponding reduced frequency of PAX6(+) cells in the limbus of Abcb5 KO mice. Red gates identify PAX6(+) or KRT12 (+) cells compared to isotype control staining. Representative analyses of n=3 experiments are shown.
Figure 11A:
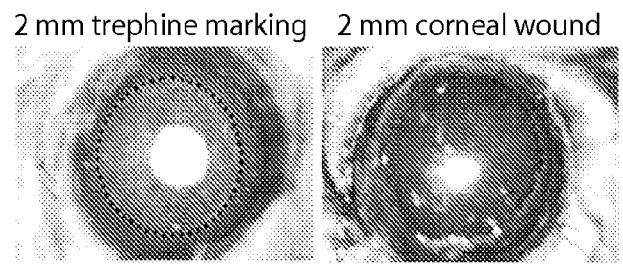
FIG. 11A shows a wound area to be debrided marked with a 2 mm trephine and the epithelium removed.
Figure 11B:
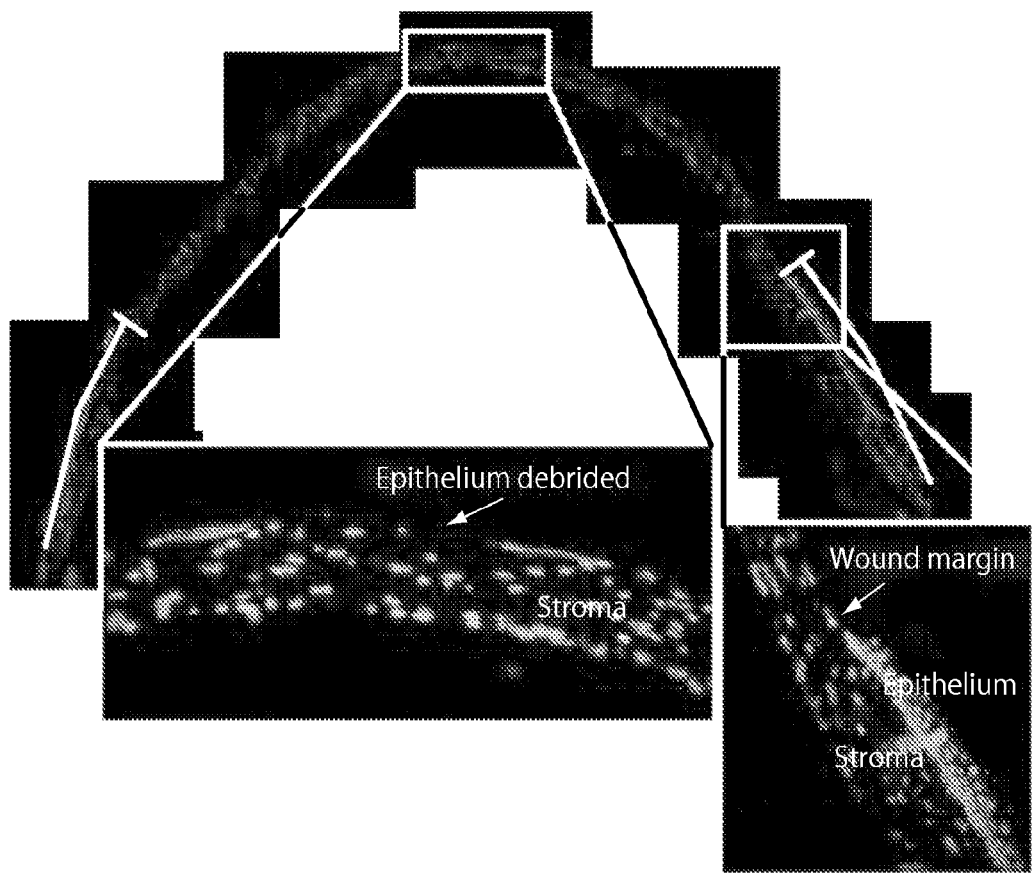
FIG. 11B shows a DAPI-stained cross section of the cornea immediately following central epithelial debridement depicting the wound margins and exposed central corneal stroma. Image is a montage of sequential photos at 10× magnification.
Figure 11C:
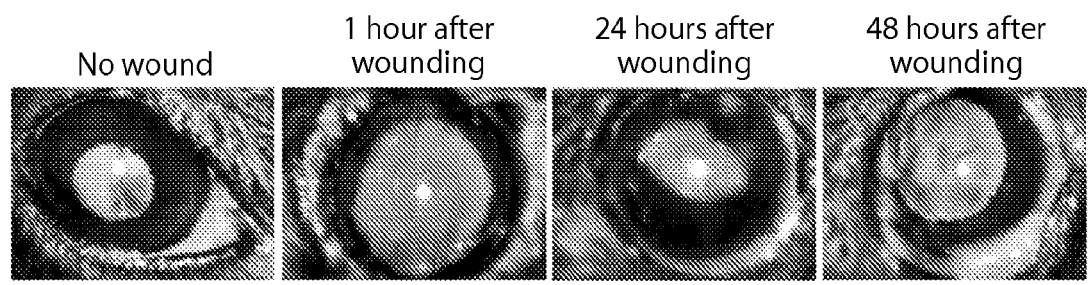
FIG. 11C shows fluorescent images of corneal epithelial wound closure monitoring at 1, 24, and 48 hours post debridement.
Figure 11D:
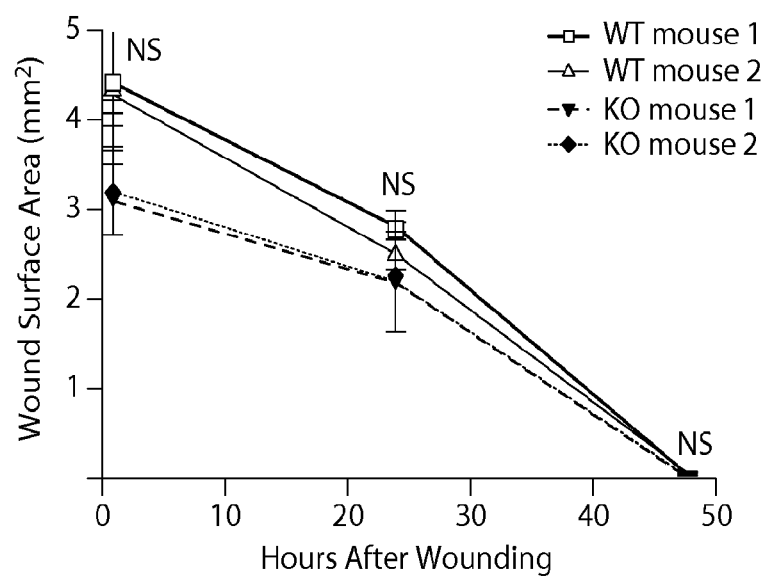
FIG. 11D shows a graph of wound closure rates, which were not significantly different between Abcb5 WT and Abcb5 KO mice (summary of n=2 replicate experiments).

Abcb5 KO mice were born alive and appeared indistinguishable from their WT littermates at birth upon physical examination, with no gross anatomical defects of Abcb5 KO corneas detectable by slit lamp examination (FIG. 2D). However, histological analysis of mutant corneas demonstrated profound developmental abnormalities characterized by flattening of the corneal epithelium compared to WT controls, with significantly reduced epithelial cell numbers in the central cornea, but not in the limbus, as evidenced by hematoxylin and eosin (H&E) stain, 4',6-diamidino-2-phenylindole (DAPI) staining and flow cytometry (Central cornea: 2688±399 cells and 4427±346 cells, respectively, P=0.0165; limbus: 3015±433 cells and 3629±94 cells, respectively, P=0.2377) (FIG. 2D and FIG. 9). Abcb5 KO corneas also exhibited severe epithelial tight junction defects as determined by LC biotin staining (FIG. 2E), and mutant mice showed significantly decreased limbal and corneal PAX6 and corneal KRT12 expression as compared to WT mice (limbal PAX6: 0.3±0.3% and 18.0±4.6%, respectively, P=0.0181; corneal PAX6: 8.3±4.6% and 42.0±7.6%, respectively, P=0.0192; corneal KRT12: 6.5±6.5% and 47.7±8.2%, respectively, P=0.0382) (FIG. 2E, FIG. 10), demonstrating a novel essential role of ABCB5 in normal corneal development.

Example 3. ABCB5 Regulates Limbal Stem Cell Quiescence

To determine whether corneal regeneration is dependent on intact ABCB5 function, Abcb5 KO and WT mice were subjected to central corneal epithelial debridement injury followed by evaluation for corneal regeneration (FIGS. 11A-11D). After anesthesia with intraperitoneal injection of Ketamine (120 mg/kg body weight, Hospira, Ill.) and Xylazine (10 mg/kg body weight, Burns Veterinary Supply, NY), followed by topical application of one drop of 0.5% Proparacaine eye drops (Akorn, IL) into each eye, a 2 mm diameter epithelial wound was created by demarcating an area of the central cornea with a 2 mm trephine and removing the epithelium within the circle with a small scalpel, leaving the basement membrane intact. In each animal, the procedure was performed on the right eye. Ak-Spore Ophthalmic Ointment (Bacitracin Zinc, Neomycin Sulfate and Polymyxin B Sulfate, Akorn, IL) was applied to both eyes immediately after wounding and then twice per day for the next 48 hours to prevent corneal infection and dryness. Analgesia was provided by subcutaneous injections of Buprenex (Reckitt Benckiser Pharmaceuticals, Berkshire, 30 UK) every 12 hours for 48 hours postoperatively at the dose of 1 mg/kg. The wound healing was monitored as described previously [29]. Animals were euthanized 48 hours post-operatively and the integrity of corneal epithelial tight junctions was assessed using the LC-Biotin staining method performed as described [31]. Briefly, LC-Biotin staining solution prepared by dissolving 1 mg/ml EZ-Link-Sulfo-NHS-LC-Biotin (Pierce, Ill.) in HBSS (Hank's Balanced Salt Solution, Lonza, Md.) plus 2 mM MgCl$_2$, and 1 mM CaCl$_2$ was applied to wounded and non-wounded eyes for 15 minutes at the time of euthanasia. Eyes were rinsed with PBS (Lonza, Md.), enucleated and placed in Tissue-Teck OCT (Sakura Finetek, CA) for frozen sectioning.

Figure 2F:
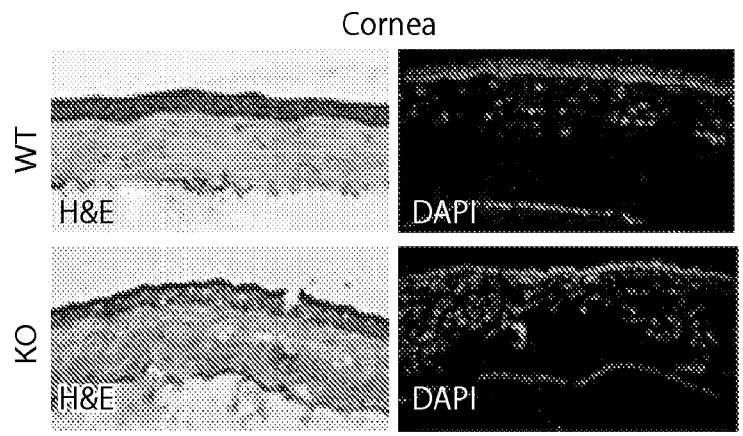
FIG. 2F shows H&E and DAPI staining of Abcb5 WT and Abcb5 KO corneas 48 hours after epithelial debridement wounding. Bar graph (bottom) represents the number of DAPI(+) cells per section in Abcb5 WT and Abcb5 KO mice. Data shown represent means±s.e.m., n=4 experiments.
Figure 2F:
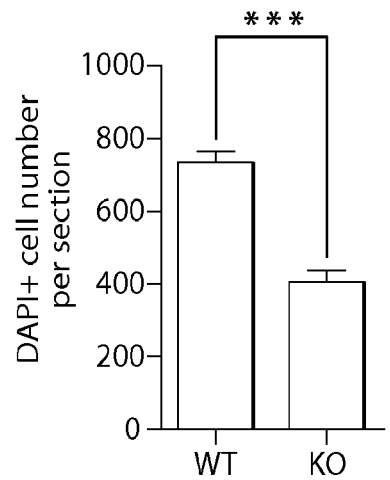
Figure 2G:
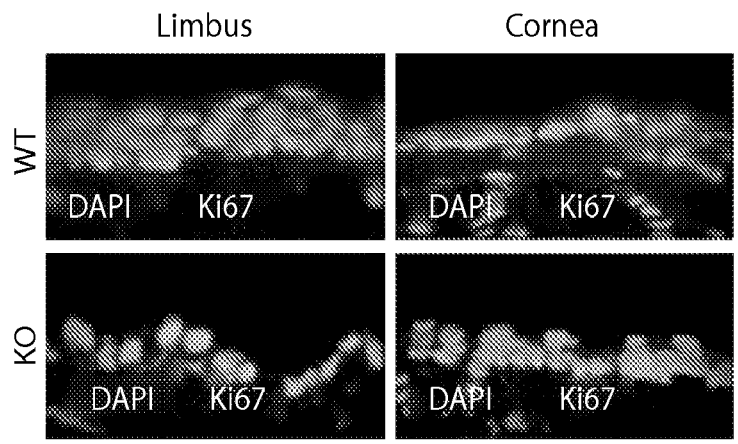
FIG. 2G shows immunofluorescence analyses of Ki67 in the limbus and central cornea of Abcb5 WT and Abcb5 KO mice 48 hours after epithelial debridement wounding. Bar graphs (bottom) represent the percentage of Ki67(+) in limbus and in cornea Abcb5 KO and Abcb5 WT mice (means±s.e.m., n=4 experiments, respectively).
Figure 2G:
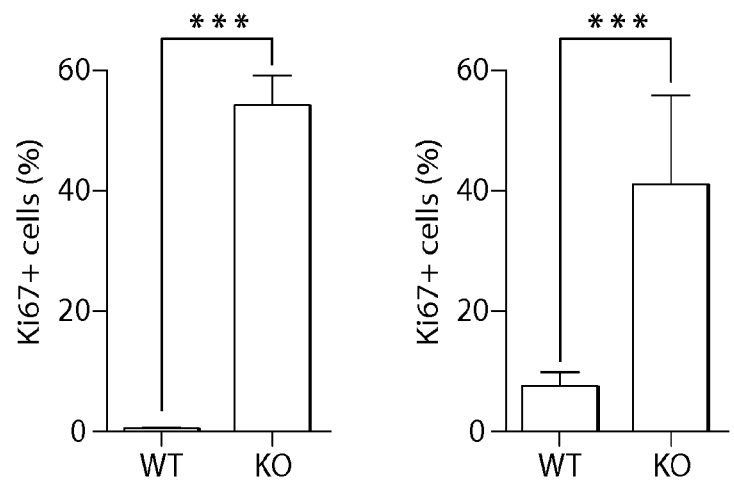
Figure 2H:
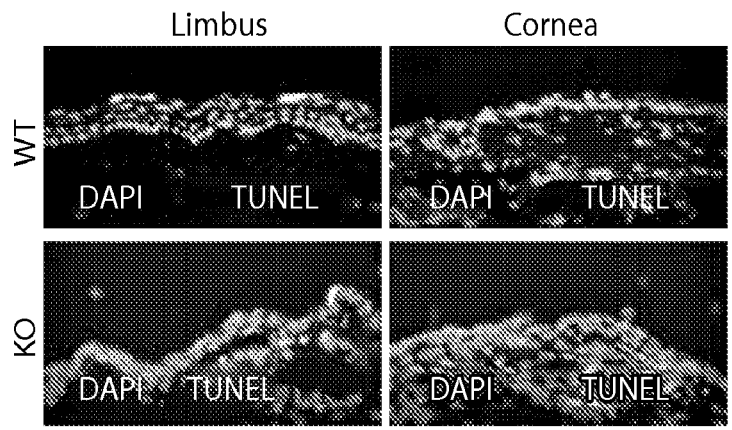
FIG. 2H shows immunofluorescence analyses of TUNEL staining in the limbus and central cornea of Abcb5 WT and Abcb5 KO mice 48 hours after epithelial debridement wounding. Bar graphs (bottom) represent the percentage of TUNEL+ epithelial cells in limbus and in cornea in Abcb5 KO and Abcb5 WT mice (means±s.e.m., n=4 experiments, respectively).
Figure 2H:
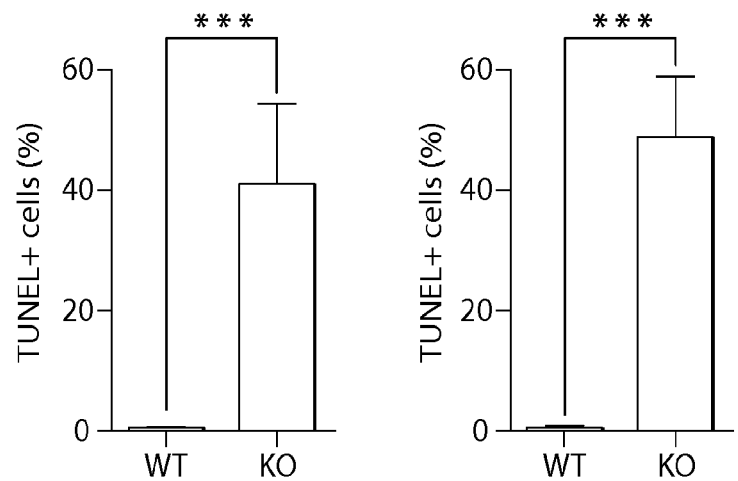
Figure 12:
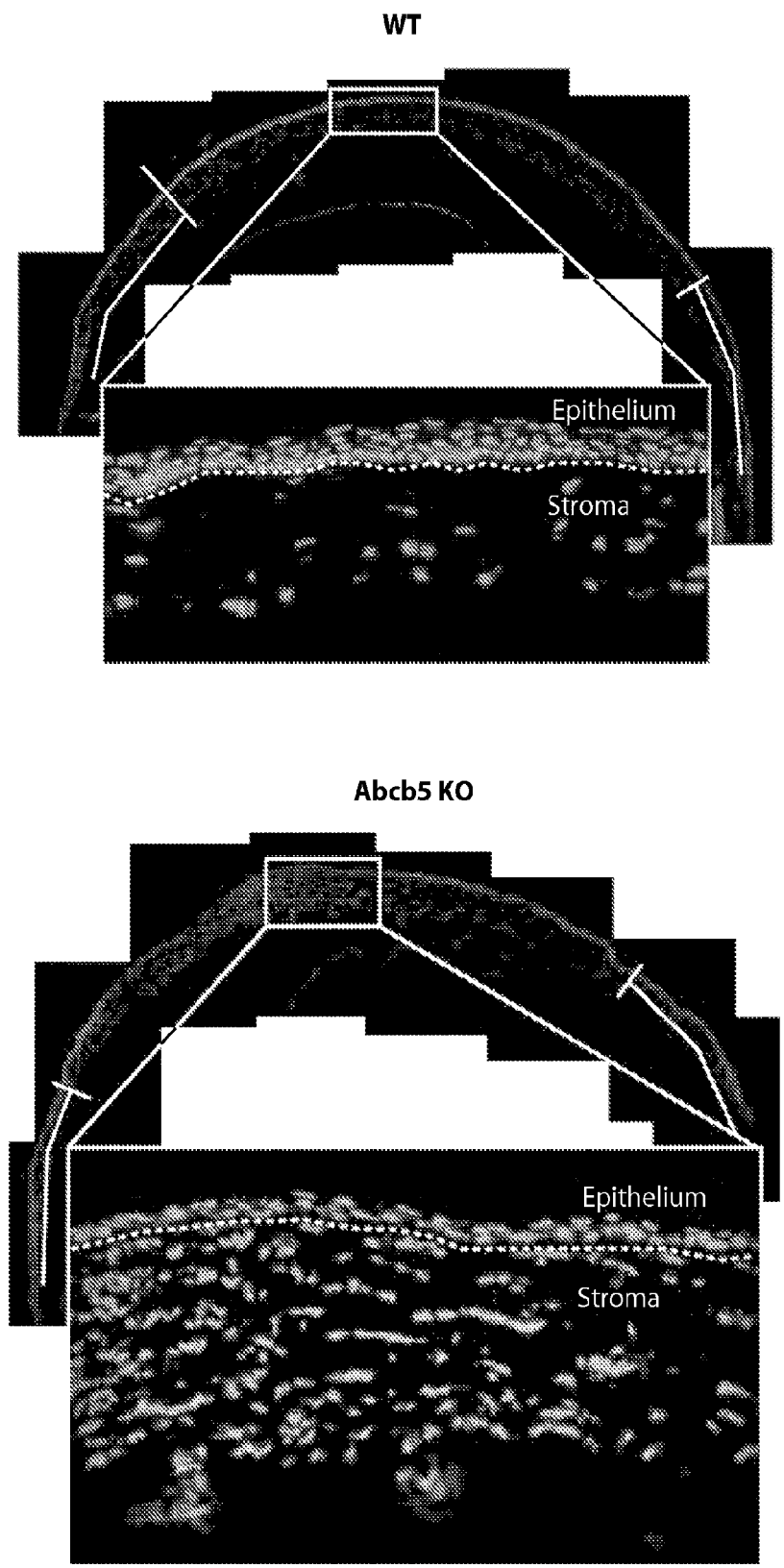
FIG. 12 shows representative DAPI-stained composite corneal cross sections of Abcb5 WT (top) and Abcb5 KO (bottom) mice 48 hours after a corneal epithelial debridement wound, demonstrating a reduced number of epithelial cells in Abcb5 KO mice. The white dashed line demarcates the epithelium from stroma; the white box indicates area shown at 20× magnification (montage pictures are at 10× magnification); white lines demarcate the area in which epithelial cells were counted. Epithelial cells were counted within the standardized area in at least three consecutive composite cross sections in three replicate mice per group in two separate experiments (data shown in FIG. 2F).
Figure 13:
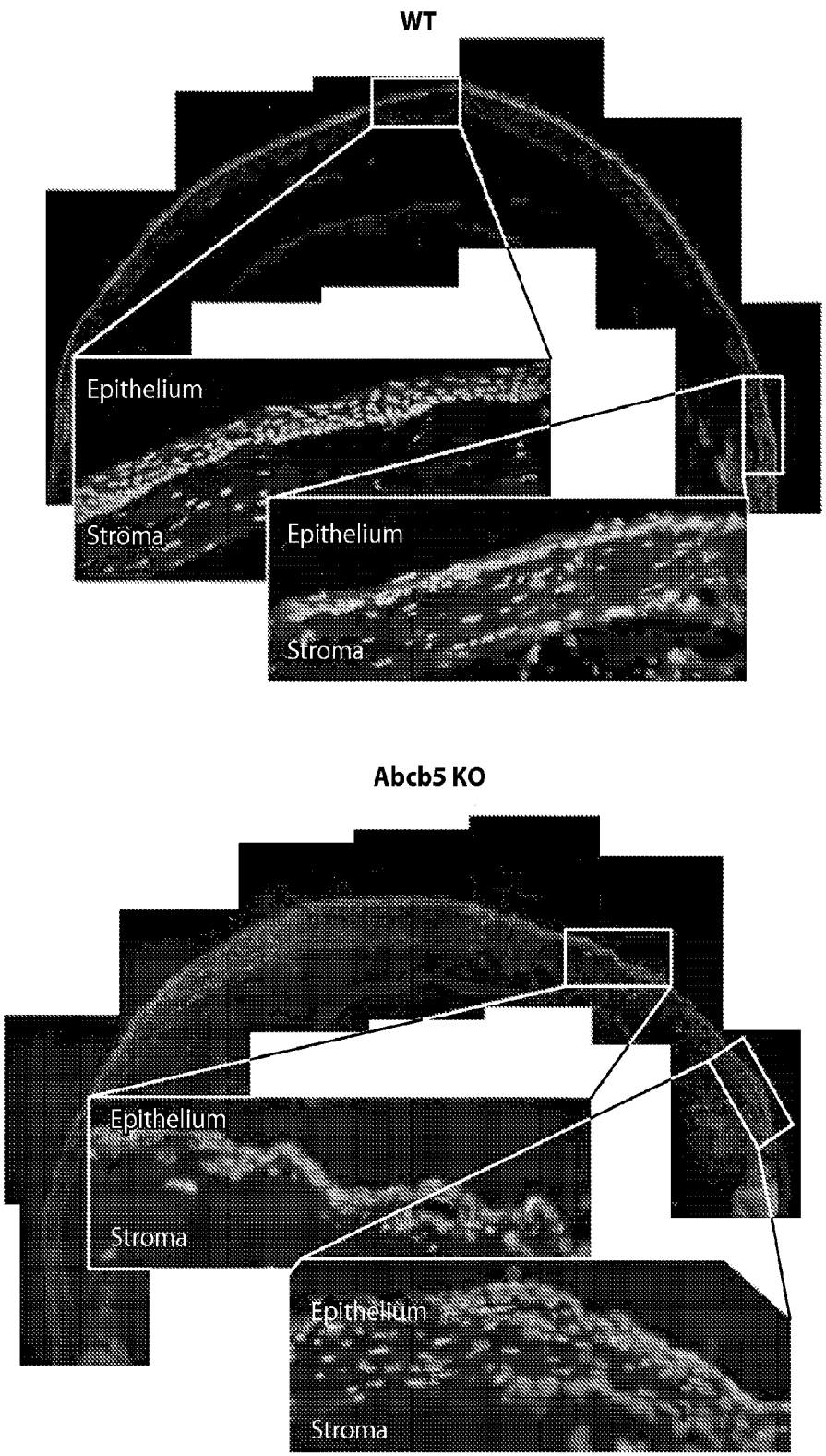
FIG. 13 shows representative TUNEL-stained composite corneal cross sections of Abcb5 WT (top) and Abcb5 KO (bottom) mice 48 hours after a corneal epithelial debridement wound, demonstrating increased numbers of apoptotic cells in Abcb5 KO mice. Areas defined by the white box are shown at 20× magnification (montage pictures at 10× magnification). The number of TUNEL-positive epithelial cells was counted, and the data from two replicate experiments are summarized in FIG. 2H.

While no significant differences were observed in the rate of wound closure between Abcb5 WT and Abcb5 KO mice (FIGS. 11C and 11D), histological analysis revealed severely abnormal corneal restoration in Abcb5 KO mice, as compared to Abcb5 WT mice, characterized by highly irregular appearance of the epithelium with reduced number of epithelial cells (403.3±29.7 and 737.2±28.2, respectively, P<0.0001) (FIG. 2F and FIG. 12), significantly increased cellular proliferation as demonstrated by enhanced Ki67 expression (limbus: 54.0±5.0% and 0.3±0.2%, respectively, P<0.0001; cornea: 41.2±12.8% and 1.0±0.5%, respectively, P=0.0257) (FIG. 2G), and significantly enhanced rates of apoptosis as demonstrated by TUNEL staining (limbus: 41.2±12.8% and 1.0±0.5%, respectively, P=0.001; cornea: 49.0±1.0% and 0.4±0.3%, respectively, P<0.0001) (FIG. 2H and FIG. 13).

Figure 3A:
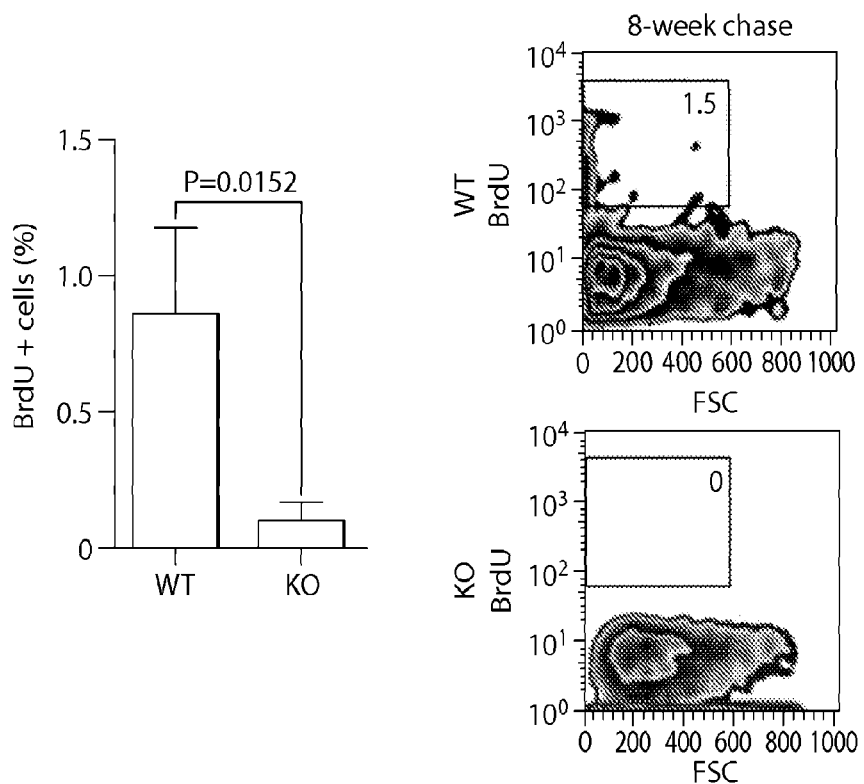
FIG. 3A shows flow cytometry analyses showing loss of BrdU label-retaining cells in Abcb5 KO and Abcb5 WT limbal epithelial cells after an 8-week chase.
Figure 3B:
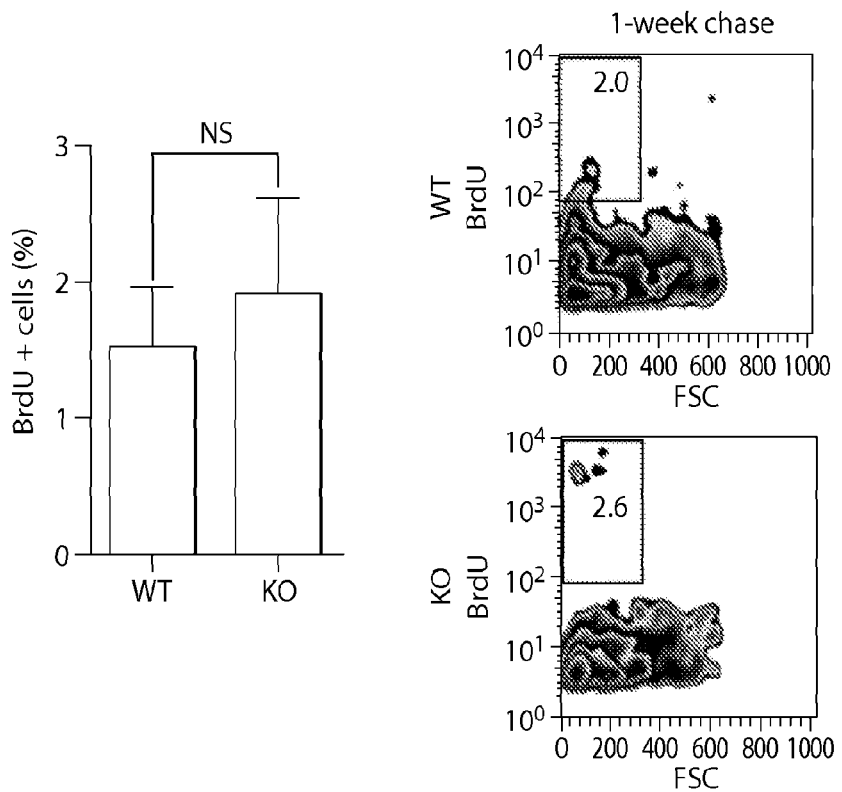
FIG. 3B shows flow cytometry analyses showing loss of BrdU label-retaining cells in Abcb5 KO and Abcb5 WT limbal epithelial cells after a 1-week chase (means±s.e.m., n=6 experiments).
Figure 3C:
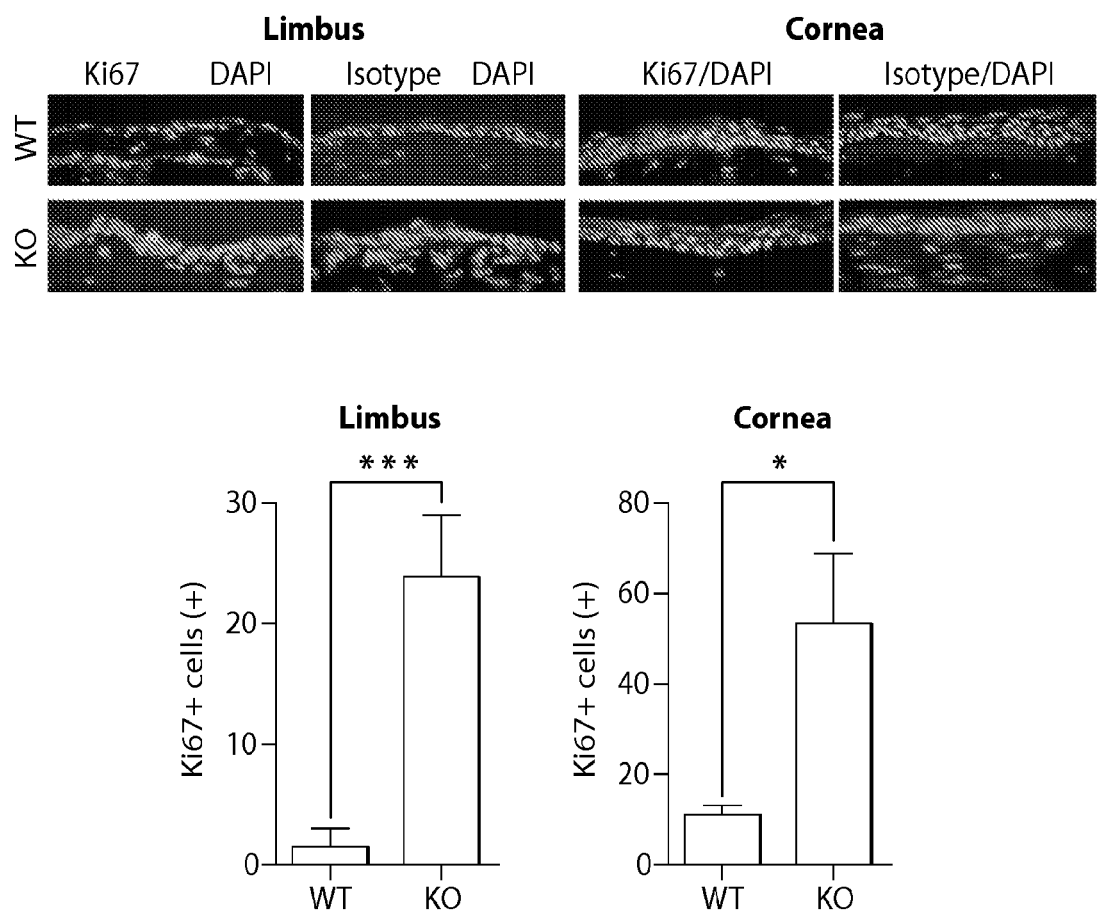
FIG. 3C shows immunofluorescence analyses of Ki67 expression in Abcb5 WT and Abcb5 KO mouse limbus and cornea. Bar graphs on the right illustrate the percentages of Ki67(+) cells in Abcb5 WT and Abcb5 KO mice in the limbus and cornea. Illustrated are means±s.e.m. (n=3 experiments).
Figure 3D:
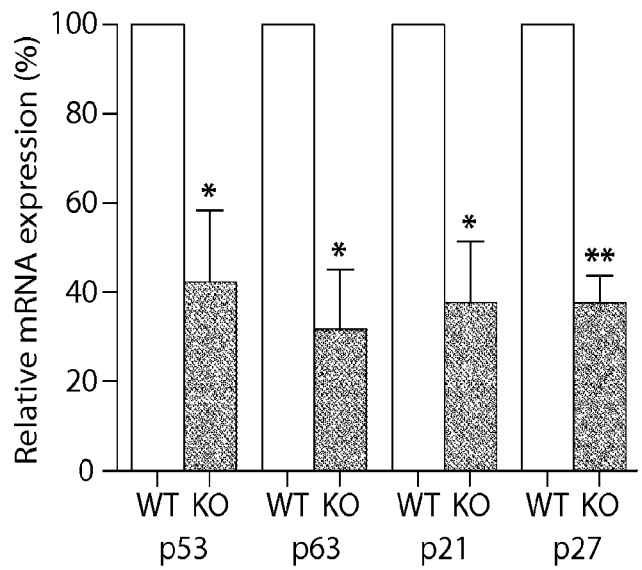
FIG. 3D shows a graph of mRNA expression of p53, p63, p21 and p16 in Abcb5 WT and Abcb5 KO corneas. Bars represent relative mRNA expression levels in Abcb5 KO mice as a percentage of mRNA expression levels in Abcb5 WT mice (means±s.e.m., n=4 experiments).
Figure 3E:
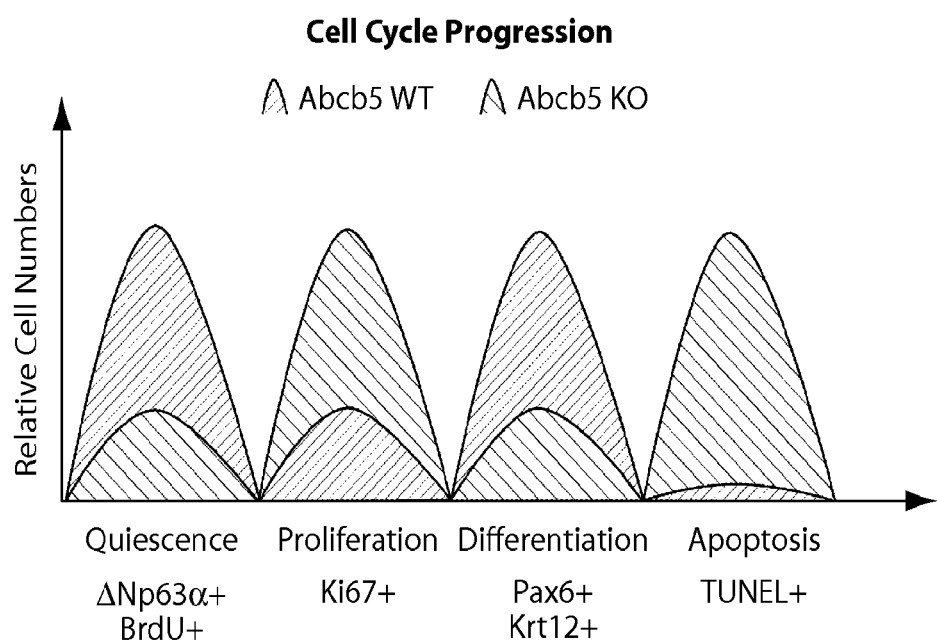
FIG. 3E shows a schematic summary of the role of ABCB5 in cell cycle regulation and normal corneal development and regeneration. Abrogation of ABCB5 expression in Abcb5 KO mice (blue) results in loss of BrdU(+) label-retaining cells and down regulation of critical cell cycle regulators, including p63. This leads to increased cellular proliferation as evidenced by enhanced Ki67 expression in Abcb5 KO mice. Augmented proliferation and inability to withdraw from the cell cycle explain the profound differentiation deficiencies, evidenced by decreased PAX6 and KRT12 expression and increased rates of apoptosis in Abcb5 KO mice, evidenced by enhanced TUNEL staining.

Pulse-chase BrdU-labeling (FIGS. 5A and 5B) and flow cytometric analysis of dissociated murine limbal epithelial cells revealed that after an early, 1-week chase period, no significant difference existed between the numbers of BrdU-labeled epithelial cells in Abcb5 KO-derived and Abcb5 WT-derived specimens, indicative of equal BrdU uptake by Abcb5 KO and Abcb5 WT limbal cells (1.9±0.7% and 1.5±0.4%, respectively, P=0.6971). By contrast, after an 8-week chase period, label-retaining LSC frequency was markedly and significantly reduced (by 89%) in Abcb5 KO mice, compared to Abcb5 WT controls (frequency: 0.1±0.1% and 0.9±0.3%, respectively P=0.0152) (FIGS. 3A and 3B), demonstrating that abrogation of ABCB5 function induces cellular proliferation of normally quiescent LSCs. Consistent with this result, Ki67 expression, indicative of cellular proliferation, was significantly enhanced in Abcb5 KO corneas, as compared to Abcb5 WT control corneas (limbus: 24.0±5.0% and 1.5±1.5%, respectively, P<0.0001; cornea: 53.0±16.0% vs. 11.0±2.1%, P=0.0297) (FIG. 3C). Moreover, in line with demonstrated increased proliferation, real-time quantitative PCR (qPCR) analysis of RNA expression revealed significant down-regulation in Abcb5 KO corneal epithelial cells of the p53 family (p53 and p63) and the Cip/Kip family (p21 and p27) of cell cycle regulators, which control the G0/G1 cell cycle checkpoint and cellular quiescence, as compared WT controls (41.6±16.4% of WT p53, P=0.0377; 31.2±13.8% of WT p63, P=0.0155; 37.2±13.8% of WT p21, P=0.0197; 36.8±7.0% of WT p27, P=0.0029) (FIG. 3D). Thus, ABCB5 is required for the maintenance of slow-cycling LSCs. Because withdrawal from the cell cycle is a prerequisite for LSC maintenance, and hence normal differentiation, these results provide an explanation for the observed corneal differentiation defect in Abcb5 KO mice (FIG. 3E).

Example 4. Regenerative Role of ABCB5(+) Limbal Stem Cells in Treatment of Limbal Stem Cell Deficiency To investigate whether ABCB5 represents a molecular marker for prospective enrichment of limbal stem cells within grafts to improve transplantation outcomes, the cornea-regenerative potential of transplanted limbal epithelial cells was examined. (FIGS. 14A and 14B and FIGS. 15A-15C). Murine donor limbal epithelial cells were transplanted onto the eyes of syngeneic C57BL/6J recipient mice with an induced limbal stem cell deficiency (LSCD). Human donor limbal epithelial cells were transplanted onto the eyes of immunodeficient NOD.Cg-Prkdc$^{scid}$ Il2rg$^{tm1Wjl/SzJ}$ (NSG) mice with an induced limbal stem cell deficiency. Four types of donor transplants were performed: (i) ABCB5(+) limbal epithelial cells, (ii) ABCB5(−) limbal epithelial cells, (iii) unsegregated limbal epithelial cells, and (iv) grafts containing no cells (fibrin gel carrier only) (500 cells in fibrin gel vehicle/graft, 1 unilateral eye graft/mouse, n=5 mice/treatment group) (Table 2). Three days

TABLE 2

Number and viability of donor cells used for transplantation

| Donor | Unsegregated cells 500 cells/ graft/mouse ABCB5 | | ABCB5(+) cells (ABCB5-positive enriched) 500 cells/ graft/mouse ABCB5 | | ABCB5(−) cells (ABCB5-negative enriched) 500 cells/ graft/mouse ABCB5 | |
|---|---|---|---|---|---|---|
| | Positive | Negative | Positive | Negative | Positive | Negative |
| Mouse limbus | | | | | | |
| % of cells/graft | 0.367 | 99 | 51 | 43 | 0 | 99 |
| viable cells/graft (%) | 69 | 64 | 100 | 40 | 0 | 63 |
| viable cells/graft (number) | 1 | 319 | 255 | 86 | 0 | 312 |
| Human limbus | | | | | | |
| % of cells/graft | 0.03 | 99 | 59 | 40 | 0 | 100 |
| viable cells/graft (%) | 93 | 22 | 99 | 40 | 0 | 90 |
| viable cells/graft (number) | 1 | 109 | 292 | 80 | 0 | 450 | prior to transplantation, murine and human donor cells were seeded onto a fibrin carrier, which was prepared by dissolving fibrinogen and thrombin stock solutions (TISSUCOL-Kit Immuno, Baxter, Germany) in 1.1% NaCl and 1 mM CaCl2 to a final concentration of 10 mg/ml fibrinogen and 3 IU/ml thrombin as described [30]. On the day of transplantation, total LSCD was induced in anesthetized recipient mice by removing the corneal and limbal epithelium with an Algerbrush II corneal rust ring remover with a 0.5-mm burr (AMBLER Surgical, PA) [16]. Following induction of LSCD, recipient mice received fibrin gel carrier-based transplants that were secured through four sutures. Eyelids were sutured with 8-0 nylon sutures to keep the eyes closed. Ak-Spore Ophthalmic Ointment (Bacitracin Zinc, Neomycin Sulfate and Polymyxin B Sulfate, Akorn, IL) was applied on both eyes immediately after wounding and then twice per day for the next 48 hours to prevent corneal infection and dryness. Analgesia was provided by subcutaneous injections of 5-10 mg/kg Metacam (Boehringer Ingelheim Pharmaceuticals, CT), given preoperatively and by subcutaneous injections of 0.05-0.1 mg/kg of Buprenex (Reckitt Benckiser Pharmaceuticals, Berkshire, UK) every 12 hours for 24 hours postoperatively. In addition, after surgical recovery, mice were also treated with anti-inflammatory Inflanefran Forte eye drops (Allergan, MA) for the first 5 days, and then with 1% Avastin (Bevacizumab, Genentech, CA) eye drops daily for 5 days. Slit lamp examination was performed weekly until euthanasia. Eyes were enucleated postmortem and fixed in 10% buffered formalin for methacrylate embedding (Technovit, Heraeus Kulzer, Germany) or snap-frozen in Tissue-Teck OCT (Sakura Finetek, CA).

Figure 4A:
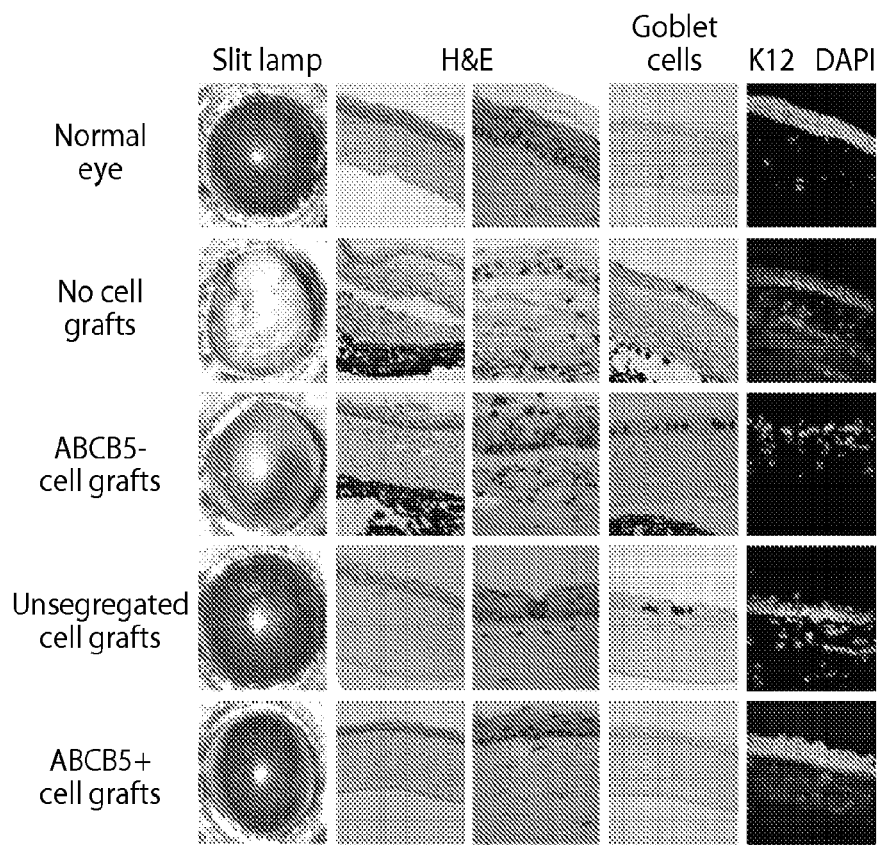
FIG. 4A shows analyses of murine syngeneic donor cell transplants grafted onto C57BL/6 recipient mice.
Figure 4A:
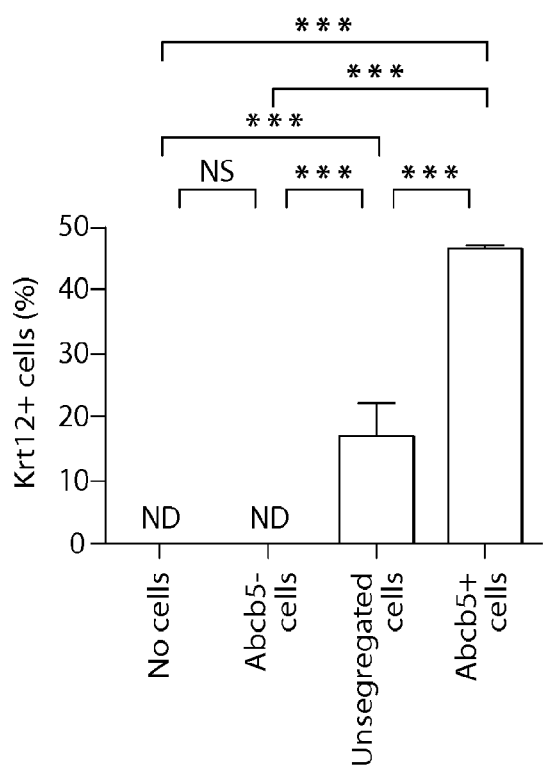
Figure 16A:
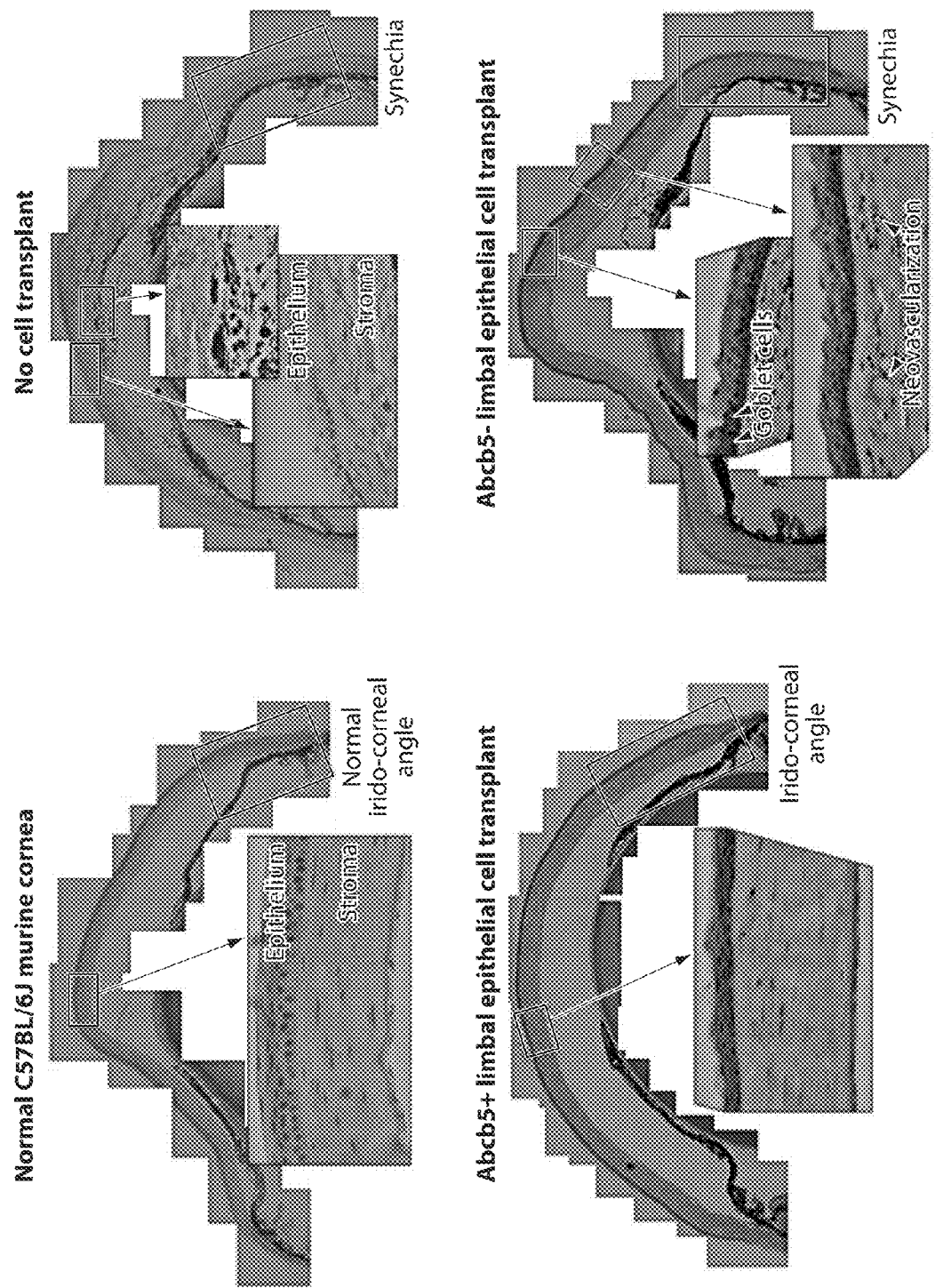
FIG. 16A shows representative H&E composite corneal cross sections of recipient C57BL/6J mice 5 weeks after receiving an induced limbal stem cell deficiency (LSCD) followed by engraftment of donor fibrin gel transplants containing the following syngeneic murine limbal epithelial cell subpopulations: (i) no cells (negative control), (ii) ABCB5(+) cells, (iii) ABCB5(−) cells or (iv) unsegregated cells. A normal untreated cornea (no LSCD) served as a positive control. The positive control displays the typical stratified corneal epithelium and iridocorneal angle. Mice receiving transplants with no cells displayed the typical conjunctivalization that occurs following a LSCD, i.e., unstratified conjunctival epithelium covers the cornea with extensive inflammation, neovascularization, and stromal edema. Synechia (where the iris adheres to the cornea) is typical of intense anterior segment inflammation. In contrast, mice that received transplants of ABCB5(+) cells, but not ABCB5(−) cells, displayed a restored stratified corneal epithelium with no evidence of inflammation, neovascularization, stromal edema, or synechia.
Figure 16B:
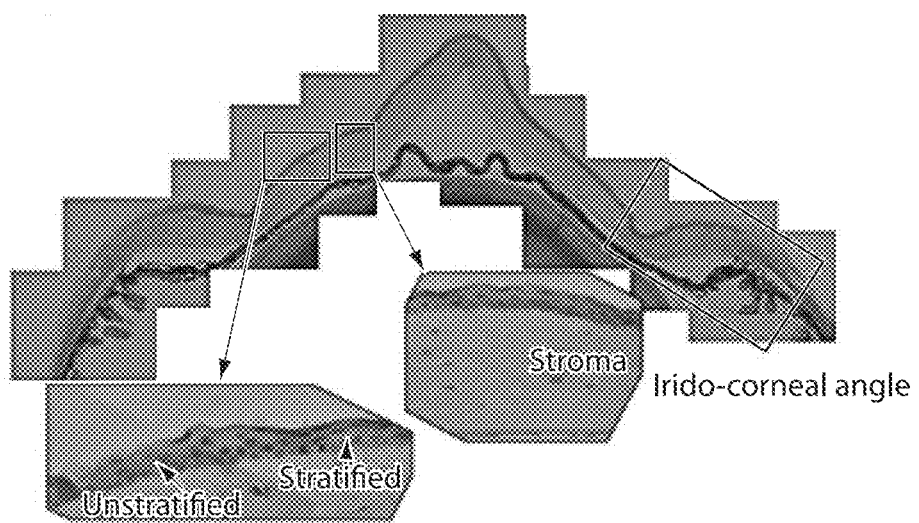
FIG. 16B shows mice that received transplants of unsegregated limbal epithelial cells displayed areas of stromal edema with unstratified epithelium, while other parts of the cornea contained normal stratified epithelial cells.

Recipients of syngeneic murine Abcb5(−) limbal cell grafts or vehicle-only negative controls displayed opaque corneas, epithelial conjunctivalization with infiltrating goblet cells, and absence of differentiated KRT12(+) cells (0%, respectively) when analyzed 5-weeks post transplantation, consistent with persistent LSCD (FIG. 4A, FIGS. 16A-16B). Recipients of syngeneic grafts containing unsegregated limbal cells displayed partial corneal restoration with detectable differentiated KRT12(+) cells in the central cornea (17% of cells, significantly enhanced compared to Abcb5(−) or vehicle-only treatment regimens, P<0.01), but exhibited persistence of LSCD-characteristic goblet cells and epithelial conjunctivalization (FIG. 4A, FIGS. 16A-16B). By contrast, syngeneic ABCB5(+) limbal cell grafts resulted in the development of clear corneas with normal histology in recipient mice, gave rise to higher numbers of differentiated KRT12(+) corneal epithelial cells (47% of cells, significantly increased compared unsegregated or ABCB5(−) limbal cell treatment regimens or compared vehicle-only controls, P<0.001) and prevented goblet cell formation or epithelial conjunctivalization (FIG. 4A, FIGS. 16A-16B).

Figure 4B:
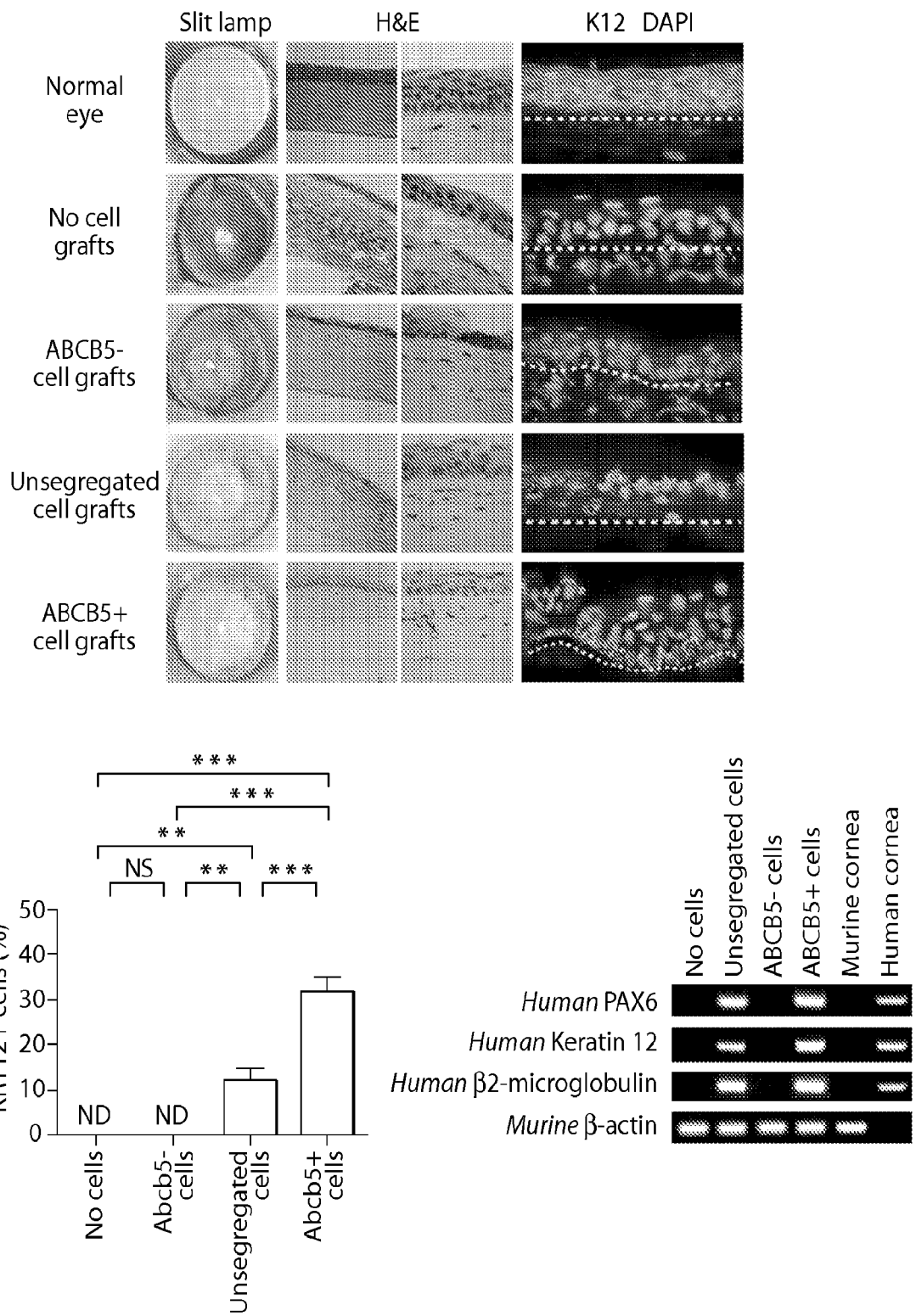
FIG. 4B shows analyses of human xenogeneic donor cell transplants grafted onto immunodeficient NSG recipient mice. The images show tissue five weeks post transplantation performed for the treatment of experimentally induced LSCD.
Figure 17A:
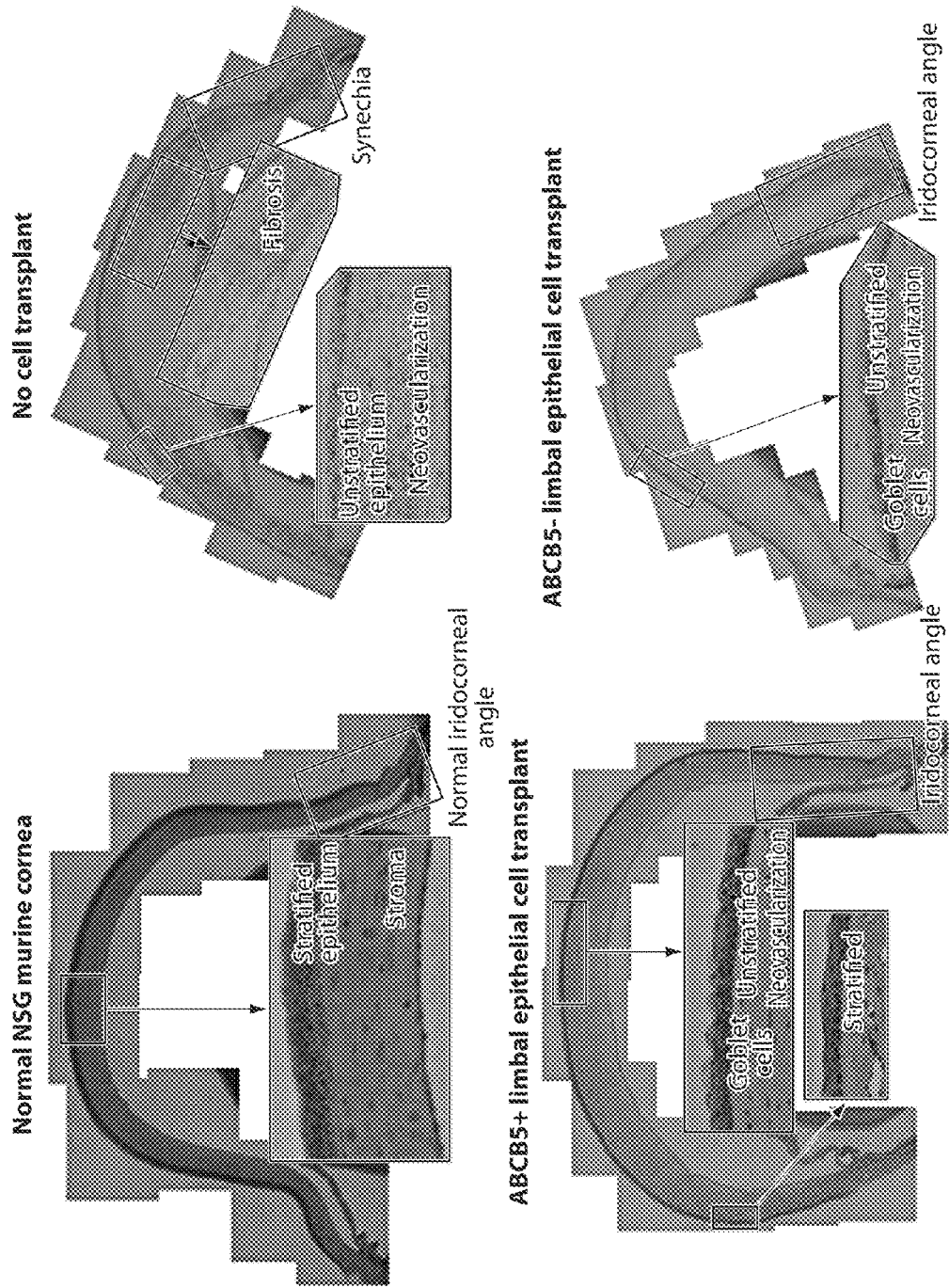
FIGS. 17A-17B show representative H&E composite corneal cross sections of recipient immunodeficient NSG mice 5 weeks after LSCD induction followed by transplantation of donor fibrin gel grafts containing the following human limbal epithelial cell subpopulations: (i) no cells (negative control), (ii) ABCB5(+) cells, (iii) ABCB5(−) cells, and (iv) unsegregated cells. A normal untreated NSG cornea (no LSCD) served as a positive control. The positive control displays the typical stratified corneal epithelium and iridocorneal angle. Mice that received transplants with no cells displayed evidence of conjunctivalization that occurs following a LSC deficiency, i.e., unstratified conjunctival epithelium covers the cornea with extensive neovascularization and synechia (anterior segment inflammation is muted in NSG mice due to their immunodeficiency). In contrast, mice that received transplants containing ABCB5(+) cells displayed areas of restored stratified epithelium, whereas mice that received ABCB5(−) cell grafts did not.
Figure 17B:
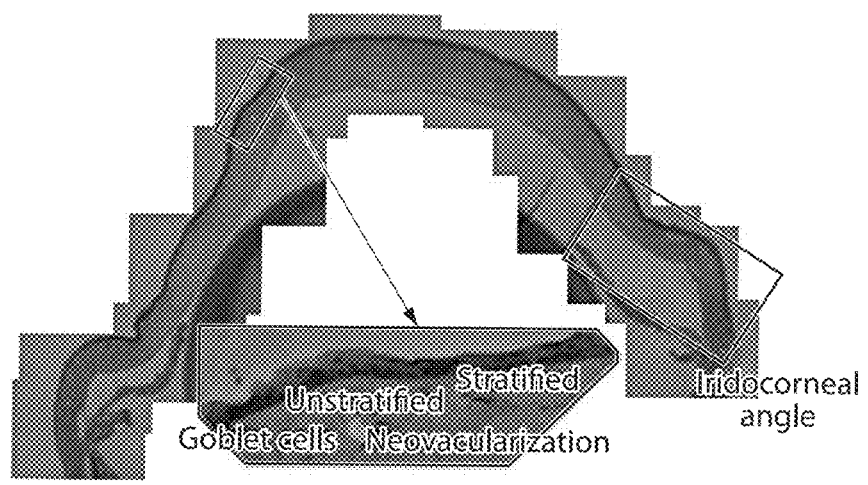
Figure 18:
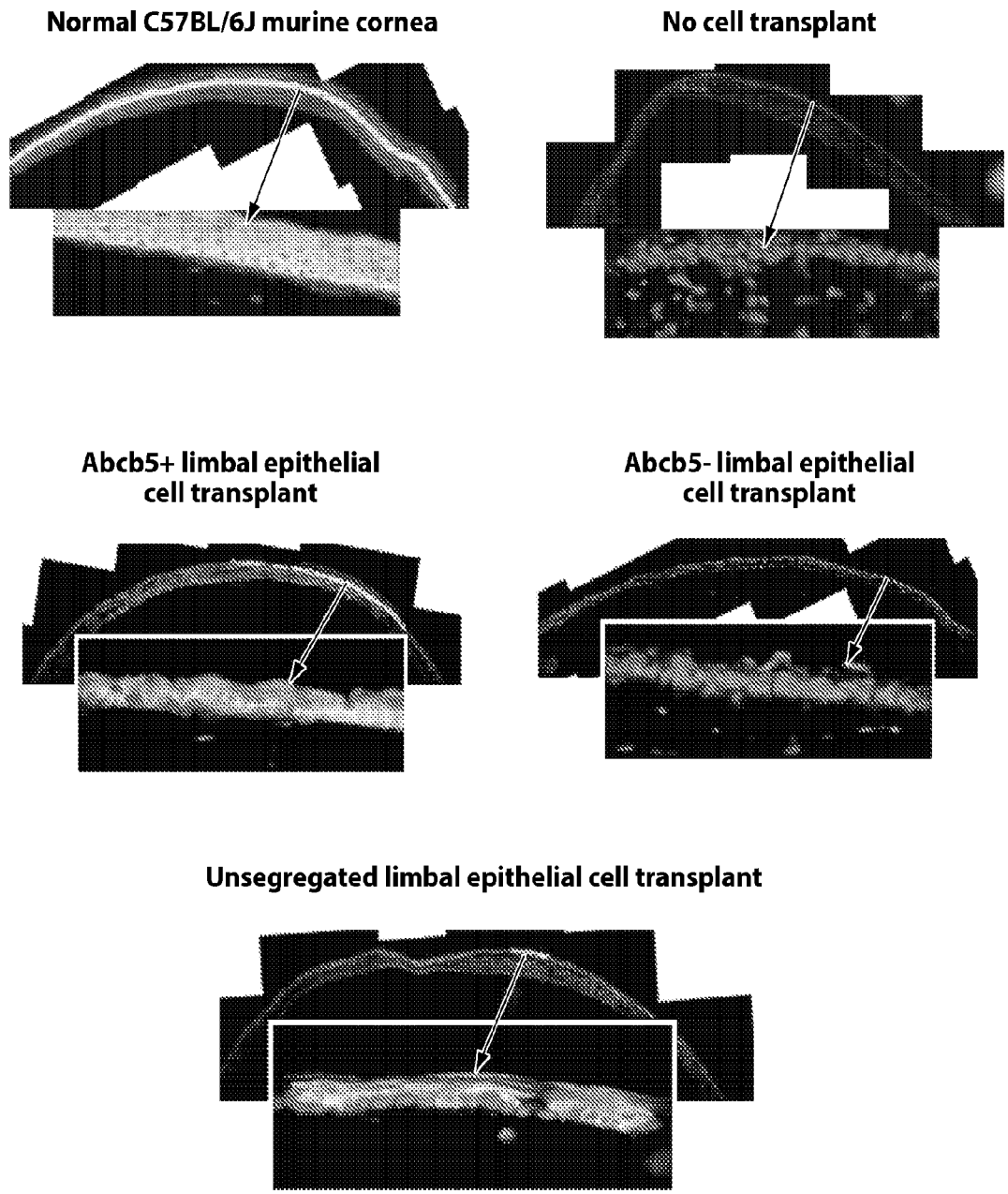
FIG. 18 shows representative immunofluorescent Krt12 staining (green) of recipient C57BL/6J mice 5 weeks after an LSCD induction followed by transplantation of donor fibrin gel grafts containing the following syngeneic murine limbal epithelial cell subpopulations: (i) no cells (negative control), (ii) ABCB5(+) cells, (iii) ABCB5(−) cells, or (iv) unsegregated cells. Normal untreated murine cornea (no LSCD), shown here as a positive control, displayed high intensity of KRT12 staining. As expected, mice that received grafts containing no cells, displayed no KRT12 expression. In contrast, mice transplanted with ABCB5(+) cells, exhibited significantly enhanced KRT12 expression in comparison to mice transplanted with unsegregated limbal epithelial cells. No KRT12 expression was detected in mice transplanted with ABCB5(−) cells. The white box depicts the area shown at 40× magnification. Montage images are shown at 10× magnification.

Immuno-compromised NSG recipients of freshly isolated human ABCB5(−) limbal cell grafts or vehicle-only negative controls also displayed epithelial conjunctivalization and absence of differentiated KRT12(+) cells (0%, respectively) 5-weeks post transplantation, consistent with persistent LSCD (FIG. 4B, FIGS. 17A-17B and 18). Immuno-compromised NSG recipients of freshly isolated human unsegregated limbal cell grafts, similar to findings in murine unsegregated limbal cell transplantation experiments, displayed partial corneal restoration with detectability of differentiated KRT12(+) cells in the central cornea (12% of cells, significantly enhanced vs. ABCB5(−) or vehicle-only treatment regimens, P<0.01), but exhibited persistence of LSCD characteristic epithelial conjunctivalization (FIG. 4B, FIGS. 17A-17B). Strikingly, only freshly isolated human ABCB5(+) limbal cell grafts resulted in the development of clear corneas with normal histology in recipient NSG mice with presence of a stratified epithelial layer containing high numbers of KRT12+ cells (31% of cells, significantly increased compared to vehicle-only or compared to ABCB5 (−) or unsegregated limbal cell treatment regimens, P<0.001) and absence of LSCD characteristic epithelial conjunctivalization (FIG. 4B, FIGS. 17A-17B).

In order to confirm that human donor cells had caused corneal restoration in this xenotransplantation model, regenerated corneal tissue was assayed by RT-PCR for expression of human-specific β2 microglobulin (β2M), an identifier of all cells of human origin, and for expression of human-specific PAX6 and KRT12 as markers of corneal differentiation. Only corneal epithelium of recipients grafted with human ABCB5(+) or unsegregated human limbal cells contained human-specific β2M, PAX6 and KRT12 transcripts, whereas vehicle-only-grafted control eyes that did not exhibit corneal restoration did not, confirming human specificity of the RT-PCR assay system (FIG. 4B). Moreover, despite similar viability in ABCB5(−) compared to unsegregated or ABCB5(+) cell grafts (Table 2, FIGS. 15A-15C), ABCB5(−) cell-grafted eyes were deficient in human-specific β2M, PAX6 or KRT12 transcript expression (FIG. 4B), indicating that long-term engraftment capacity is exclusively contained within the human ABCB5(+) limbal cell population.

The Examples provided herein demonstrate that ABCB5 (+) cell frequency is reduced in limbal stem cell deficiency (LSCD), that ABCB5-positivity preferentially characterizes slow-cycling and ΔNp63α-positive populations enriched for limbal stem cells (LSCs), and that prospectively isolated ABCB5(+) limbal cells are exclusively capable of reversing LSCD, indicating that ABCB5-positivity defines LSCs. These findings are further supported by data demonstrating that ABCB5 loss of function in Abcb5 gene knockout (KO) mice causes LSCD and impairs LSC-dependent corneal development and regeneration, through abrogation of LSC self-renewal capacity. These results have several important implications.

First, successful enrichment of human LSCs has the potential to decisively advance the field of LSCD therapy, because long-term clinical success has been shown to depend on limbal stem cell frequency within grafts[5] and because, prior to the present invention, no marker for prospective limbal stem cell enrichment has been available. Indeed, these Examples show that prospective limbal stem cell enrichment within grafts can significantly enhance LSCD therapeutic success. ABCB5 expression on the limbal stem cell surface permits monoclonal antibody-based cell sorting strategies and significant limbal stem cell enrichment as demonstrated herein, unlike intracellularly expressed ΔNp63α or alternative candidate limbal stem cell markers [17] that have not been successfully employed for prospective isolation of LSCs capable of LSCD reversal. This underscores the promise of ABCB5 as a potential marker for limbal stem cell isolation also for clinical limbal stem cell transplantation.

Second, the data provided herein reveal a novel in vivo physiological role of ABCB5 in the maintenance of stem cell quiescence. Specifically, abrogation of ABCB5 function in newly created Abcb5 KO mice resulted in loss of slow-cycling LSC with inhibited expression of molecules regulating G0/G1 cell cycle progression, including the limbal stem cell marker ΔNp63α. This explains the observed co-expression of ABCB5 with ΔNp63α by normally quiescent LSCs, and provides an explanation for induction of limbal stem cell proliferation and apoptosis associated with reduction of differentiated cells observed in Abcb5 KO corneas, because the ability of a cell to withdraw from the cell cycle is critical for both stem cell pool preservation and normal differentiation.

Additional Materials and Methods:

BrdU Pulse and Chase Experiments.

Four-week old Abcb5 KO mice and their Abcb5 WT littermates were subjected to daily intraperitoneal injections of 50 mg/kg Bromodeoxyuridine (BrdU, BD Pharmingen, CA) for 9 consecutive days (FIG. 5A). Corneal and limbal epithelial cells isolated from Abcb5 WT and Abcb5 KO mice sacrificed at either one week or eight weeks after receiving the last BrdU injection were analyzed by flow cytometry and immunofluorescence. Limbal and central corneal epithelial cells from age-matched Abcb5 WT and Abcb5 KO littermates were used as experimental controls. Flow cytometry and immunohistochemistry staining were used to determine the frequency of BrdU-positive and BrdU-negative cells within epithelia of the limbus and central cornea.

Human and Murine Corneal Cell Isolation.

Figure 15A:
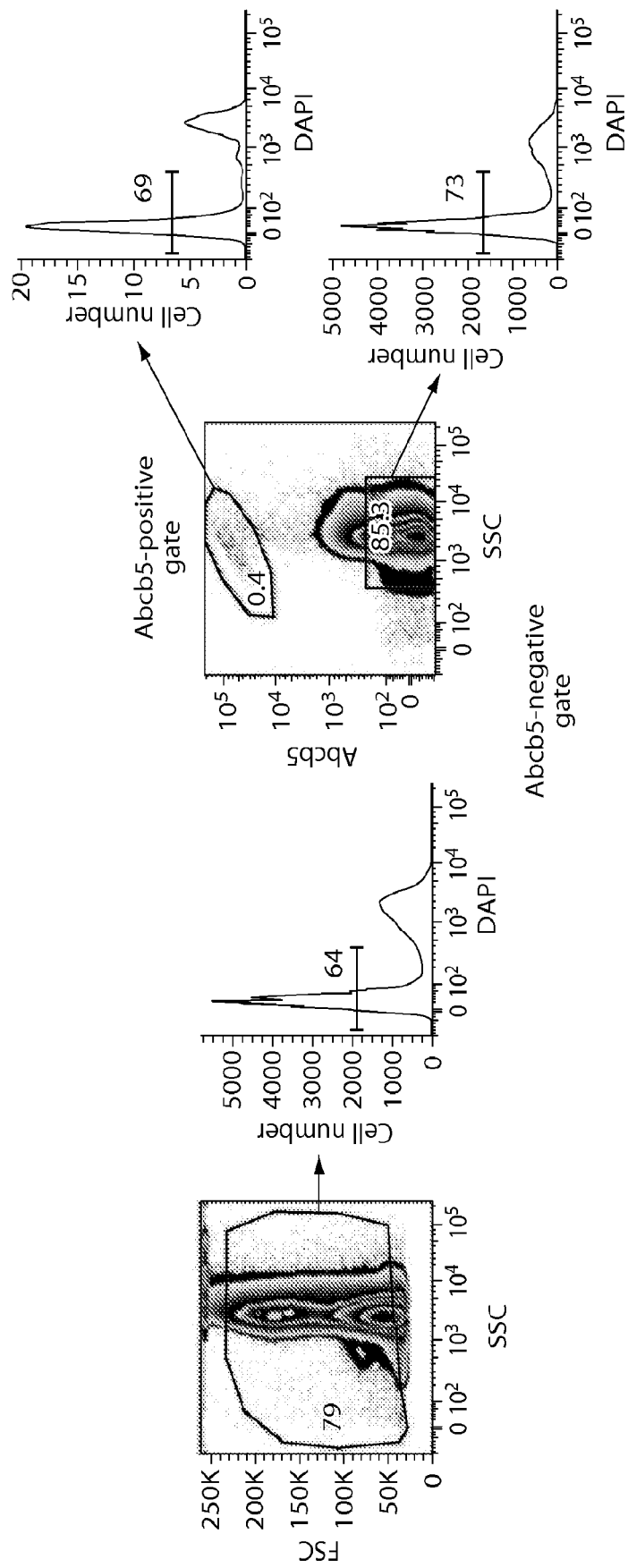
FIG. 15A shows representative flow cytometry analyses showing sorting gates and viability of murine donor limbal epithelial cells. Viability is shown as the percentage of cells excluding DAPI.
Figure 15B:
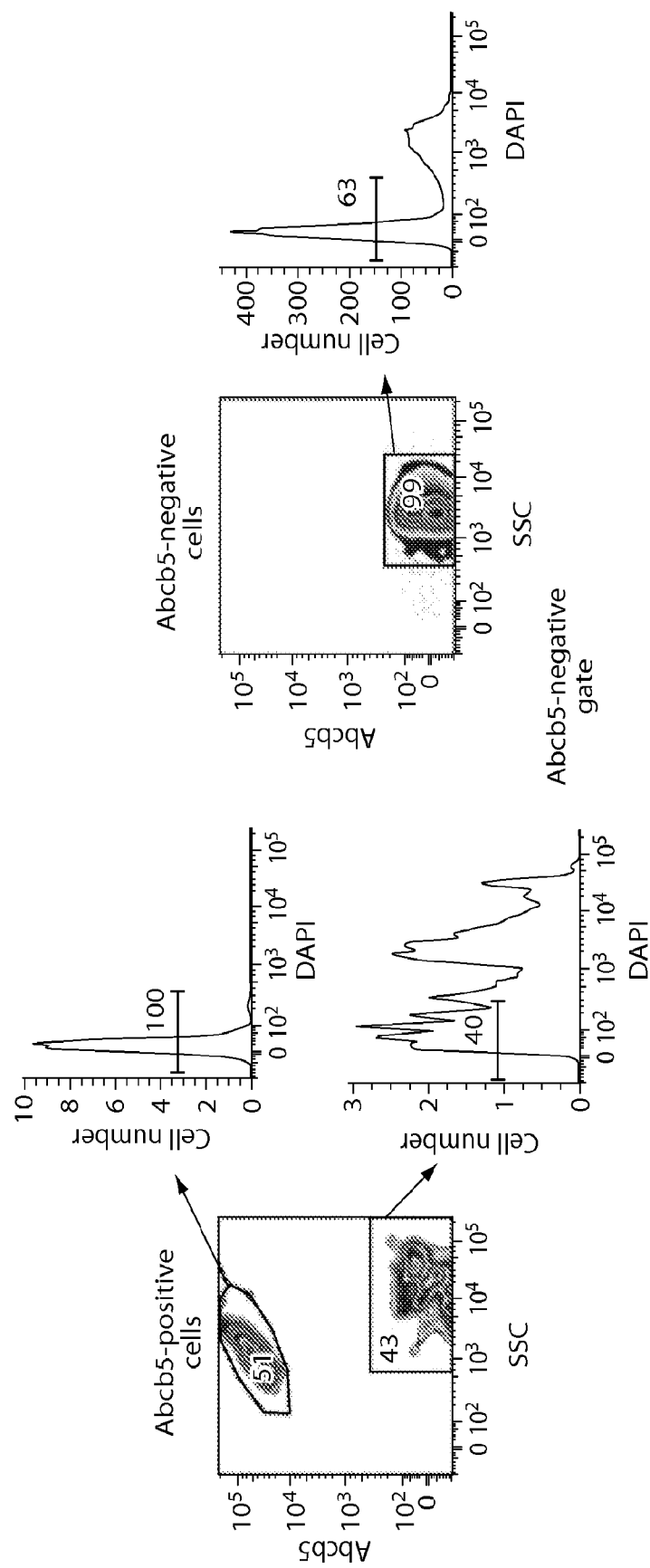
FIG. 15B shows post-sort analyses depicting the purity and viability of ABCB5(+)-enriched and ABCB5(−)-enriched subpopulations of limbal epithelial cells isolated from murine donors. Viability is shown as the percentage of cells excluding DAPI.
Figure 15C:
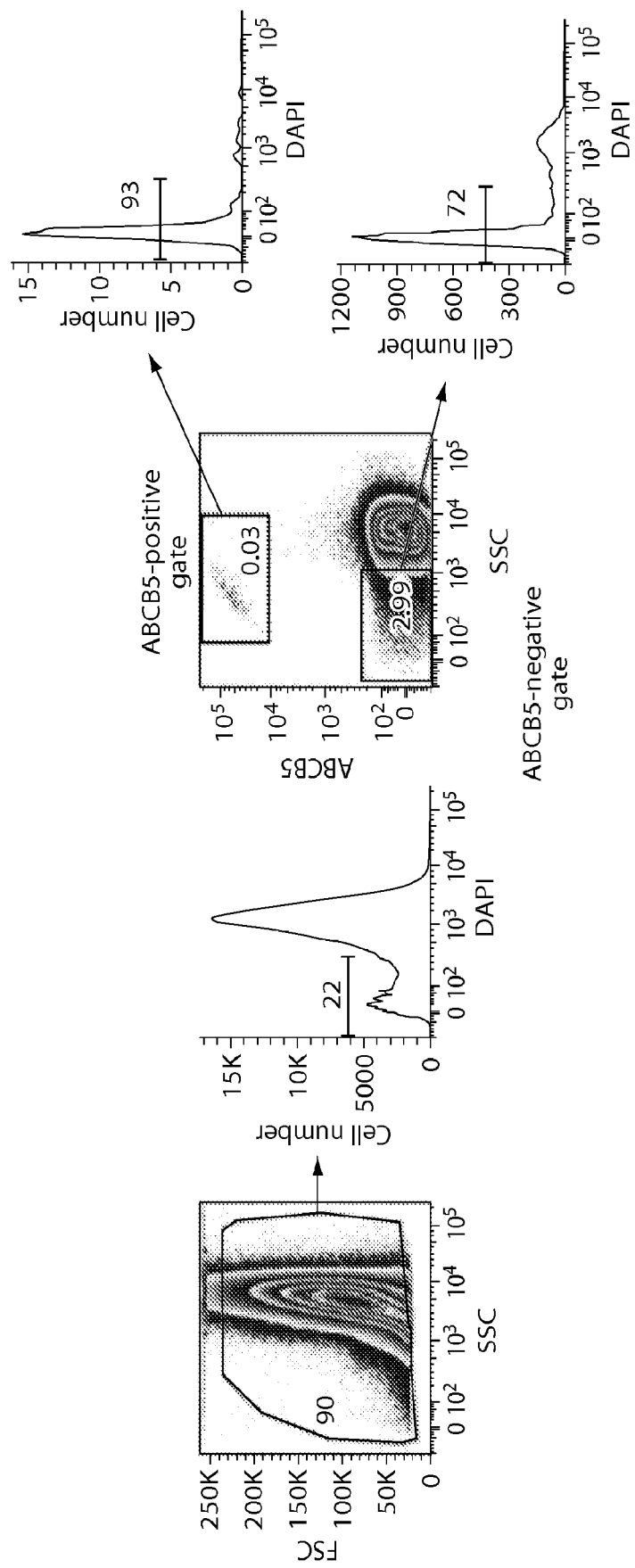
FIG. 15C shows representative flow cytometry analyses showing sorting gates and viability of human donor limbal epithelial cells.
Figure 15D:
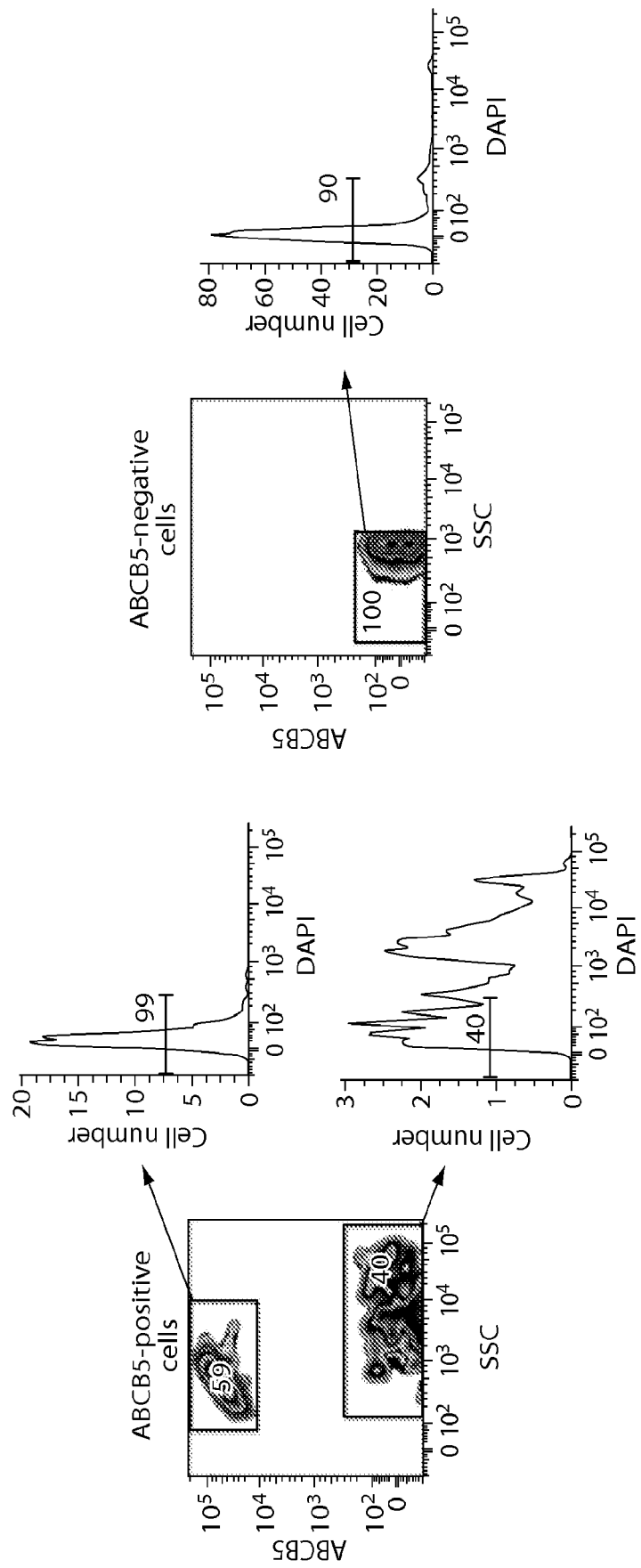
FIG. 15D shows post-sort analyses depicting the purity and viability of ABCB5(+)-enriched and ABCB5(−)-enriched subpopulations of limbal epithelial cells isolated from human donors. Viability is shown as the percentage of cells excluding DAPI.

Cadaveric human corneoscleral tissues derived from consented donors were obtained from Heartland Lions Eye Banks (Kansas City, Mo.), Bascom Palmer Eye Institute (Miami, Fla.), and Carver College of Medicine (Iowa City, Iowa). After removal of the scleral rim, iris and trabecular meshwork, the limbus and central cornea were dissected under a microscope. Limbal and central corneal tissues were subsequently incubated with 2.4 units/ml Dispase II (Roche Diagnostics, IN) at 37° C. for 1 hour, followed by incubation with 0.5M EDTA (Invitrogen, CA) at 37° C. for ten 5-minute cycles to recover the epithelial cells [22,23]. Murine limbal and corneal epithelial cells were obtained from Abcb5 KO and Abcb5 WT mice as follows. Immediately after euthanasia by $CO^2$ narcosis and subsequent eye enucleation, limbal and central corneal tissues were removed with micro scissors under a dissecting microscope, placed in low $Ca^{2+}$ Keratinocyte Serum Free Medium (KSFM, Invitrogen, CA) and centrifuged for 5 min at 250 g at 4° C. After removal of the supernatant, tissue pellets were digested in 0.5% Trypsin solution (Lonza, Md.) [24]. For transplantation experiments, ABCB5(+) and ABCB5(−) limbal epithelial cells were isolated by Fluorescence Activated Cell Sorting (FACS) using ABCB5 monoclonal antibody (mAb) labeling [18]. Briefly, either human or murine limbal epithelial cells were labeled with primary ABCB5 mAb (20 µg/µl) for 30 minutes at 4° C., washed to remove excess antibody, followed by a 30 minute incubation with secondary anti-mouse FITC conjugated IgG. The ABCB5(+) and ABCB5(−) sorting gates were established on a Modified Digital Vantage cell sorter (Becton Dickinson and MGH Pathology Flow Cytometry Core, Simches Research Building, Boston) as displayed in FIGS. 15A-15C. Only viable cells were selected for sorting by excluding all DAPI(+) cells (1 µg/ml DAPI, Sigma-Aldrich, MO, added immediately prior to sorting) as identified using a 70 MW UV laser for excitation. The purity and viability of ABCB5(+) and ABCB5(−) sorted cells were established in representative post sort analyses in which samples were re-analyzed (FIGS. 15A-15C). ABCB5(+) cell purification resulted in a 255-fold increase for murine ABCB5(+) limbal cells (0.37% positivity before and 51% positivity after sorting, Table 2) and a 292-fold increase for human ABCB5(+) limbal cells (0.03% positivity before and 59% positivity after sorting, Table 2). ABCB5(−) cell enrichment resulted in complete absence of ABCB5(+) cells in both mouse and human samples (Table 2).

Flow Cytometric Analysis.

Dual-color flow cytometry was used to determine whether human ABCB5(+) limbal epithelial cells co-expressed ΔNp63α or KRT12 and whether murine ABCB5(+) limbal epithelial cells co-expressed PAX6 and KRT12, and was performed as described previously [18]. For human and murine ABCB5 and KRT12 co-expression analysis, cells were first incubated with mouse anti-ABCB5 mAb, counterstained with goat anti-mouse FITC IgG, followed by incubation with goat polyclonal anti-KRT12 antibody and counterstaining with Dylight 649 donkey anti-goat IgG. For human ABCB5 and ΔNp63α co-expression and murine ABCB5 and PAX6 co-expression analysis, cells were incubated with mouse anti-ABCB5 mAb, counterstained with goat anti-mouse FITC IgG, permeabilized in BD Cytofix/Cytoperm Buffer (BD Biosciences, CA), stained with either ΔNp63α or PAX6 Abs, and counterstained with goat anti-rabbit Alexa 647 IgG. Washing steps with staining buffer or BD Perm/Wash Buffer (BD Biosciences, CA) were performed between each step. Dual-color flow cytometry was performed by acquisition of fluorescence emission at the Fl1 (FITC) and Fl4 (Alexa 647 and/or Dylight 649) spectra on a Becton Dickinson FACScan (Becton Dickinson, NJ), as described [18]. Murine ABCB5 and BrdU co-expression analysis was performed using the FITC BrdU Flow Kit (BD Biosciences, CA), according to the manufacturer's instructions. Statistical differences between expression levels of the above-listed markers by ABCB5(+) and ABCB5(−) cells were determined using the unpaired t test. A two-sided P value of P<0.05 was considered significant.

RT-PCR and Quantitative Real Time PCR.

For cell cycle gene expression analyses, total RNA was isolated from Abcb5 KO and Abcb5 WT corneas using a $RT^2$ qPCR Grade RNA isolation kit and then reverse-transcribed using a $RT^2$ First Strand Kit for reverse transcriptase-PCR according to the manufacturer's protocol (SABiosciences, CA). Samples were assayed using SYBR Green qPCR Master Mixes (SABiosciences, CA), murine cell cycle arrays (catalog number PAMM-020Z, SABiosciences, CA) and kinetic PCR (ABI 7700 Sequence Detector; Applied Biosystems, CA), as described [28]. All quantifications were normalized to the endogenous control genes glyceraldehyde-3-phosphate dehydrogenase (GAPDH) and β-actin, to account for variability in the initial concentration and quality of the total RNA, and efficiency of the reverse transcription reaction. Statistical differences in gene expression levels between Abcb5 KO and Abcb5 WT mice were determined using the one sample t test. A two-sided P value of P<0.05 was considered significant. For detection of human-specific gene transcripts, total RNA was isolated from transplanted murine eyes and non-injured murine or human control corneas using the RNAeasy Plus isolation kit (Qiagen, CA) and then transcribed using the High Fidelity RT kit (Applied Biosystems, CA). PCR was performed using Taq 2× Master Mix (New England Biolabs, MA) and the following gene-specific primers: human β2-microglobulin (B2M, NM_004048): Forward 5'-GTGTCTGGGTTTCATCCATC-3' (SEQ ID NO:13), Reverse 5'-AATGCGGCATCT-TCAACCTC-3' (SEQ ID NO:14); human paired box 6 (PAX6, NM_000280.3): Forward 5'-CAGCGCTCTGC-CGCCTAT-3' (SEQ ID NO:15), Reverse 5'-CATGAC-CAACACAGATCAAACATCC-3' (SEQ ID NO:16); human keratin 12 (KRT12, NM_000223.3): Forward 5'-GAAGCCGAGGGCGATTACTG-3' (SEQ ID NO:17), Reverse 5'-GTGCTTGTGATTTGGAGTCTGTCAC-3' (SEQ ID NO:18); and murine β-actin (Actb, NM_007393): Forward 5'-TCCTAGCACCATGAAGATC-3' (SEQ ID NO:19), Reverse 5'-AAACGCAGCTCAGTAACAG-3' (SEQ ID NO:20).

Histopathology and Immunohistochemical Staining.

To recover intact mouse ocular tissue, the whole decapitated mouse head was fixed in 4% paraformaldehyde (PFA) overnight, then eyes were enucleated with the lids attached, incubated in 30% sucrose in 1× phosphate buffered saline (PBS) overnight at 4° C., embedded in Tissue-Tek OCT compound (Sakura Finetek USA, CA) and snap-frozen. Representative cryostat sections from each tissue block were stained with hematoxylin and eosin (H&E). For immunofluorescence staining, cryostat sections (10 µm) were fixed in cold methanol for 10 minutes, blocked in 10% secondary serum+2% bovine serum albumin (BSA) in 1×PBS for 1 hour, incubated with the primary antibody (or isotype control), followed by the appropriate secondary antibody for 1 hour at room temperature. Following several washes, the slides were then cover-slipped in hard-set mounting media with 4',6-diamidino-2-phenylindole (DAPI). BrdU staining was performed using the BrdU In-situ Kit (BD Pharmingen, CA) followed by staining with rabbit ABCB5 antibody at 1:250 dilution (NBP1-50547, Novus, CO). TUNEL staining was performed using the In Situ Cell Death Kit (Roche, IN) and DAPI (Invitrogen, MA) was used to stain all nucleated cells. All tissue sections were analyzed using a Nikon Eclipse E800 immunofluorescence microscope. Composite corneal photographs were assembled using Photoshop (Adobe) to overlay and match sequential images. Stitching was done by reducing the added photograph to 50% transparency, matching images, and returning the composite photograph to 0% transparency. The average number of epithelial cells per cornea (FIG. 2D) was determined by counting the number of DAPI-positive cells within the area defined by a 2 mm trephine in a composite photograph of a complete corneal section. At least three composite corneal sections were analyzed per mouse, and five mice were analyzed per group in four replicate experiments. The percentages of epithelial cells expressing Ki67 (FIGS. 2I and 3C), TUNEL (FIG. 2I) and KRT12 (FIGS. 4A and 4B) were determined by counting the number of positive cells among the total number of DAPI-positive corneal epithelial cells using the techniques described herein. Comparisons between the Abcb5 WT and Abcb5 KO mice were performed using the unpaired t test. The results of transplantation experiments were compared using One-way ANOVA followed by Bonferroni post tests. Differences with P<0.05 were considered statistically significant.

Antibodies.

The following primary antibodies were used in flow cytometry experiments: rabbit polyclonal anti-ΔNp63α antibody (cloneH-129, Santa Cruz, Calif.), mouse monoclonal anti-ABCB5 antibody (clone 3C2-2D12) [6], goat polyclonal anti-cytokeratin antibody (clone L15, Santa Cruz, Calif.), rabbit polyclonal anti-PAX6 antibody (Covance, CA), rabbit polyclonal anti-ABCB5 antibody (Novus Biologicals, CO), rabbit polyclonal IgG isotype control antibody (Abcam, MA), mouse IgG1k isotype control antibody (BD Biosciences, CA), and goat IgG isotype control antibody (Santa Cruz, Calif.). The secondary antibodies were goat anti-mouse FITC (Sigma-Aldrich, MO), Alexa 647 goat anti-rabbit IgG (Invitrogen, NY) and Dylight 649 donkey anti-goat (Jackson ImmunoResearch, PA). For human histopathology and immunohistochemical analyses, the following primary antibodies were used: mouse monoclonal anti-ABCB5 (clone 3C2-1D12) [6] and rabbit antibody against ΔNp63α at 1:75 dilution (sc8344, Santa Cruz, Calif.) followed by the appropriate secondary antibodies obtained from Jackson ImmunoResearch, PA: FITC-donkey anti-rabbit at 1:75 dilution or Alexa Fluor 594-goat anti-mouse at 1:250 dilution. In all cases, isotype-matched antibodies rabbit IgG (550875, BD Pharmingen, CA) and mouse IgG1kappa isotype control antibody (BD Biosciences, CA) served as negative controls. For histopathology and immunohistochemical analyses mouse tissues were stained with the following primary antibodies: rabbit anti-ABCB5 antibody at 1:250 dilution (NBP1-50547, Novus, CO), rabbit anti-Pax6 at 1:300 dilution (PRB278P, Covance, CA), goat anti-cytokeratin 12 (L15) at 1:50 dilution (sc17101, Santa Cruz, Calif.), rabbit anti-cytokeratin 14 (AF64) at 1:1000 dilution (PRB-155P, Covance, CA), rabbit anti-Ki67 at 1:200 dilution (ab66155, Abcam, MA), followed by the appropriate secondary antibodies obtained from Jackson ImmunoResearch, PA: donkey anti-goat Alexa Fluor 488 at 1:250 dilution (705-545-003), donkey anti-rabbit Alexa Fluor 594 at 1:20 dilution (711-585-152), goat anti-rabbit DyLight 549 at 1:250 dilution (111-504-144), or Cy3-donkey anti-rabbit at 1:250 dilution (711-165-152). In all cases, isotyped matched antibodies (rabbit IgG (550875, BD Pharmingen, CA) and goat IgG (sc2028, SantaCruz, Calif.) served as negative controls.

The concurrently filed Sequence Listing, filed as a text file, is incorporated by reference herein.

REFERENCES

Each of the references listed below is incorporated by reference herein in its entirety.

1. Davanger, M. & Evensen, A. Role of the pericorneal papillary structure in renewal of corneal epithelium. *Nature* 229, 560-1 (1971).
2. Cotsarelis, G., Cheng, S. Z., Dong, G., Sun, T. T. & Lavker, R. M. Existence of slow cycling limbal epithelial basal cells that can be preferentially stimulated to proliferate: implications on epithelial stem cells. *Cell* 57, 201-9 (1989).
3. Majo, F., Rochat, A., Nicolas, M., Jaoude, G. A. & Barrandon, Y. Oligopotent stem cells are distributed throughout the mammalian ocular surface. *Nature* 456, 250-4 (2008).
4. Dua, H. S., Joseph, A., Shanmuganathan, V. A. & Jones, R. E. Stem cell differentiation and the effects of deficiency. *Eye (Lond)* 17, 877-85 (2003).
5. Rama, P. et al. Limbal stem-cell therapy and long-term corneal regeneration. *N Engl J Med* 363, 147-55 (2010).
6. Frank, N. Y. et al. Regulation of progenitor cell fusion by ABCB5 P-glycoprotein, a novel human ATP-binding cassette transporter. *J Biol Chem* 278, 47156-65 (2003).
7. Schatton, T. et al. Identification of cells initiating human melanomas. *Nature* 451, 345-9 (2008).
8. Pellegrini, G. et al. p63 identifies keratinocyte stem cells. *Proc Natl Acad Sci USA* 98, 3156-61 (2001).
9. Li, W. et al. Down-regulation of Pax6 is associated with abnormal differentiation of corneal epithelial cells in severe ocular surface diseases. *J Pathol* 214, 114-22 (2008).
10. Sun, T. T. & Lavker, R. M. Corneal epithelial stem cells: past, present, and future. *J Investig Dermatol Symp Proc* 9, 202-7 (2004).
11. Liu, C. Y. et al. Characterization and chromosomal localization of the cornea-specific murine keratin gene Krt1.12. *J Biol Chem* 269, 24627-36 (1994).
12. Luo, Y. et al. Side population cells from human melanoma tumors reveal diverse mechanisms for chemoresistance. *J Invest Dermatol* 132, 2440-50.
13. Wilson, B. J. et al. ABCB5 identifies a therapy-refractory tumor cell population in colorectal cancer patients. *Cancer Res* 71, 5307-16 (2011).
14. Hutcheson, D. A. & Kardon, G. Genetic manipulations reveal dynamic cell and gene functions: Cre-ating a new view of myogenesis. *Cell Cycle* 8, 3675-8 (2009).
15. Lakso, M. et al. Efficient in vivo manipulation of mouse genomic sequences at the zygote stage. *Proc Natl Acad Sci USA* 93, 5860-5 (1996).
16. Meyer-Blazejewska, E. A. et al. From hair to cornea: toward the therapeutic use of hair follicle-derived stem cells in the treatment of limbal stem cell deficiency. *Stem Cells* 29, 57-66 (2011).
17. Watanabe, K. et al. Human limbal epithelium contains side population cells expressing the ATP-binding cassette transporter ABCG2. *FEBS Lett* 565, 6-10 (2004).
18. Frank, N. Y. et al. ABCB5-mediated doxorubicin transport and chemoresistance in human malignant melanoma. *Cancer Res* 65, 4320-33 (2005).
19. Cheung, S. T., Cheung, P. F., Cheng, C. K., Wong, N. C. & Fan, S. T. Granulin-epithelin precursor and ATP-dependent binding cassette (ABC)B5 regulate liver cancer cell chemoresistance. *Gastroenterology* 140, 344-55 (2011).
20. Yang, M. et al. Expression of ABCB5 gene in hematological malignances and its significance. *Leuk Lymphoma* 53, 1211-5 (2012).
21. Lehne, G. et al. Upregulation of stem cell genes in multidrug resistant K562 leukemia cells. *Leuk Res* 33, 1379-85 (2009).
22. Pellegrini, G. et al. Location and clonal analysis of stem cells and their differentiated progeny in the human ocular surface. *J Cell Biol* 145, 769-82 (1999).
23. Meyer-Blazejewska, E. A. et al. Preservation of the limbal stem cell phenotype by appropriate culture techniques. *Invest Ophthalmol Vis Sci* 51, 765-74 (2010).
24. Krulova, M. et al. A rapid separation of two distinct populations of mouse corneal epithelial cells with limbal stem cell characteristics by centrifugation on percoll gradient. *Invest Ophthalmol Vis Sci* 49, 3903-8 (2008).
25. Liu, P., Jenkins, N. A. & Copeland, N. G. A highly efficient recombineering-based method for generating conditional knockout mutations. *Genome Res* 13, 476-84 (2003).

26. Rodriguez, C. I. et al. High-efficiency deleter mice show that FLPe is an alternative to Cre-loxP. *Nat Genet* 25, 139-40 (2000).
27. Frank, N. Y. et al. VEGFR-1 expressed by malignant melanoma-initiating cells is required for tumor growth. *Cancer Res* 71, 1474-85 (2011).
28. Frank, N. Y. et al. Regulation of myogenic progenitor proliferation in human fetal skeletal muscle by BMP4 and its antagonist Gremlin. *J Cell Biol* 175, 99-110 (2006).
29. Pal-Ghosh, S., Pajoohesh-Ganji, A., Brown, M. & Stepp, M. A. A mouse model for the study of recurrent corneal epithelial erosions: alpha9beta1 integrin implicated in progression of the disease. *Invest Ophthalmol Vis Sci* 45, 1775-88 (2004).
30. Pellegrini, G. et al. The control of epidermal stem cells (holoclones) in the treatment of massive full-thickness burns with autologous keratinocytes cultured on fibrin. *Transplantation* 68, 868-79 (1999).
31. Klocke, J. et al. Spontaneous bacterial keratitis in DC36 knockout mice. *Invest Ophthalmol Vis Sci* 52(1), 256-63 (2011) (including Supplemental Appendix).
32. Okita, K, et al. Generation of germline competent induced pluripotent stem cells. *Nature* 448: 313-317 (2007).
33. Stadfeld, M. and Hochedlinger, K. Induced pluripotency: history, mechanisms, and applications, *Genes and Development* 24, 2239-2263 (2010).

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

All references, patents and patent applications disclosed herein are incorporated by reference with respect to the subject matter for which each is cited, which in some cases may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of treating a subject having an ocular condition, wherein the ocular condition is a corneal disease, comprising administering to the subject isolated ABCB5(+) ocular stem cells, wherein the ocular stem cells are limbal stem cells, in an amount effective to regenerate ocular cells in the subject.

2. The method of claim 1, wherein the corneal disease is blindness due to limbal stem cell deficiency (LSCD).

3. The method of claim 1, wherein the corneal disease is blindness due to corneal epithelium wounding.

4. The method of claim 1, wherein the isolated ABCB5(+) limbal stem cells are administered as an ocular graft.

5. The method of claim 1, wherein the isolated ABCB5(+) limbal stem cells are allogeneic stem cells.

6. The method of claim 1, wherein the isolated ABCB5(+) limbal stem cells are syngeneic stem cells.

7. A method of promoting ocular cell regeneration, wherein the ocular cells are corneal cells, comprising identifying limbal stem cells as ABCB5(+) limbal stem cells and administering to a subject in need thereof the ABCB5(+) limbal stem cells in an amount effective to promote corneal cell regeneration.

8. The method of claim 7, wherein the isolated ABCB5(+) limbal stem cells are administered as an ocular graft.

9. The method of claim 7, wherein the isolated ABCB5(+) limbal stem cells are allogeneic stem cells.

10. The method of claim 7, wherein the identifying step involve use of an antibody specific to ABCB5.

* * * * *

UNITED STATES PATENT AND TRADEMARK OFFICE
CERTIFICATE OF CORRECTION

PATENT NO. : 9,801,912 B2
APPLICATION NO. : 14/768885
DATED : October 31, 2017
INVENTOR(S) : Markus H. Frank et al.

It is certified that error appears in the above-identified patent and that said Letters Patent is hereby corrected as shown below:

In the Specification

At Column 1, Line 14, please replace the paragraph titled FEDERALLY SPONSORED RESEARCH with the following paragraph:
FEDERALLY SPONSORED RESEARCH
This invention was made with government support under grant number CA113796 awarded by the National Institutes of Health. The Government has certain rights in this invention.

Signed and Sealed this
Twenty-ninth Day of January, 2019

Andrei Iancu
*Director of the United States Patent and Trademark Office*